(12) United States Patent
Weeks et al.

(10) Patent No.: US 9,474,688 B2
(45) Date of Patent: *Oct. 25, 2016

(54) DELAMINATION RESISTANT PHARMACEUTICAL GLASS CONTAINERS CONTAINING ACTIVE PHARMACEUTICAL INGREDIENTS

(71) Applicant: Corning Incorporated, Corning, NY (US)

(72) Inventors: Wendell Porter Weeks, Corning, NY (US); Robert Anthony Schaut, Painted Post, NY (US); Steven Edward DeMartino, Painted Post, NY (US); John Stephen Peanasky, Big Flats, NY (US)

(73) Assignee: Corning Incorporated, Corning, NY (US)

( * ) Notice: Subject to any disclaimer, the term of this patent is extended or adjusted under 35 U.S.C. 154(b) by 421 days.

This patent is subject to a terminal disclaimer.

(21) Appl. No.: 13/660,680

(22) Filed: Oct. 25, 2012

(65) Prior Publication Data

US 2013/0216742 A1    Aug. 22, 2013

Related U.S. Application Data

(60) Provisional application No. 61/551,163, filed on Oct. 25, 2011, provisional application No. 61/656,998, filed on Jun. 7, 2012.

(51) Int. Cl.
*C03C 4/00* (2006.01)
*A61J 1/00* (2006.01)
(Continued)

(52) U.S. Cl.
CPC ............... *A61J 1/1468* (2015.05); *A61J 1/00* (2013.01); *A61J 1/065* (2013.01); *A61K 31/403* (2013.01);
(Continued)

(58) Field of Classification Search
CPC ...... C03C 3/087; C03C 3/031; C03C 21/002; C03C 4/20
USPC ................. 428/34.4; 501/62, 69, 70
See application file for complete search history.

(56) References Cited

U.S. PATENT DOCUMENTS 3,490,885 A    1/1970    Hammer
3,772,135 A    11/1973   Hara et al.
(Continued)

FOREIGN PATENT DOCUMENTS

CN    101717189 A    6/2010
DE    29702816 U1    4/1997
(Continued)

OTHER PUBLICATIONS

Adams RA. Formal discussion: the role of transplantation in the experimental investigation of human leukemia and lymphoma. Cancer Res. Dec. 1967;27(12):2479-82.

(Continued)

*Primary Examiner* — Ellen S Wood
(74) *Attorney, Agent, or Firm* — Michael G. Panian

(57) ABSTRACT

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage of pharmaceutical compositions and, specifically, a pharmaceutical solution comprising a pharmaceutically active ingredient.

35 Claims, 6 Drawing Sheets

(51) Int. Cl.

| | |
|---|---|
| A61K 39/395 | (2006.01) |
| C03C 3/087 | (2006.01) |
| C03C 3/091 | (2006.01) |
| C03C 21/00 | (2006.01) |
| C03C 4/20 | (2006.01) |
| A61J 1/06 | (2006.01) |
| A61K 38/17 | (2006.01) |
| A61K 38/19 | (2006.01) |
| A61K 38/28 | (2006.01) |
| A61K 31/403 | (2006.01) |
| A61K 38/18 | (2006.01) |
| C07K 16/24 | (2006.01) |

(52) U.S. Cl.
CPC ........... *A61K 38/17* (2013.01); *A61K 38/1816* (2013.01); *A61K 38/193* (2013.01); *A61K 38/28* (2013.01); *A61K 39/3955* (2013.01); *C03C 3/087* (2013.01); *C03C 3/091* (2013.01); *C03C 4/20* (2013.01); *C03C 21/002* (2013.01); *C07K 16/241* (2013.01); *Y10T 428/131* (2015.01)

(56) References Cited

U.S. PATENT DOCUMENTS

| | | | |
|---|---|---|---|
| 3,844,754 A | 10/1974 | Grubb et al. | |
| 4,065,317 A * | 12/1977 | Baak et al. | 501/70 |
| 4,689,085 A | 8/1987 | Plueddemann | |
| 5,114,757 A | 5/1992 | Linde et al. | |
| 5,286,527 A | 2/1994 | Blum et al. | |
| 5,547,929 A | 8/1996 | Anderson, Jr. et al. | |
| 5,547,933 A | 8/1996 | Lin | |
| 5,580,755 A | 12/1996 | Souza | |
| 5,582,823 A | 12/1996 | Souza | |
| 5,605,690 A | 2/1997 | Jacobs et al. | |
| 5,656,722 A | 8/1997 | Dorschug | |
| 5,721,181 A | 2/1998 | Sehgal et al. | |
| 5,736,476 A | 4/1998 | Watzke et al. | |
| 5,756,349 A | 5/1998 | Lin | |
| 5,824,784 A | 10/1998 | Kinstler et al. | |
| 5,854,153 A | 12/1998 | Kohli | |
| 5,955,422 A | 9/1999 | Lin | |
| RE36,755 E | 6/2000 | Smith et al. | |
| 6,096,432 A | 8/2000 | Sakaguchi et al. | |
| 6,214,429 B1 | 4/2001 | Zou et al. | |
| 6,472,068 B1 | 10/2002 | Glass et al. | |
| 6,518,211 B1 | 2/2003 | Bradshaw et al. | |
| 6,561,275 B2 | 5/2003 | Glass et al. | |
| 6,630,420 B1 | 10/2003 | Naumann et al. | |
| 6,794,323 B2 | 9/2004 | Peuchert et al. | |
| 6,818,576 B2 | 11/2004 | Ikenishi et al. | |
| RE38,743 E | 6/2005 | Debrie | |
| 6,939,819 B2 | 9/2005 | Usui et al. | |
| 7,087,307 B2 | 8/2006 | Nagashima et al. | |
| 7,315,125 B2 | 1/2008 | Kass | |
| 7,470,999 B2 | 12/2008 | Saito et al. | |
| 7,476,652 B2 | 1/2009 | Brunner-Schwarz et al. | |
| 7,915,225 B2 | 3/2011 | Finck | |
| 8,551,898 B2 | 10/2013 | Danielson et al. | |
| 8,753,994 B2 | 6/2014 | Danielson et al. | |
| 2004/0096588 A1 | 5/2004 | Brandt | |
| 2006/0154891 A1 | 7/2006 | Schridde et al. | |
| 2007/0004580 A1 | 1/2007 | Kass | |
| 2007/0010700 A1* | 1/2007 | Bensmann et al. | 588/1 |
| 2007/0065366 A1* | 3/2007 | Soliani Raschini et al. | 424/44 |
| 2007/0123410 A1 | 5/2007 | Morena et al. | |
| 2007/0157919 A1 | 7/2007 | Marandon | |
| 2007/0191207 A1 | 8/2007 | Danielson et al. | |
| 2008/0281260 A1 | 11/2008 | William et al. | |
| 2008/0308444 A1 | 12/2008 | McClain et al. | |
| 2009/0163342 A1 | 6/2009 | Kolberg et al. | |
| 2009/0197088 A1 | 8/2009 | Murata | |
| 2009/0275462 A1 | 11/2009 | Murata | |
| 2009/0325776 A1 | 12/2009 | Murata | |
| 2010/0035745 A1 | 2/2010 | Murata | |
| 2010/0047521 A1 | 2/2010 | Amin et al. | |
| 2010/0120603 A1 | 5/2010 | Morena et al. | |
| 2010/0255061 A1 | 10/2010 | de Juan, Jr. et al. | |
| 2010/0317506 A1 | 12/2010 | Fechner et al. | |
| 2011/0014475 A1 | 1/2011 | Murata | |
| 2011/0017297 A1 | 1/2011 | Aitken et al. | |
| 2011/0045960 A1 | 2/2011 | Fechner et al. | |
| 2011/0045961 A1 | 2/2011 | Dejneka et al. | |
| 2011/0062619 A1 | 3/2011 | Laine et al. | |
| 2011/0071012 A1 | 3/2011 | Kondo et al. | |
| 2011/0091704 A1 | 4/2011 | Akiba et al. | |
| 2011/0098172 A1 | 4/2011 | Brix | |
| 2011/0123832 A1 | 5/2011 | Matsumoto et al. | |
| 2011/0159318 A1 | 6/2011 | Endo et al. | |
| 2011/0177987 A1 | 7/2011 | Lenting et al. | |
| 2011/0274916 A1 | 11/2011 | Murata | |
| 2012/0199203 A1 | 8/2012 | Nishizawa et al. | |
| 2012/0208309 A1 | 8/2012 | Tsujimura et al. | |
| 2012/0297829 A1 | 11/2012 | Endo et al. | |
| 2013/0004758 A1 | 1/2013 | Dejneka et al. | |
| 2013/0011650 A1 | 1/2013 | Akiba et al. | |
| 2013/0101596 A1 | 4/2013 | DeMartino et al. | |
| 2013/0101764 A1 | 4/2013 | Schaut et al. | |
| 2013/0101766 A1 | 4/2013 | Danielson et al. | |
| 2013/0101853 A1 | 4/2013 | Drake et al. | |
| 2013/0196094 A1 | 8/2013 | Weeks et al. | |
| 2013/0196095 A1 | 8/2013 | Weeks et al. | |
| 2013/0196096 A1 | 8/2013 | Weeks et al. | |
| 2013/0196097 A1 | 8/2013 | Weeks et al. | |
| 2013/0202823 A1 | 8/2013 | Weeks et al. | |
| 2013/0213848 A1 | 8/2013 | Weeks et al. | |
| 2013/0216742 A1 | 8/2013 | DeMartino et al. | |
| 2014/0023865 A1 | 1/2014 | Comte et al. | |

FOREIGN PATENT DOCUMENTS

| | | |
|---|---|---|
| DE | 102004011009 A1 | 9/2005 |
| EP | 0515801 A1 | 12/1992 |
| EP | 1074521 A2 | 2/2001 |
| EP | 2031124 A1 | 3/2009 |
| EP | 2540682 A1 | 1/2013 |
| GB | 966731 A | 8/1964 |
| GB | 2335423 A | 9/1999 |
| IN | 231117 | 3/2009 |
| JP | 7223845 | 8/1995 |
| JP | 11314931 | 11/1999 |
| JP | 2000007372 A | 1/2000 |
| JP | 2001180969 A | 7/2001 |
| JP | 2001192239 A | 7/2001 |
| JP | 2001229526 A | 8/2001 |
| JP | 2001236634 A | 8/2001 |
| JP | 2002003241 A | 1/2002 |
| JP | 2002025762 A | 1/2002 |
| JP | 2002249340 A | 9/2002 |
| JP | 2004131314 A | 4/2004 |
| JP | 2008195602 A | 8/2008 |
| JP | 2010059038 A | 3/2010 |
| KR | 630309 | 5/2006 |
| RO | 83460 A2 | 3/1984 |
| SU | 990700 A1 | 1/1983 |
| WO | WO-2007025932 A2 | 3/2007 |
| WO | WO-2008050500 A1 | 5/2008 |
| WO | WO-2008143999 A1 | 11/2008 |
| WO | WO-2009002660 A2 | 12/2008 |
| WO | WO-2010084670 A1 | 7/2010 |
| WO | WO-2011049146 A1 | 4/2011 |
| WO | WO-2011069338 A1 | 6/2011 |
| WO | WO-2011103798 A1 | 9/2011 |
| WO | WO-2011103799 A1 | 9/2011 |
| WO | WO-2011145661 A1 | 11/2011 |
| WO | WO-2012026290 A1 | 3/2012 |

(56) References Cited

FOREIGN PATENT DOCUMENTS

| | | |
|---|---|---|
| WO | WO-2012124757 A1 | 9/2012 |
| WO | WO-2013063290 A1 | 5/2013 |

OTHER PUBLICATIONS

Barrowcliffe TW, et al., Anticoagulant activities of lung and mucous heparins. Thromb Res. Jan. 1978;12(1):27-36.
Beum PV et al., Three new assays for rituximab based on its immunological activity or antigenic properties: analyses of sera and plasmas of RTX-treated patients with chronic lymphocytic leukemia and other B cell lymphomas. J Immunol Methods. Jun. 2004;289(1-2):97-109.
Brunner KT et al. Quantitative assay of the lytic action of immune lymphoid cells on 51-Cr-labelled allogeneic target cells in vitro; inhibition by isoantibody and by drugs. Immunology. Feb. 1968;14(2):181-96.
Casset et al., "A peptide mimetic of an anti-CD4 monoclonal antibody by rational design", Biochem Biophys Res Commun. Jul. 18, 2003; vol. 307, No. 1, pp. 198-205.
Corrected Notice of Allowance mailed Sep. 11, 2013, relating to U.S. Appl. No. 13/660,394, filed Oct. 25, 2012.
Cortez-Retamozo et al., "Efficient cancer therapy with a nanobody-based conjugate", Cancer Research, Apr. 15, 2004, vol. 64, No. 8, pp. 2853-2857.
Cotes PM, et al., Bio-assay of erythropoietin in mice made polycythaemic by exposure to air at a reduced pressure. Nature. Sep. 9, 1961;191:1065-7.
Database WPI Week 198434 Thomsen Scientific, London, GB; AN 1984-211366 XP002690017.
Davis-Smyth T et al., The second immunoglobulin-like domain of the VEGF tyrosine kinase receptor Flt-1 determines ligand binding and may initiate a signal transduction cascade. EMBO J. Sep. 16, 1996;15(18):4919-27.
Drugs.com, Enbrel, May 28, 2010.
Drugs.com, Neulasta®, Sep. 13, 2010.
Fassina, G., "Complementary peptides as antibody mimetics for protein purification and assay", Immunomethods, Oct. 1994; vol. 5, No. 2, pp. 121-129.
Ferrara N, et al., Vascular endothelial growth factor is essential for corpus luteum angiogenesis. Nat Med. Mar. 1998;4(3):336-40.
Goldwasser E, et al., An assay for erythropoietin in vitro at the milliunit level. Endocrinology. Aug. 1975;97(2):315-23.
Hammond D, et al., Production, utilization and excretion of erythropoietin. I. Chronic anemias. II. Aplastic crisis. 3. Erythropoietic effects of normal plasma. Ann N Y Acad Sci. Mar. 29, 1968;149(1):516-27.
Holash J, et al., VEGF-Trap: a VEGF blocker with potent antitumor effects. Proc Natl Acad Sci U S A. Aug. 20, 2002;99(17):11393-8.
Horton RM et al., Engineering hybrid genes without the use of restriction enzymes: gene splicing by overlap extension. Gene. Apr. 15, 1989;77(1):61-8.
Humana Abbreviated Formulary List of Covered Drugs, 2010 Prescription Drug Guide.
International Search Report & Written Opinion relating to PCT/US2012/061940 filed Oct. 25, 2012; Mail Date: Jan. 30, 2013.
International Search Report & Written Opinion relating to PCT/US2012/061943 filed Oct. 25, 2012; Mail Date: Jan. 30, 2013.
International Search Report & Written Opinion relating to PCT/US2012/061946 filed Oct. 25, 2012; Mail Date: Jan. 30, 2013.
International Search Report & Written Opinion relating to PCT/US2012/061949 filed Oct. 25, 2012; Mail Date: Jan. 30, 2013.
International Search Report & Written Opinion relating to PCT/US2012/061953 filed Oct. 25, 2012; Mail Date: Jan. 30, 2013.
International Search Report & Written Opinion relating to PCT/US2012/061956 filed Oct. 25, 2012; Mail Date: Jan. 30, 2013.
International Search Report & Written Opinion relating to PCT/US2012/061958 filed Oct. 25, 2012; Mail Date: Jan. 30, 2013.
International Search Report & Written Opinion relating to PCT/US2013/048589 filed Jun. 28, 2013; Mail Date: Oct. 28, 2013.
International Search Report relating to PCT/US2012/061867; Mail Date: Jan. 30, 2013.
International Search Report relating to PCT/US2012/061939; Mail Date: Jan. 30, 2013.
IPRP & Written Opinion relating to PCT/US2012/061940 filed Oct. 25, 2012; Mail Date: May 8, 2014.
IPRP & Written Opinion relating to PCT/US2012/061943 filed Oct. 25, 2012; Mail Date: May 8, 2014.
IPRP & Written Opinion relating to PCT/US2012/061946 filed Oct. 25, 2012; Mail Date: May 8, 2014.
IPRP & Written Opinion relating to PCT/US2012/061949 filed Oct. 25, 2012; Mail Date: May 8, 2014.
IPRP & Written Opinion relating to PCT/US2012/061953 filed Oct. 25, 2012; Mail Date: May 8, 2014.
IPRP & Written Opinion relating to PCT/US2012/061956, filed Oct. 25, 2012; Mail date: May 8, 2014.
IPRP & Written Opinion relating to PCT/US2012/061958 filed Oct. 25, 2012; Mail Date: May 8, 2014.
Karch, AM, "2006 Lippincott's Nursing Drug Guide," Publisher: Lippincott Williams & Wilkins, ISBN: 1582554382, 2006.
Lane DA, et al., Anticoagulant activities of four unfractionated and fractionated heparins. Thromb Res. Feb. 1978;12(2):257-71.
Lichtlen P, Lam TT, Nork TM, Streit T, Urech DM. Relative contribution of VEGF and TNF-alpha in the cynomolgus laser-induced CNV model: comparing the efficacy of bevacizumab, adalimumab, and SBA105. Invest Ophthalmol Vis Sci. Sep. 2010;51(9):4738-45.
Machine translation CN101717189 Abstract.
Machine translation DE102004011009.
Machine translation JP2002025762 Abstract.
Machine translation JP2004131314.
Metcalf D. Clonal extinction of myelomonocytic leukemic cells by serum from mice injected with endotoxin. Int J Cancer. Feb. 15, 1980;25(2):225-33.
Murphy, D. B. and Davidson, M. W., "Differential Interference Contrast (DIC) Microscopy and Modulation Contrast" form Fundamentals of Light Microscopy and Electronic Imaging Published 2001, Publisher, Wiley, pp. 153-168.
Non-Final Office Action mailed Mar. 14, 2013, relating to U.S. Appl. No. 13/660,394, filed Oct. 25, 2012.
Notice of Allowance mailed Jun. 27, 2013, relating to U.S. Appl. No. 13/660,394, filed Oct. 25, 2012.
Pharmaceutical Drug Manufacturers, Erythropoietin Injection, Sep. 18, 2008.
Randle PJ., "Assay of plasma insulin activity by the rat-diaphragm method", British Medical Journal, May 29, 1954, vol. 1 (4873), pp. 1237-1240.
Reynolds et al., "Glass Delamination and Breakage", Bioprocess International, Dec. 1, 2011, vol. 9, No. 11, pp. 52-57.
Ribel U, Subcutaneous absorption of insulin analogues. In Frontiers in Insulin Pharmacology, Berger M, Gries FA (eds), Thieme Verlag, pp. 70-77 (1993).
Ribel U., et al., The pig as a model for subcutaneous insulin absorption in man. Serrano_Rios, M and Lefebvre, P.J. 891-896. 1985. Amsterdam; New York; Oxford, Elsevier Science Publishers. 1985 (Conference Proceeding).
Roche Consumer Medicine Information, Neupogen®, Feb. 3, 2010.
Saragovi et al., "Design and synthesis of a mimetic from an antibody complementarity-determining region", Science, Aug. 16, 1991, vol. 253, No. 5021, pp. 792-795.
Silva M, et al., Erythropoietin can induce the expression of bcl-x(L) through Stat5 in erythropoietin-dependent progenitor cell lines. J Biol Chem. Aug. 6, 1999;274(32):22165-9.
Teien AN, et al., Evaluation of an amidolytic heparin assay method: increased sensitivity by adding purified antithrombin III. Thromb Res. Mar. 1977;10(3):399-410.
Ternant D, et al., An enzyme-linked immunosorbent assay for therapeutic drug monitoring of infliximab. Ther Drug Monit. Apr. 2006;28(2):169-74.
U.S. Food and Drug Administration, Package Insert HUMIRA (adalimumab) Abbott Laboratories, 2010.

(56) References Cited

OTHER PUBLICATIONS

Ueda et al., "Age-dependent changes in phenotypes and candidate gene analysis in a polygenic animal model of Type II diabetes mellitus; NSY mouse" Diabetologia, Jul. 2000, vol. 43, Issue 7, pp. 932-938.

Wen, Zai-Qing et al., "Nondestructive detection of glass vial inner surface morphology with differential interference contrast microscopy", Journal of Pharmaceutical Sciences, Apr. 2012, vol. 101, Issue 4, pp. 1378-1384.

Yu L et al., Interaction between bevacizumab and murine VEGF-A: a reassessment. Invest Ophthalmol Vis Sci. Feb. 2008;49(2):522-7.

* cited by examiner

```
SEQUENCE LISTING

<160> NUMBER OF SEQ ID NOS: 8

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Thr Arg Arg
                20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
                20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
                20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
                20                  25                  30

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
            35
```

DELAMINATION RESISTANT PHARMACEUTICAL GLASS CONTAINERS CONTAINING ACTIVE PHARMACEUTICAL INGREDIENTS

CROSS REFERENCE TO RELATED APPLICATIONS

The present application claims priority to U.S. Provisional Patent Application Ser. No. 61/551,163, filed Oct. 25, 2011, entitled "Glass Compositions With Improved Chemical and Mechanical Durability," and U.S. Provisional Patent Application No. 61/656,998, filed Jun. 7, 2012, entitled "Delamination Resistant Glass Containers"; the entirety of each of which are hereby incorporated by reference herein.

SEQUENCE LISTING

The instant application contains a Sequence Listing which has been submitted in ASCII format via EFS-Web and is hereby incorporated by reference in its entirety. Said ASCII copy, created on Dec. 19, 2012, is named 12246711.txt and is 3,629 bytes in size.

FIELD OF THE INVENTION

The present specification generally relates to pharmaceutical containers and, more specifically, to chemically and mechanically durable pharmaceutical containers that are delamination resistant and formed, at least in part, of a glass composition.

BACKGROUND

The design of a packaged pharmaceutical composition generally seeks to provide an active pharmaceutical ingredient (API) in a suitable package that is convenient to use, that maintains the stability of the API over prolonged storage, and that ultimately allows for the delivery of efficacious, stable, active, nontoxic and nondegraded API.

Most packaged formulations are complex physico-chemical systems, through which the API is subject to deterioration by a variety of chemical, physical, and microbial reactions. Interactions between drugs, adjuvants, containers, and/or closures may occur, which can lead to the inactivation, decomposition and/or degradation of the API.

Historically, glass has been used as the preferred material for packaging pharmaceuticals because of its hermeticity, optical clarity and excellent chemical durability relative to other materials. Specifically, the glass used in pharmaceutical packaging must have adequate chemical durability so as not to affect the stability of the pharmaceutical compositions contained therein. Glasses having suitable chemical durability include those glass compositions within the ASTM standard 'Type 1B' glass compositions which have a proven history of chemical durability.

However, use of glass for such applications is limited by the mechanical performance of the glass. Specifically, in the pharmaceutical industry, glass breakage is a safety concern for the end user as the broken package and/or the contents of the package may injure the end user. Further, non-catastrophic breakage (i.e., when the glass cracks but does not break) may cause the contents to lose their sterility which, in turn, may result in costly product recalls.

One approach to improving the mechanical durability of the glass package is to thermally temper the glass package. Thermal tempering strengthens glass by inducing a surface compressive stress during rapid cooling after forming. This technique works well for glass articles with flat geometries (such as windows), glass articles with thicknesses >2 mm, and glass compositions with high thermal expansion. However, pharmaceutical glass packages typically have complex geometries (vial, tubular, ampoule, etc.), thin walls (~1-1.5 mm), and are produced from low expansion glasses (30-55× $10^{-7} K^{-1}$) making glass pharmaceutical packages unsuitable for strengthening by thermal tempering.

Chemical tempering also strengthens glass by the introduction of surface compressive stress. The stress is introduced by submerging the article in a molten salt bath. As ions from the glass are replaced by larger ions from the molten salt, a compressive stress is induced in the surface of the glass. The advantage of chemical tempering is that it can be used on complex geometries, thin samples, and is relatively insensitive to the thermal expansion characteristics of the glass substrate. However, glass compositions which exhibit a moderate susceptibility to chemical tempering generally exhibit poor chemical durability and vice-versa.

Finally, glass compositions commonly used in pharmaceutical packages, e.g., Type 1a and Type 1b glass, further suffer from a tendency for the interior surfaces of the pharmaceutical package to shed glass particulates or "delaminate" following exposure to pharmaceutical solutions. Such delamination often destabilizes the active pharmaceutical ingredient (API) present in the solution, thereby rendering the API therapeutically ineffective or unsuitable for therapeutic use.

Delamination has caused the recall of multiple drug products over the last few years (see, for example, Reynolds et al., (2011) BioProcess International 9(11) pp. 52-57). In response to the growing delamination problem, the U.S. Food and Drug Administration (FDA) has issued an advisory indicating that the presence of glass particulate in injectable drugs can pose a risk.

The advisory states that, "Where is potential for drugs administered intravenously that contain these fragments to cause embolic, thrombotic and other vascular events; and subcutaneously to the development of foreign body granuloma, local injections site reactions and increased immunogenicity."

Accordingly, a recognized need exists for alternative glass containers for packaging of pharmaceutical compositions which exhibit a reduced propensity to delaminate.

SUMMARY

The inventors of the instant application have developed delamination resistant pharmaceutical containers with improved mechanical properties that impart, for example, improved safety and efficacy on active pharmaceutical ingredients stored within the containers.

one aspect, the present invention is directed to a delamination resistant pharmaceutical container formed, at least in part, of a glass composition including from about 70 mol. % to about 80 mol. % $SiO_2$; from about 3 mol. % to about 13 mol. % alkaline earth oxide; X mol. % $Al_2O_3$; and Y mol. % alkali oxide, wherein the alkali oxide comprises $Na_2O$ in an amount greater than about 8 mol. %, a ratio of Y:X is greater than 1, and the glass composition is free of boron and compounds of boron.

In one embodiment, the $SiO_2$ is present in an amount less than or equal to 78 mol. %.

In one embodiment, the amount of the alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) that is less than or equal to 0.5. In a particular embodiment, the alkaline earth oxide includes from about 0.1 mol. % to less than or equal to about 1.0 mol. % CaO. In a particular embodiment, the alkaline earth oxide includes from about 3 mol. % to about 7 mol. % MgO.

In another embodiment, the alkali oxide includes greater than or equal to about 9 mol. % $Na_2O$ and less than or equal to about 15 mol. % $Na_2O$. In another embodiment, the alkali oxide further includes $K_2O$ in an amount less than or equal to about 3 mol. %. In a particular embodiment, the alkali oxide includes $K_2O$ in an amount greater than or equal to about 0.01 mol. % and less than or equal to about 1.0 mol. %.

In one embodiment, X is greater than or equal to about 2 mol. % and less than or equal to about 10 mol. %. In a particular embodiment, the ratio of Y:X is less than or equal to 2. In a particular embodiment, the ratio of Y:X is greater than or equal to 1.3 and less than or equal to 2.0.

In another embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 μm and a surface compressive stress greater than or equal to 250 MPa.

In another aspect, the present invention provides a delamination resistant pharmaceutical container formed, at least in part, of a glass composition including from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %.; and Y mol. % alkali oxide, wherein the alkali oxide includes $Na_2O$ in an amount greater than or equal to about 9 mol. % and less than or equal to about 15 mol. %, a ratio of Y:X is greater than 1, and the glass composition is free of boron and compounds of boron.

In a particular embodiment, the ratio of Y:X is less than or equal to about 2. In a particular embodiment, the ratio of Y:X is greater than or equal to about 1.3 and less than or equal to about 2.0.

In one embodiment, the alkaline earth oxide includes MgO and CaO and has a ratio (CaO (mol. %)/(CaO (mol. %)+MgO (mol. %))) less than or equal to 0.5.

In another embodiment, the alkali oxide includes $K_2O$ in an amount greater than or equal to about 0.01 mol. % and less than or equal to about 1.0 mol. %.

In another aspect, the present invention provides a delamination resistant pharmaceutical container formed, at least in part, of a glass composition including from about 68 mol. % to about 80 mol. % $SiO_2$; from about 3 mol. % to about 13 mol. % alkaline earth oxide; X mol. % $Al_2O_3$; Y mol. % alkali oxide, wherein the alkali oxide includes $Na_2O$ in an amount greater than about 8 mol. %; and $B_2O_3$, wherein a ratio ($B_2O_3$ (mol. %)/(Y mol. %–X mol. %) is greater than 0 and less than 0.3, and a ratio of Y:X is greater than 1.

In one embodiment, the amount of $SiO_2$ is greater than or equal to about 70 mol. %.

In one embodiment, the amount of alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) less than or equal to 0.5. In a particular embodiment, the alkaline earth oxide includes CaO in an amount greater than or equal to about 0.1 mol. % and less than or equal to about 1.0 mol. %. In a particular embodiment, the alkaline earth oxide includes from about 3 mol. % to about 7 mol. % MgO.

In one embodiment, the alkali oxide is greater than or equal to about 9 mol. % $Na_2O$ and less than or equal to about 15 mol. % $Na_2O$. In a particular embodiment, the alkali oxide further includes $K_2O$ in a concentration less than or equal to about 3 mol. %. In another embodiment, the alkali oxide further includes $K_2O$ in a concentration greater than or equal to about 0.01 mol. % and less than or equal to about 1.0 mol. %.

In another embodiment, the pharmaceutical container has a ratio ($B_2O_3$ (mol. %)/(Y mol. %–X mol. %) less than 0.2. In a particular embodiment, the amount of $B_2O_3$ is less than or equal to about 4.0 mol. %. In another embodiment, the amount of $B_2O_3$ is greater than or equal to about 0.01 mol. %.

In one embodiment, X is greater than or equal to about 2 mol. % and less than or equal to about 10 mol. %. In a particular embodiment, the ratio of Y:X is less than or equal to 2. In another embodiment, the ratio of Y:X is greater than 1.3.

In one embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 μm and a surface compressive stress greater than or equal to 250 MPa.

In one embodiment of any of the foregoing aspects of the invention, the pharmaceutical container further includes a pharmaceutical composition having an active pharmaceutical ingredient. In a particular embodiment, the pharmaceutical composition includes a citrate or phosphate buffer, for example, sodium citrate, SSC, monosodium phosphate or disodium phosphate. Alternatively or in addition, the pharmaceutical composition has a pH between about 7 and about 11, between about 7 and about 10, between about 7 and about 9, or between about 7 and about 8.

In one embodiment, the pharmaceutical container comprises a vial, cartridge, syringe, ampoule, bottle, flask, or vacutainer. In another embodiment, the container is delamination resistant. In an exemplary embodiment, the container has a delamination factor of 1.

In one embodiment, the pharmaceutical containers provided herein further comprise a pharmaceutical composition comprising an active pharmaceutical ingredient.

In one embodiment, the active pharmaceutical ingredient is an antidiabetic. Exemplary antidiabetics include insulin aspart, insulin degludec, insulin glargine recombinant, dulaglutide, lixisenatide, hyaluronidase (human), insulin, insulin degludec, liraglutide, insulin glargine, lixisenatide, albiglutide, insulin glargine recombinant, insulin lispro recombinant, insulin aspart, insulin (human), insulin detemir, exenatide synthetic, and Liraglutide.

In another embodiment, the active pharmaceutical ingredient is an antineoplastic, for example an antineoplastic MAb. Exemplary antineoplastics include Bavituximab, Onartuzumab, yttrium Y-90 clivatuzumab tetraxetan, obinutuzumab, cixutumumab, necitumumab, pertuzumab, brentuximab vedotin, nivolumab, trastuzumab emtansine, siltuximab, elotuzumab, ramucirumab, trastuzumab emtansin, Ipilimumab, Rituximab, Trastuzumab, Pertuzumab, and bevacizumab.

In one embodiment, the active pharmaceutical ingredient is an antirheumatic. Exemplary antirheumatics include tabalumab, sarilumab, Tocilizumab, Infliximab, Etanercept, Abatacept, certolizumab pegol, Infliximab, Golimumab, and Adalimumab.

In one embodiment, the active pharmaceutical ingredient is an antibacterial. Exemplary antibacterials include ceftolozane sulfate, tazobactam sodium, ceftaroline fosamil, brilacidin, brilacidin, and tedizolid phosphate.

In one embodiment, the active pharmaceutical ingredient is a cytostatic. Exemplary cytostatics include CT-107, ganetespib, CUDC-101, REOLYSIN®, AEZS-108, velimogene aliplasmid, imetelstat sodium, algenpantucel-L, retaspimycin hydrochloride, astuprotimut-R, vosaroxin, BIOVAXID®, iniparib, Bortezomib, and carfilzomib.

In one embodiment, the active pharmaceutical ingredient is a vaccine. Exemplary vaccines include meningococcal B vaccine, influenza vaccine, herpes zoster vaccine, hepatitis B vaccine, human papillomavirus (HPV) vaccine, pneumococcal vaccine, DTPw, influenza vaccine, hepatitis A and B vaccine, DTP, and hepatitis B and polio vaccine.

In one embodiment, the active pharmaceutical ingredient is an immunosuppressant. Exemplary immunosuppresants include epratuzumab, eritoran tetrasodium, blisibimod, and ustekinumab.

In one embodiment, the active pharmaceutical ingredient is an anti-fibrinolytic. Exemplary anti-fibrinolytics include turoctocog alfa, vonicog alfa, factor VIII, eptacog alfa, and octocog alfa.

In one embodiment, the active pharmaceutical ingredient is an eye preparation. Exemplary eye preparations include Ocriplasmin, Ranibizumab, Aflibercept, and Ranibizumab.

In one embodiment, the active pharmaceutical ingredient is a MS therapeutic. Exemplary MS therapeutics include Alemtuzumab, ocrelizumab, daclizumab, peginterferon beta-1a, interferon beta-1a, Natalizumab, glatiramer acetate, and interferon beta-1a.

In one embodiment, the active pharmaceutical ingredient is a bone calcium regulator. Exemplary bone calcium regulators include romosozumab, Denosumab, and recombinant human teriparatide.

In one embodiment, the active pharmaceutical ingredient is an anti-coagulant. Exemplary anti-coagulants include semuloparin sodium, otamixaban, and enoxaparin sodium.

In one embodiment, the active pharmaceutical ingredient is an anti-psychotic. Exemplary anti-psychotics include aripiprazole.

In one embodiment, the active pharmaceutical ingredient is an anti-metabolite. Exemplary anti-metabolites include gemcitabine elaidate.

In one embodiment, the active pharmaceutical ingredient is a radiopharmaceutical. Exemplary radiopharmaceuticals include radium Ra-223 chloride.

In one embodiment, the active pharmaceutical ingredient is an immunostimulant. Exemplary immunostimulants include Pegfilgrastim.

In one embodiment, the active pharmaceutical ingredient is a cytotoxic antibiotic. Exemplary cytotoxic antibiotic include doxorubicin hydrochloride.

In one embodiment, the active pharmaceutical ingredient is a cerebral and peripheral vasotherapeutic. Exemplary cerebral and peripheral vasotherapeutics include defibrotide.

In one embodiment, the active pharmaceutical ingredient is a musculoskeletal agent. Exemplary musculoskeletal agents include Drisapersen, eteplirsen, and asfotase alfa.

In one embodiment, the active pharmaceutical ingredient is a nootropic. Exemplary nootropic include solanezumab.

In one embodiment, the active pharmaceutical ingredient is a CNS drug. Exemplary CNS drugs include neural stem cells.

In one embodiment, the active pharmaceutical ingredient is a dermatological. Exemplary dermatologicals include secukinumab.

In one embodiment, the active pharmaceutical ingredient is an angiotensin II antagonist. Exemplary angiotensin II antagonist include serelaxin.

In one embodiment, the active pharmaceutical ingredient is an anti-spasmodic or anti-cholinergic. Exemplary anti-spasmodic or anti-cholinergics include teduglutide.

In one embodiment, the active pharmaceutical ingredient is an interferon. Exemplary interferons include peginterferon lambda-1a.

In one embodiment, the active pharmaceutical ingredient is an anti-anaemic. Exemplary anti-anaemics include ferric pyrophosphate and arbepoetin alfa.

In one embodiment, the active pharmaceutical ingredient is an anti-psoriasis agent. Exemplary anti-psoriasis agents include ixekizumab.

In one embodiment, the active pharmaceutical ingredient is an anti-hyperlipidaemic. Exemplary anti-hyperlipidaemics include alirocumab.

In one embodiment, the active pharmaceutical ingredient is a cardiac therapeutic. Exemplary cardiac therapeutics include cenderitide.

In one embodiment, the active pharmaceutical ingredient is an alkylating agent. Exemplary alkylating agents include palifosfamide.

In one embodiment, the active pharmaceutical ingredient is a bronchodilator. Exemplary bronchodilators include lebrikizumab.

In one embodiment, the active pharmaceutical ingredient is a gastro-intestinal anti-inflammatory. Exemplary gastro-intestinal anti-inflammatories include vedolizumab.

In one embodiment, the active pharmaceutical ingredient is a growth hormone.

In one embodiment, the active pharmaceutical ingredient is a hormone preparation. Exemplary hormone preparations include parathyroid hormone 1-84.

In one embodiment, the active pharmaceutical ingredient is a non-narcotic analgesic. Exemplary non-narcotic analgesics include fulranumab.

In one embodiment, the active pharmaceutical ingredient is a diagnostic imaging agent. Exemplary diagnostic imaging agents include Minretumomab.

In one embodiment, the active pharmaceutical ingredient is a haematological. Exemplary haematologicals include Eculizumab.

In one embodiment, the active pharmaceutical ingredient is a peripheral muscle relaxant. Exemplary peripheral muscle relaxants include botulinum toxin type A.

In one embodiment, the active pharmaceutical ingredient is an interferon. Exemplary interferons include peginterferon alfa-2a.

In one embodiment, the active pharmaceutical ingredient is elosulfase alfa, Protectan CBLB502, HGT-1410, HGT 1110, or sebelipase alfa.

In one embodiment, the pharmaceutical composition comprises a citrate or phosphate buffer. In one embodiment, the buffer is selected from the group consisting of sodium citrate, SSC, monosodium phosphate and disodium phosphate.

In one embodiment, the pharmaceutical composition comprises a pH between about 7 and about 11, between about 7 and about 10, between about 7 and about 9, or between about 7 and about 8.

In one embodiment, the pharmaceutical composition comprises delamination resistant pharmaceutical container comprising a glass composition comprising:

from about 68 mol. % to about 80 mol. % $SiO_2$;
from about 3 mol. % to about 13 mol. % alkaline earth oxide;
X mol. % $Al_2O_3$;
Y mol. % alkali oxide, wherein the alkali oxide comprises $Na_2O$ in an amount greater than about 8 mol. %; and
$B_2O_3$, wherein a ratio ($B_2O_3$ (mol. %)/(Y mol. %–X mol. %) is greater than 0 and less than 0.3, and a ratio of Y:X is greater than 1; and wherein the container further comprises a pharmaceutical composition selected from the group consisting of the pharmaceutical compositions set forth in Table 1 or 6.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
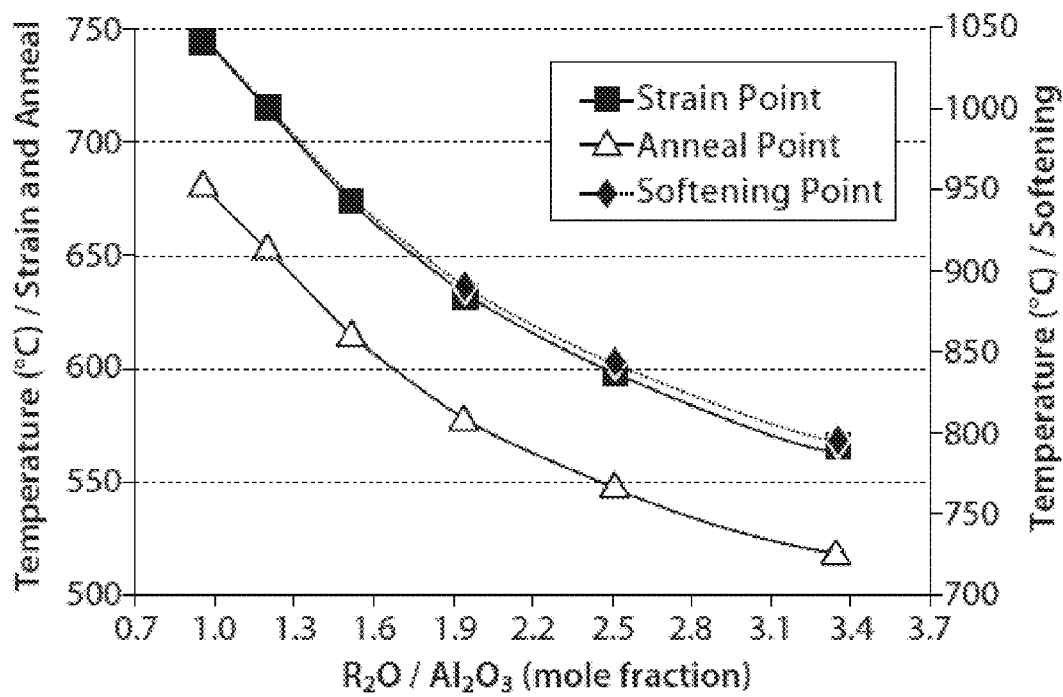
FIG. 1 graphically depicts the relationship between the ratio of alkali oxides to alumina (x-axis) and the strain point, annealing point, and softening point (y-axes) of inventive and comparative glass compositions.

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage, maintenance and/or delivery of therapeutically efficacious pharmaceutical compositions and, in particular pharmaceutical solutions comprising active pharmaceutical ingredients.

Conventional glass containers or glass packages for containing pharmaceutical compositions are generally formed from glass compositions which are known to exhibit chemical durability and low thermal expansion, such as alkali borosilicate glasses. While alkali borosilicate glasses exhibit good chemical durability, container manufacturers have sporadically observed silica-rich glass flakes dispersed in the solution contained in the glass containers as a result of delamination, particularly when the solution has been stored in direct contact with the glass surface for long time periods (months to years).

Delamination refers to a phenomenon in which glass particles are released from the surface of the glass following a series of leaching, corrosion, and/or weathering reactions. In general, the glass particles are silica-rich flakes of glass which originate from the interior surface of the package as a result of the leaching of modifier ions into a solution contained within the package. These flakes may generally be from about 1 nm to 2 µm thick with a width greater than about 50 µm.

It has heretofore been hypothesized that delamination is due to the phase separation which occurs in alkali borosilicate glasses when the glass is exposed to the elevated temperatures used for reforming the glass into a container shape.

However, it is now believed that the delamination of the silica-rich glass flakes from the interior surfaces of the glass containers is due to the compositional characteristics of the glass container in its as-formed condition. Specifically, the high silica content of alkali borosilicate glasses increases the melting temperature of the glass. However, the alkali and borate components in the glass composition melt and/or vaporize at much lower temperatures. In particular, the borate species in the glass are highly volatile and evaporate from the surface of the glass at the high temperatures necessary to melt and form the glass.

Specifically, glass stock is reformed into glass containers at high temperatures and in direct flames. The high temperatures cause the volatile borate species to evaporate from portions of the surface of the glass. When this evaporation occurs within the interior volume of the glass container, the volatilized borate species are re-deposited in other areas of the glass causing compositional heterogeneities in the glass container, particularly with respect to the bulk of the glass container. For example, as one end of a glass tube is closed to form the bottom or floor of the container, borate species may evaporate from the bottom portion of the tube and be re-deposited elsewhere in the tube. As a result, the areas of the container exposed to higher temperatures have silica-rich surfaces. Other areas of the container which are amenable to boron deposition may have a silica-rich surface with a boron-rich layer below the surface. Areas amenable to boron deposition are at a temperature greater than the anneal point of the glass composition but less than the hottest temperature the glass is subjected to during reformation when the boron is incorporated into the surface of the glass. Solutions contained in the container may leach the boron from the boron-rich layer. As the boron-rich layer is leached from the glass, the silica-rich surface begins to spall, shedding silica-rich flakes into the solution.

DEFINITIONS

The term "softening point," as used herein, refers to the temperature at which the viscosity of the glass composition is $1 \times 10^{7.6}$ poise.

The term "annealing point," as used herein, refers to the temperature at which the viscosity of the glass composition is $1 \times 10^{13}$ poise.

The terms "strain point" and "$T_{strain}$" as used herein, refers to the temperature at which the viscosity of the glass composition is $3 \times 10^{14}$ poise.

The term "CTE," as used herein, refers to the coefficient of thermal expansion of the glass composition over a temperature range from about room temperature (RT) to about 300° C.

In the embodiments of the glass compositions described herein, the concentrations of constituent components (e.g., $SiO_2$, $Al_2O_3$, and the like) are specified in mole percent (mol. %) on an oxide basis, unless otherwise specified.

The terms "free" and "substantially free," when used to describe the concentration and/or absence of a particular constituent component in a glass composition, means that the constituent component is not intentionally added to the glass composition. However, the glass composition may contain traces of the constituent component as a contaminant or tramp in amounts of less than 0.01 mol. %.

The term "chemical durability," as used herein, refers to the ability of the glass composition to resist degradation upon exposure to specified chemical conditions. Specifically, the chemical durability of the glass compositions described herein was assessed according to three established material testing standards: DIN 12116 dated March 2001 and entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; and ISO 720: 1985 entitled "Glass—Hydrolytic resistance of glass grains at 121 degrees C.—Method of test and classification." The chemical durability of the glass may also be assessed according to ISO 719:1985 "Glass—Hydrolytic resistance of glass grains at 98 degrees C.—Method of test and classification," in addition to the above referenced standards. The ISO 719 standard is a less rigorous version of the ISO 720 standard and, as such, it is believed that a glass which meets a specified classification of the ISO 720 standard will also meet the corresponding classification of the ISO 719 standard. The classifications associated with each standard are described in further detail herein.

Glass Compositions

Reference will now be made in detail to various embodiments of pharmaceutical containers formed, at least in part, of glass compositions which exhibit improved chemical and mechanical durability and, in particular, improved resistance to delamination. The glass compositions may also be chemically strengthened thereby imparting increased mechanical durability to the glass. The glass compositions described herein generally comprise silica ($SiO_2$), alumina ($Al_2O_3$), alkaline earth oxides (such as MgO and/or CaO), and alkali oxides (such as $Na_2O$ and/or $K_2O$) in amounts which impart chemical durability to the glass composition. Moreover, the alkali oxides present in the glass compositions facilitate chemically strengthening the glass compositions by ion exchange. Various embodiments of the glass compositions will be described herein and further illustrated with reference to specific examples.

The glass compositions described herein are alkali aluminosilicate glass compositions which generally include a combination of $SiO_2$, $Al_2O_3$, at least one alkaline earth oxide, and one or more alkali oxides, such as $Na_2O$ and/or $K_2O$. In some embodiments, the glass compositions may be free from boron and compounds containing boron. The combination of these components enables a glass composition which is resistant to chemical degradation and is also suitable for chemical strengthening by ion exchange. In some embodiments the glass compositions may further comprise minor amounts of one or more additional oxides such as, for example, $SnO_2$, $ZrO_2$, ZnO, $TiO_2$, $As_2O_3$ or the like. These components may be added as fining agents and/or to further enhance the chemical durability of the glass composition.

In the embodiments of the glass compositions described herein $SiO_2$ is the largest constituent of the composition and, as such, is the primary constituent of the resulting glass network. $SiO_2$ enhances the chemical durability of the glass and, in particular, the resistance of the glass composition to decomposition in acid and the resistance of the glass composition to decomposition in water. Accordingly, a high $SiO_2$ concentration is generally desired. However, if the content of $SiO_2$ is too high, the formability of the glass may be diminished as higher concentrations of $SiO_2$ increase the difficulty of melting the glass which, in turn, adversely impacts the formability of the glass. In the embodiments described herein, the glass composition generally comprises $SiO_2$ in an amount greater than or equal to 67 mol. % and less than or equal to about 80 mol. % or even less than or equal to 78 mol. %. In some embodiments, the amount of $SiO_2$ in the glass composition may be greater than about 68 mol. %, greater than about 69 mol. % or even greater than about 70 mol. %. In some other embodiments, the amount of $SiO_2$ in the glass composition may be greater than 72 mol. %, greater than 73 mol. % or even greater than 74 mol. %. For example, in some embodiments, the glass composition may include from about 68 mol. % to about 80 mol. % or even to about 78 mol. % $SiO_2$. In some other embodiments the glass composition may include from about 69 mol. % to about 80 mol. % or even to about 78 mol. % $SiO_2$. In some other embodiments the glass composition may include from about 70 mol. % to about 80 mol. % or even to about 78 mol. % $SiO_2$. In still other embodiments, the glass composition comprises $SiO_2$ in an amount greater than or equal to 70 mol. % and less than or equal to 78 mol. %. In some embodiments, $SiO_2$ may be present in the glass composition in an amount from about 72 mol. % to about 78 mol. %. In some other embodiments, $SiO_2$ may be present in the glass composition in an amount from about 73 mol. % to about 78 mol. %. In other embodiments, $SiO_2$ may be present in the glass composition in an amount from about 74 mol. % to about 78 mol. %. In still other embodiments, $SiO_2$ may be present in the glass composition in an amount from about 70 mol. % to about 76 mol. %.

The glass compositions described herein further include $Al_2O_3$. $Al_2O_3$, in conjunction with alkali oxides present in the glass compositions such as $Na_2O$ or the like, improves the susceptibility of the glass to ion exchange strengthening. In the embodiments described herein, $Al_2O_3$ is present in the glass compositions in X mol. % while the alkali oxides are present in the glass composition in Y mol. %. The ratio Y:X in the glass compositions described herein is greater than 1 in order to facilitate the aforementioned susceptibility to ion exchange strengthening. Specifically, the diffusion coefficient or diffusivity D of the glass composition relates to the rate at which alkali ions penetrate into the glass surface during ion exchange. Glasses which have a ratio Y:X greater than about 0.9 or even greater than about 1 have a greater diffusivity than glasses which have a ratio Y:X less than 0.9. Glasses in which the alkali ions have a greater diffusivity can obtain a greater depth of layer for a given ion exchange time and ion exchange temperature than glasses in which the alkali ions have a lower diffusivity. Moreover, as the ratio of Y:X increases, the strain point, anneal point, and softening point of the glass decrease, such that the glass is more readily formable. In addition, for a given ion exchange time and ion exchange temperature, it has been found that compressive stresses induced in glasses which have a ratio Y:X greater than about 0.9 and less than or equal to 2 are generally greater than those generated in glasses in which the ratio Y:X is less than 0.9 or greater than 2. Accordingly, in some embodiments, the ratio of Y:X is greater than 0.9 or even greater than 1. In some embodiments, the ratio of Y:X is greater than 0.9, or even greater than 1, and less than or equal to about 2. In still other embodiments, the ratio of Y:X may be greater than or equal to about 1.3 and less than or equal to about 2.0 in order to maximize the amount of compressive stress induced in the glass for a specified ion exchange time and a specified ion exchange temperature.

However, if the amount of $Al_2O_3$ in the glass composition is too high, the resistance of the glass composition to acid attack is diminished. Accordingly, the glass compositions described herein generally include $Al_2O_3$ in an amount greater than or equal to about 2 mol. % and less than or equal to about 10 mol. %. In some embodiments, the amount of $Al_2O_3$ in the glass composition is greater than or equal to about 4 mol. % and less than or equal to about 8 mol. %. In some other embodiments, the amount of $Al_2O_3$ in the glass composition is greater than or equal to about 5 mol. % to less than or equal to about 7 mol. %. In some other embodiments, the amount of $Al_2O_3$ in the glass composition is greater than or equal to about 6 mol. % to less than or equal to about 8 mol. %. In still other embodiments, the amount of $Al_2O_3$ in the glass composition is greater than or equal to about 5 mol. % to less than or equal to about 6 mol. %.

The glass compositions also include one or more alkali oxides such as $Na_2O$ and/or $K_2O$. The alkali oxides facilitate the ion exchangeability of the glass composition and, as such, facilitate chemically strengthening the glass. The alkali oxide may include one or more of $Na_2O$ and $K_2O$. The alkali oxides are generally present in the glass composition in a total concentration of Y mol. %. In some embodiments described herein, Y may be greater than about 2 mol. % and less than or equal to about 18 mol. %. In some other embodiments, Y may be greater than about 8 mol. %, greater than about 9 mol. %, greater than about 10 mol. % or even greater than about 11 mol. %. For example, in some embodiments described herein Y is greater than or equal to about 8 mol. % and less than or equal to about 18 mol. %. In still other embodiments, Y may be greater than or equal to about 9 mol. % and less than or equal to about 14 mol. %.

The ion exchangeability of the glass composition is primarily imparted to the glass composition by the amount of the alkali oxide $Na_2O$ initially present in the glass composition prior to ion exchange. Accordingly, in the embodiments of the glass compositions described herein, the alkali oxide present in the glass composition includes at least $Na_2O$. Specifically, in order to achieve the desired compressive strength and depth of layer in the glass composition upon ion exchange strengthening, the glass compositions include $Na_2O$ in an amount from about 2 mol. % to about 15 mol. % based on the molecular weight of the glass composition. In some embodiments the glass composition includes at least about 8 mol. % of $Na_2O$ based on the molecular weight of the glass composition. For example, the concentration of $Na_2O$ may be greater than 9 mol. %, greater than 10 mol. % or even greater than 11 mol. %. In some embodiments, the concentration of $Na_2O$ may be greater than or equal to 9 mol. % or even greater than or equal to 10 mol. %. For example, in some embodiments the glass composition may include $Na_2O$ in an amount greater than or equal to about 9 mol. % and less than or equal to about 15 mol. % or even greater than or equal to about 9 mol. % and less than or equal to 13 mol. %.

As noted above, the alkali oxide in the glass composition may further include $K_2O$. The amount of $K_2O$ present in the glass composition also relates to the ion exchangeability of the glass composition. Specifically, as the amount of $K_2O$ present in the glass composition increases, the compressive stress obtainable through ion exchange decreases as a result of the exchange of potassium and sodium ions. Accordingly, it is desirable to limit the amount of $K_2O$ present in the glass composition. In some embodiments, the amount of $K_2O$ is greater than or equal to 0 mol. % and less than or equal to 3 mol. %. In some embodiments, the amount of $K_2O$ is less or equal to 2 mol. % or even less than or equal to 1.0 mol. %. In embodiments where the glass composition includes $K_2O$, the $K_2O$ may be present in a concentration greater than or equal to about 0.01 mol. % and less than or equal to about 3.0 mol. % or even greater than or equal to about 0.01 mol. % and less than or equal to about 2.0 mol. %. In some embodiments, the amount of $K_2O$ present in the glass composition is greater than or equal to about 0.01 mol. % and less than or equal to about 1.0 mol. %. Accordingly, it should be understood that $K_2O$ need not be present in the glass composition. However, when $K_2O$ is included in the glass composition, the amount of $K_2O$ is generally less than about 3 mol. % based on the molecular weight of the glass composition.

The alkaline earth oxides present in the composition improve the meltability of the glass batch materials and increase the chemical durability of the glass composition. In the glass compositions described herein, the total mol. % of alkaline earth oxides present in the glass compositions is generally less than the total mol. % of alkali oxides present in the glass compositions in order to improve the ion exchangeability of the glass composition. In the embodiments described herein, the glass compositions generally include from about 3 mol. % to about 13 mol. % of alkaline earth oxide. In some of these embodiments, the amount of alkaline earth oxide in the glass composition may be from about 4 mol. % to about 8 mol. % or even from about 4 mol. % to about 7 mol. %.

The alkaline earth oxide in the glass composition may include MgO, CaO, SrO, BaO or combinations thereof. In some embodiments, the alkaline earth oxide includes MgO, CaO or combinations thereof. For example, in the embodiments described herein the alkaline earth oxide includes MgO. MgO is present in the glass composition in an amount which is greater than or equal to about 3 mol. % and less than or equal to about 8 mol. % MgO. In some embodiments, MgO may be present in the glass composition in an amount which is greater than or equal to about 3 mol. % and less than or equal to about 7 mol. % or even greater than or equal to 4 mol. % and less than or equal to about 7 mol. % by molecular weight of the glass composition.

In some embodiments, the alkaline earth oxide may further include CaO. In these embodiments CaO is present in the glass composition in an amount from about 0 mol. % to less than or equal to 6 mol. % by molecular weight of the glass composition. For example, the amount of CaO present in the glass composition may be less than or equal to 5 mol. %, less than or equal to 4 mol. %, less than or equal to 3 mol. %, or even less than or equal to 2 mol. %. In some of these embodiments, CaO may be present in the glass composition in an amount greater than or equal to about 0.1 mol. % and less than or equal to about 1.0 mol. %. For example, CaO may be present in the glass composition in an amount greater than or equal to about 0.2 mol. % and less than or equal to about 0.7 mol. % or even in an amount greater than or equal to about 0.3 mol. % and less than or equal to about 0.6 mol. %.

In the embodiments described herein, the glass compositions are generally rich in MgO, (i.e., the concentration of MgO in the glass composition is greater than the concentration of the other alkaline earth oxides in the glass composition including, without limitation, CaO). Forming the glass composition such that the glass composition is MgO-rich improves the hydrolytic resistance of the resultant glass, particularly following ion exchange strengthening. Moreover, glass compositions which are MgO-rich generally exhibit improved ion exchange performance relative to glass compositions which are rich in other alkaline earth oxides. Specifically, glasses formed from MgO-rich glass compositions generally have a greater diffusivity than glass compositions which are rich in other alkaline earth oxides, such as CaO. The greater diffusivity enables the formation of a deeper depth of layer in the glass. MgO-rich glass compositions also enable a higher compressive stress to be achieved in the surface of the glass compared to glass compositions which are rich in other alkaline earth oxides such as CaO. In addition, it is generally understood that as the ion exchange process proceeds and alkali ions penetrate more deeply into the glass, the maximum compressive stress achieved at the surface of the glass may decrease with time. However, glasses formed from glass compositions which are MgO-rich exhibit a lower reduction in compressive stress than glasses formed from glass compositions that are CaO-rich or rich in other alkaline earth oxides (i.e., glasses which are MgO-poor). Thus, MgO-rich glass compositions enable glasses which have higher compressive stress at the surface and greater depths of layer than glasses which are rich in other alkaline earth oxides.

In order to fully realize the benefits of MgO in the glass compositions described herein, it has been determined that the ratio of the concentration of CaO to the sum of the concentration of CaO and the concentration of MgO in mol. % (i.e., (CaO/(CaO+MgO)) should be minimized Specifically, it has been determined that (CaO/(CaO+MgO)) should be less than or equal to 0.5. In some embodiments (CaO/(CaO+MgO)) is less than or equal to 0.3 or even less than or equal to 0.2. In some other embodiments (CaO/(CaO+MgO)) may even be less than or equal to 0.1.

Boron oxide ($B_2O_3$) is a flux which may be added to glass compositions to reduce the viscosity at a given temperature (e.g., the strain, anneal and softening temperatures) thereby improving the formability of the glass. However, it has been found that additions of boron significantly decrease the diffusivity of sodium and potassium ions in the glass composition which, in turn, adversely impacts the ion exchange performance of the resultant glass. In particular, it has been found that additions of boron significantly increase the time required to achieve a given depth of layer relative to glass compositions which are boron free. Accordingly, in some embodiments described herein, the amount of boron added to the glass composition is minimized in order to improve the ion exchange performance of the glass composition.

For example, it has been determined that the impact of boron on the ion exchange performance of a glass composition can be mitigated by controlling the ratio of the concentration of $B_2O_3$ to the difference between the total concentration of the alkali oxides (i.e., $R_2O$, where R is the alkali metals) and alumina (i.e., $B_2O_3$ (mol. %)/($R_2O$ (mol. %)-$Al_2O_3$ (mol. %)). In particular, it has been determined that when the ratio of $B_2O_3/(R_2O—Al_2O_3)$ is greater than or equal to about 0 and less than about 0.3 or even less than about 0.2, the diffusivities of alkali oxides in the glass compositions are not diminished and, as such, the ion exchange performance of the glass composition is maintained. Accordingly, in some embodiments, the ratio of $B_2O_3/(R_2O—Al_2O_3)$ is greater than 0 and less than or equal to 0.3. In some of these embodiments, the ratio of $B_2O_3/(R_2O—Al_2O_3)$ is greater than 0 and less than or equal to 0.2. In some embodiments, the ratio of $B_2O_3/(R_2O—Al_2O_3)$ is greater than 0 and less than or equal to 0.15 or even less than or equal to 0.1. In some other embodiments, the ratio of $B_2O_3/(R_2O—Al_2O_3)$ may be greater than 0 and less than or equal to 0.05. Maintaining the ratio $B_2O_3/(R_2O—Al_2O_3)$ to be less than or equal to 0.3 or even less than or equal to 0.2 permits the inclusion of $B_2O_3$ to lower the strain point, anneal point and softening point of the glass composition without the $B_2O_3$ adversely impacting the ion exchange performance of the glass.

In the embodiments described herein, the concentration of $B_2O_3$ in the glass composition is generally less than or equal to about 4 mol. %, less than or equal to about 3 mol. %, less than or equal to about 2 mol. %, or even less than or equal to 1 mol. %. For example, in embodiments where $B_2O_3$ is present in the glass composition, the concentration of $B_2O_3$ may be greater than about 0.01 mol. % and less than or equal to 4 mol. %. In some of these embodiments, the concentration of $B_2O_3$ may be greater than about 0.01 mol. % and less than or equal to 3 mol. % In some embodiments, the $B_2O_3$ may be present in an amount greater than or equal to about 0.01 mol. % and less than or equal to 2 mol. %, or even less than or equal to 1.5 mol. %. Alternatively, the $B_2O_3$ may be present in an amount greater than or equal to about 1 mol. % and less than or equal to 4 mol. %, greater than or equal to about 1 mol. % and less than or equal to 3 mol. % or even greater than or equal to about 1 mol. % and less than or equal to 2 mol. %. In some of these embodiments, the concentration of $B_2O_3$ may be greater than or equal to about 0.1 mol. % and less than or equal to 1.0 mol. %.

While in some embodiments the concentration of $B_2O_3$ in the glass composition is minimized to improve the forming properties of the glass without detracting from the ion exchange performance of the glass, in some other embodiments the glass compositions are free from boron and compounds of boron such as $B_2O_3$. Specifically, it has been determined that forming the glass composition without boron or compounds of boron improves the ion exchangeability of the glass compositions by reducing the process time and/or temperature required to achieve a specific value of compressive stress and/or depth of layer.

In some embodiments of the glass compositions described herein, the glass compositions are free from phosphorous and compounds containing phosphorous including, without limitation, $P_2O_5$. Specifically, it has been determined that formulating the glass composition without phosphorous or compounds of phosphorous increases the chemical durability of the glass composition.

In addition to the $SiO_2$, $Al_2O_3$, alkali oxides and alkaline earth oxides, the glass compositions described herein may optionally further comprise one or more fining agents such as, for example, $SnO_2$, $As_2O_3$, and/or $Cl^-$ (from NaCl or the like). When a fining agent is present in the glass composition, the fining agent may be present in an amount less than or equal to about 1 mol. % or even less than or equal to about 0.4 mol. %. For example, in some embodiments the glass composition may include $SnO_2$ as a fining agent. In these embodiments $SnO_2$ may be present in the glass composition in an amount greater than about 0 mol. % and less than or equal to about 1 mol. % or even an amount greater than or equal to about 0.01 mol. % and less than or equal to about 0.30 mol. %.

Moreover, the glass compositions described herein may comprise one or more additional metal oxides to further improve the chemical durability of the glass composition. For example, the glass composition may further include ZnO, $TiO_2$, or $ZrO_2$, each of which further improves the resistance of the glass composition to chemical attack. In these embodiments, the additional metal oxide may be present in an amount which is greater than or equal to about 0 mol. % and less than or equal to about 2 mol. %. For example, when the additional metal oxide is ZnO, the ZnO may be present in an amount greater than or equal to 1 mol. % and less than or equal to about 2 mol. %. When the additional metal oxide is $ZrO_2$ or $TiO_2$, the $ZrO_2$ or $TiO_2$ may be present in an amount less than or equal to about 1 mol. %.

Based on the foregoing, it should be understood that, in a first exemplary embodiment, a glass composition may include: $SiO_2$ in a concentration greater than about 70 mol. % and Y mol. % alkali oxide. The alkali oxide may include $Na_2O$ in an amount greater than about 8 mol. %. The glass composition may be free of boron and compounds of boron. The concentration of $SiO_2$ in this glass composition may be greater than or equal to about 72 mol. %, greater than 73 mol. % or even greater than 74 mol. %. The glass composition of this first exemplary embodiment may be free from phosphorous and compounds of phosphorous. The glass composition may also include X mol. % $Al_2O_3$. When $Al_2O_3$ is included, the ratio of Y:X may be greater than 1. The concentration of $Al_2O_3$ may be greater than or equal to about 2 mol. % and less than or equal to about 10 mol. %.

The glass composition of this first exemplary embodiment may also include alkaline earth oxide in an amount from about 3 mol. % to about 13 mol. %. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

In a second exemplary embodiment, a glass composition may include: greater than about 68 mol. % $SiO_2$; X mol. % $Al_2O_3$; Y mol. % alkali oxide; and $B_2O_3$. The alkali oxide may include $Na_2O$ in an amount greater than about 8 mol %. A ratio ($B_2O_3$ (mol. %)/(Y mol. %–X mol. %) may be greater than 0 and less than 0.3. The concentration of $SiO_2$ in this glass composition may be greater than or equal to about 72 mol. %, greater than 73 mol. % or even greater than 74 mol. %. The concentration of $Al_2O_3$ may be greater than or equal to about 2 mol. % and less than or equal to about 10 mol. %. In this second exemplary embodiment, the ratio of Y:X may be greater than 1. When the ratio of Y:X is greater than 1, an upper bound of the ratio of Y:X may be less than or equal to 2. The glass composition of this first exemplary embodiment may be free from phosphorous and compounds of phosphorous.

The glass composition of this second exemplary embodiment may also include alkaline earth oxide. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

The concentration of $B_2O_3$ in this second exemplary embodiment may be greater than or equal to about 0.01 mol. % and less than or equal to about 4 mol. %.

In a third exemplary embodiment, a glass article may have a type HgB1 hydrolytic resistance according to ISO 719. The glass article may include greater than about 8 mol. % $Na_2O$ and less than about 4 mol. % $B_2O_3$. The glass article may further comprise X mol. % $Al_2O_3$ and Y mol. % alkali oxide. The ratio ($B_2O_3$ (mol. %)/(Y mol. %–X mol. %) may be greater than 0 and less than 0.3. The glass article of this third exemplary embodiment may further include a compressive stress layer having a surface compressive stress greater than or equal to about 250 MPa. The glass article may also have at least a class S3 acid resistance according to DIN 12116; at least a class A2 base resistance according to ISO 695; and a type HgAl hydrolytic resistance according to ISO 720.

In a fourth exemplary embodiment, a glass pharmaceutical package may include $SiO_2$ in an amount greater than about 70 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. The glass pharmaceutical package may also have a type HGB1 hydrolytic resistance according to ISO 719. The concentration of $SiO_2$ in the glass pharmaceutical package of this fourth exemplary embodiment may be greater than or equal to 72 mol. % and less than or equal to about 78 mol. % or even greater than 74 mol. % and less than or equal to about 78 mol. %. The concentration of $Al_2O_3$ in the glass pharmaceutical may be greater than or equal to about 4 mol. % and less than or equal to about 8 mol. %. A ratio of Y:X may be greater than 1 and less than 2.

The glass pharmaceutical package of this fourth exemplary embodiment may also include alkaline earth oxide in an amount from about 4 mol. % to about 8 mol. %. The alkaline earth oxide may include MgO and CaO. The CaO may be present in an amount greater than or equal to about 0.2 mol. % and less than or equal to about 0.7 mol. %. A ratio (CaO (mol. %)/(CaO (mol. %)+MgO (mol. %))) may be less than or equal to 0.5. The glass pharmaceutical package of this fourth exemplary embodiment may have a type HGA1 hydrolytic resistance according to ISO 720.

In a fifth exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. A ratio of Y:X may be greater than 1. The glass composition may be free of boron and compounds of boron.

In a sixth exemplary embodiment, a glass composition may include from about 68 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. The glass composition of this sixth exemplary embodiment may also include $B_2O_3$. A ratio ($B_2O_3$ (mol. %)/(Y mol. %–X mol. %) may be greater than 0 and less than 0.3. A ratio of Y:X may be greater than 1.

In a seventh exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The amount of $Al_2O_3$ in the glass composition may be greater than or equal to about 2 mol. % and less than or equal to about 10 mol. %. The alkaline earth oxide may include CaO in an amount greater than or equal to about 0.1 mol. % and less than or equal to about 1.0 mol. %. The alkali oxide may include from about 0.01 mol. % to about 1.0 mol. % $K_2O$. A ratio of Y:X may be greater than 1. The glass composition may be free of boron and compounds of boron. The glass composition may be amenable to strengthening by ion exchange.

In a seventh exemplary embodiment, a glass composition may include $SiO_2$ in an amount greater than about 70 mol. % and less than or equal to about 80 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. A ratio of Y:X may be greater than 1.

In an eighth exemplary embodiment, a glass composition may include from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %; and Y mol. % alkali oxide, wherein the alkali oxide comprises $Na_2O$ in an amount greater than or equal to about 9 mol. % and less than or equal to about 15 mol. %. A ratio of a concentration of $B_2O_3$ (mol. %) in the glass pharmaceutical package to (Y mol. %–X mol. %) is less than 0.3. A ratio of Y:X may be greater than 1.

In a ninth exemplary embodiment, a pharmaceutical package for containing a pharmaceutical composition may include from about 70 mol. % to about 78 mol. % $SiO_2$; from about 3 mol. % to about 13 mol. % alkaline earth oxide; X mol. % $Al_2O_3$, wherein X is greater than or equal to 2 mol. % and less than or equal to about 10 mol. %; and Y mol. % alkali oxide, wherein the alkali oxide comprises $Na_2O$ in an amount greater than about 8 mol. %. The alkaline earth oxide may include CaO in an amount less than or equal to about 6.0 mol. %. A ratio of Y:X may be greater than about 1. The package may be free of boron and compounds of boron and may include a compressive stress layer with a compressive stress greater than or equal to about 250 MPa and a depth of layer greater than or equal to about 10 µm.

In a tenth exemplary embodiment, a glass article may be formed from a glass composition comprising from about 70 mol. % to about 78 mol. % $SiO_2$; alkaline earth oxide, wherein the alkaline earth oxide comprises MgO and CaO and a ratio (CaO (mol. %)/(CaO (mol. %)+MgO (mol. %))) is less than or equal to 0.5; X mol. % $Al_2O_3$, wherein X is from about 2 mol. % to about 10 mol. %; and Y mol. % alkali oxide, wherein the alkali oxide comprises $Na_2O$ in an amount greater than about 8 mol. % and a ratio of Y:X is greater than 1. The glass article may be ion exchange strengthened with a compressive stress greater than or equal to 250 MPa and a depth of layer greater than or equal to 10 µm. The glass article may have a type HgA1 hydrolytic resistance according to ISO 720.

As noted above, the presence of alkali oxides in the glass composition facilitates chemically strengthening the glass by ion exchange Specifically, alkali ions, such as potassium ions, sodium ions and the like, are sufficiently mobile in the glass to facilitate ion exchange. In some embodiments, the glass composition is ion exchangeable to form a compressive stress layer having a depth of layer greater than or equal to 10 µm. In some embodiments, the depth of layer may be greater than or equal to about 25 µm or even greater than or equal to about 50 µm. In some other embodiments, the depth of the layer may be greater than or equal to 75 µm or even greater than or equal to 100 µm. In still other embodiments, the depth of layer may be greater than or equal to 10 µm and less than or equal to about 100 µm. The associated surface compressive stress may be greater than or equal to about 250 MPa, greater than or equal to 300 MPa or even greater than or equal to about 350 MPa after the glass composition is treated in a salt bath of 100% molten $KNO_3$ at a temperature of 350° C. to 500° C. for a time period of less than about 30 hours or even about less than 20 hours.

The glass articles formed from the glass compositions described herein may have a hydrolytic resistance of HGB2 or even HGB1 under ISO 719 and/or a hydrolytic resistance of HGA2 or even HGA1 under ISO 720 (as described further herein) in addition to having improved mechanical characteristics due to ion exchange strengthening. In some embodiments described herein the glass articles may have compressive stresses which extend from the surface into the glass article to a depth of layer greater than or equal to 25 µm or even greater than or equal to 35 µm. In some embodiments, the depth of layer may be greater than or equal to 40 µm or even greater than or equal to 50 µm. The surface compressive stress of the glass article may be greater than or equal to 250 MPa, greater than or equal to 350 MPa, or even greater than or equal to 400 MPa. The glass compositions described herein facilitate achieving the aforementioned depths of layer and surface compressive stresses more rapidly and/or at lower temperatures than conventional glass compositions due to the enhanced alkali ion diffusivity of the glass compositions as described hereinabove. For example, the depths of layer (i.e., greater than or equal to 25 μm) and the compressive stresses (i.e., greater than or equal to 250 MPa) may be achieved by ion exchanging the glass article in a molten salt bath of 100% $KNO_3$ (or a mixed salt bath of $KNO_3$ and $NaNO_3$) for a time period of less than or equal to 5 hours or even less than or equal to 4.5 hours. In some embodiments, these depths of layer and compressive stresses may be achieved by ion exchanging the glass article in a molten salt bath of 100% $KNO_3$ (or a mixed salt bath of $KNO_3$ and $NaNO_3$) for a time period of less than or equal to 4 hours or even less than or equal to 3.5 hours. Moreover, these depths of layers and compressive stresses may be achieved by ion exchanging the glass articles in a molten salt bath of 100% KNO3 (or a mixed salt bath of $KNO_3$ and $NaNO_3$) at a temperature less than or equal to 500° C. or even less than or equal to 450° C. In some embodiments, these depths of layers and compressive stresses may be achieved by ion exchanging the glass articles in a molten salt bath of 100% KNO3 (or a mixed salt bath of $KNO_3$ and $NaNO_3$) at a temperature less than or equal to 400° C. or even less than or equal to 350° C.

These improved ion exchange characteristics can be achieved when the glass composition has a threshold diffusivity of greater than about 16 μm$^2$/hr or even greater than or equal to 20 μm$^2$/hr at 450° C. In some embodiments, the threshold diffusivity may be greater than or equal to about 25 μm$^2$/hr or even 30 μm$^2$/hr at 450° C. In some other embodiments, the threshold diffusivity may be greater than or equal to about 35 μm$^2$/hr or even 40 μm$^2$/hr at 450° C. In still other embodiments, the threshold diffusivity may be greater than or equal to about 45 μm$^2$/hr or even 50 μm$^2$/hr at 450° C.

The glass compositions described herein may generally have a strain point greater than or equal to about 525° C. and less than or equal to about 650° C. The glasses may also have an anneal point greater than or equal to about 560° C. and less than or equal to about 725° C. and a softening point greater than or equal to about 750° C. and less than or equal to about 960° C.

In the embodiments described herein the glass compositions have a CTE of less than about 70×10$^{-7}$K$^{-1}$ or even less than about 60×10$^{-7}$K$^{-1}$. These lower CTE values improve the survivability of the glass to thermal cycling or thermal stress conditions relative to glass compositions with higher CTEs.

Further, as noted hereinabove, the glass compositions are chemically durable and resistant to degradation as determined by the DIN 12116 standard, the ISO 695 standard, and the ISO 720 standard.

Specifically, the DIN 12116 standard is a measure of the resistance of the glass to decomposition when placed in an acidic solution. In brief, the DIN 12116 standard utilizes a polished glass sample of a known surface area which is weighed and then positioned in contact with a proportional amount of boiling 6M hydrochloric acid for 6 hours. The sample is then removed from the solution, dried and weighed again. The glass mass lost during exposure to the acidic solution is a measure of the acid durability of the sample with smaller numbers indicative of greater durability. The results of the test are reported in units of half-mass per surface area, specifically mg/dm$^2$. The DIN 12116 standard is broken into individual classes. Class 51 indicates weight losses of up to 0.7 mg/dm$^2$; Class S2 indicates weight losses from 0.7 mg/dm$^2$ up to 1.5 mg/dm$^2$; Class S3 indicates weight losses from 1.5 mg/dm$^2$ up to 15 mg/dm$^2$; and Class S4 indicates weight losses of more than 15 mg/dm$^2$.

The ISO 695 standard is a measure of the resistance of the glass to decomposition when placed in a basic solution. In brief, the ISO 695 standard utilizes a polished glass sample which is weighed and then placed in a solution of boiling 1M NaOH+0.5M $Na_2CO_3$ for 3 hours. The sample is then removed from the solution, dried and weighed again. The glass mass lost during exposure to the basic solution is a measure of the base durability of the sample with smaller numbers indicative of greater durability. As with the DIN 12116 standard, the results of the ISO 695 standard are reported in units of mass per surface area, specifically mg/dm$^2$. The ISO 695 standard is broken into individual classes. Class A1 indicates weight losses of up to 75 mg/dm$^2$; Class A2 indicates weight losses from 75 mg/dm$^2$ up to 175 mg/dm$^2$; and Class A3 indicates weight losses of more than 175 mg/dm$^2$.

The ISO 720 standard is a measure of the resistance of the glass to degradation in purified, $CO_2$-free water. In brief, the ISO 720 standard protocol utilizes crushed glass grains which are placed in contact with the purified, $CO_2$-free water under autoclave conditions (121° C., 2 atm) for 30 minutes. The solution is then titrated colorimetrically with dilute HCl to neutral pH. The amount of HCl required to titrate to a neutral solution is then converted to an equivalent of $Na_2O$ extracted from the glass and reported in μg $Na_2O$ per weight of glass with smaller values indicative of greater durability. The ISO 720 standard is broken into individual types. Type HGA1 is indicative of up to 62 μg extracted equivalent of $Na_2O$ per gram of glass tested; Type HGA2 is indicative of more than 62 μg and up to 527 μg extracted equivalent of $Na_2O$ per gram of glass tested; and Type HGA3 is indicative of more than 527 μg and up to 930 μg extracted equivalent of $Na_2O$ per gram of glass tested.

The ISO 719 standard is a measure of the resistance of the glass to degradation in purified, $CO_2$-free water. In brief, the ISO 719 standard protocol utilizes crushed glass grains which are placed in contact with the purified, $CO_2$-free water at a temperature of 98° C. at 1 atmosphere for 30 minutes. The solution is then titrated colorimetrically with dilute HCl to neutral pH. The amount of HCl required to titrate to a neutral solution is then converted to an equivalent of $Na_2O$ extracted from the glass and reported in μg $Na_2O$ per weight of glass with smaller values indicative of greater durability. The ISO 719 standard is broken into individual types. The ISO 719 standard is broken into individual types. Type HGB1 is indicative of up to 31 μg extracted equivalent of $Na_2O$; Type HGB2 is indicative of more than 31 μg and up to 62 μg extracted equivalent of $Na_2O$; Type HGB3 is indicative of more than 62 μg and up to 264 μg extracted equivalent of $Na_2O$; Type HGB4 is indicative of more than 264 μg and up to 620 μg extracted equivalent of $Na_2O$; and Type HGB5 is indicative of more than 620 μg and up to 1085 μg extracted equivalent of $Na_2O$. The glass compositions described herein have an ISO 719 hydrolytic resistance of type HGB2 or better with some embodiments having a type HGB1 hydrolytic resistance.

The glass compositions described herein have an acid resistance of at least class S3 according to DIN 12116 both before and after ion exchange strengthening with some embodiments having an acid resistance of at least class S2 or even class 51 following ion exchange strengthening. In some other embodiments, the glass compositions may have an acid resistance of at least class S2 both before and after ion exchange strengthening with some embodiments having an acid resistance of class 51 following ion exchange strengthening. Further, the glass compositions described herein have a base resistance according to ISO 695 of at least class A2 before and after ion exchange strengthening with some embodiments having a class A1 base resistance at least after ion exchange strengthening. The glass compositions described herein also have an ISO 720 type HGA2 hydrolytic resistance both before and after ion exchange strengthening with some embodiments having a type HGA1 hydrolytic resistance after ion exchange strengthening and some other embodiments having a type HGA1 hydrolytic resistance both before and after ion exchange strengthening. The glass compositions described herein have an ISO 719 hydrolytic resistance of type HGB2 or better with some embodiments having a type HGB1 hydrolytic resistance. It should be understood that, when referring to the above referenced classifications according to DIN 12116, ISO 695, ISO 720 and ISO 719, a glass composition or glass article which has "at least" a specified classification means that the performance of the glass composition is as good as or better than the specified classification. For example, a glass article which has a DIN 12116 acid resistance of "at least class S2" may have a DIN 12116 classification of either S1 or S2.

The glass compositions described herein are formed by mixing a batch of glass raw materials (e.g., powders of $SiO_2$, $Al_2O_3$, alkali oxides, alkaline earth oxides and the like) such that the batch of glass raw materials has the desired composition. Thereafter, the batch of glass raw materials is heated to form a molten glass composition which is subsequently cooled and solidified to form the glass composition. During solidification (i.e., when the glass composition is plastically deformable) the glass composition may be shaped using standard forming techniques to shape the glass composition into a desired final form. Alternatively, the glass article may be shaped into a stock form, such as a sheet, tube or the like, and subsequently reheated and formed into the desired final form.

Pharmaceutical Containers

In view of the chemical durability of the glass composition of the present invention, the glass compositions described herein are particularly well suited for use in designing pharmaceutical containers for storing, maintaining and/or delivering pharmaceutical compositions, such as liquids, solutions, powders, e.g., lyophilized powders, solids and the like. As used herein, the term "pharmaceutical container" refers to a composition designed to store, maintain and/or deliver a pharmaceutical composition. The pharmaceutical containers, as described herein, are formed, at least in part, of the delamination resistant glass compositions described above. Pharmaceutical containers of the present invention include, but are not limited to, Vacutainers™, cartridges, syringes, ampoules, bottles, flasks, phials, tubes, beakers, vials, injection pens or the like. In a particular embodiment, the pharmaceutical container is a vial. In a particular embodiment, the pharmaceutical container is an ampoule. In a particular embodiment, the pharmaceutical container is an injection pen. In a particular embodiment, the pharmaceutical container is a tube. In a particular embodiment, the pharmaceutical container is a bottle. In a particular embodiment, the pharmaceutical container is a syringe.

Moreover, the ability to chemically strengthen the glass compositions through ion exchange can be utilized to improve the mechanical durability of pharmaceutical containers formed from the glass composition. Accordingly, it should be understood that, in at least one embodiment, the glass compositions are incorporated in a pharmaceutical container in order to improve the chemical durability and/or the mechanical durability of the pharmaceutical container.

Pharmaceutical Compositions

In various embodiments, the pharmaceutical container further includes a pharmaceutical composition comprising an active pharmaceutical ingredient (API). As used herein, the term "pharmaceutical composition" refers to a composition comprising an active pharmaceutical ingredient to be delivered to a subject, for example, for therapeutic, prophylactic, diagnostic, preventative or prognostic effect. In certain embodiments, the pharmaceutical composition comprises the active pharmaceutical ingredient and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active pharmaceutical agent.

As used herein, the term "active pharmaceutical ingredient" or "API" refers a substance in a pharmaceutical composition that provides a desired effect, for example, a therapeutic, prophylactic, diagnostic, preventative or prognostic effect. In various embodiments, the active pharmaceutical ingredient can be any of a variety of substances known in the art, for example, a small molecule, a polypeptide mimetic, a biologic, an antisense RNA, a small interfering RNA (siRNA), etc.

For example, in a particular embodiment, the active pharmaceutical ingredient may be a small molecule. As used herein, the term "small molecule" includes any chemical or other moiety, other than polypeptides and nucleic acids, that can act to affect biological processes. Small molecules can include any number of therapeutic agents presently known and used, or that can be synthesized from a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include, without limitation, organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

In another embodiment, the active pharmaceutical ingredient may be a polypeptide mimetic ("peptidomimetic"). As used herein, the term "polypeptide mimetic" is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

In other embodiments, the active pharmaceutical ingredient may be a biologic. As used herein, the term "biologic" includes products created by biologic processes instead of b chemical synthesis. Non-limiting examples of a "biologic" include proteins, antibodies, antibody like molecules, vaccines, blood, blood components, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64 (8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253 (5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307 (1):198-205. Additional discussion of related principles, methods, etc., that may be applicable in the context of this invention are provided in, e.g., Fassina, Immunomethods. October 1994; 5 (2):121-9.

In various embodiments, the active pharmaceutical ingredient may have any of a variety of activities selected from the group consisting of anti-rheumatics, anti-neoplastic, vaccines, anti-diabetics, haematologicals, muscle relaxant, immunostimulants, anti-coagulants, bone calcium regulators, sera and gammaglobulins, anti-fibrinolytics, MS therapies, anti-anaemics, cytostatics, interferons, anti-metabolites, radiopharmaceuticals, anti-psychotics, anti-bacterials, immunosuppressants, cytotoxic antibiotics, cerebral & peripheral vasotherapeutics, nootropics, CNS drugs, dermatologicals, angiotensin antagonists, anti-spasmodics, anti-cholinergics, interferons, anti-psoriasis agents, anti-hyperlipidaemics, cardiac therapies, alkylating agents, bronchodilators, anti-coagulants, anti-inflammatories, growth hormones, and diagnostic imaging agents.

In particular embodiments, the pharmaceutical composition may be selected from the group of pharmaceutical products or active pharmaceutical ingredients (API) set forth in Table 1.

TABLE 1

Approved Pharmaceutical Products

| PRODUCT | GENERIC NAME | THERAPEUTIC SUBCATEGORY |
|---|---|---|
| Humira | Adalimumab | Other anti-rheumatics |
| Avastin | Bevacizumab | Anti-neoplastic MAbs |
| Prevnar 13 | pneumococcal vaccine | Vaccines |
| Lantus | insulin glargine recombinant | Anti-diabetics |
| Rituxan | Rituximab | Anti-neoplastic MAbs |
| Herceptin | Trastuzumab | Anti-neoplastic MAbs |
| Remicade | Infliximab | Other anti-rheumatics |
| NovoRapid | insulin aspart | Anti-diabetics |
| Victoza | Liraglutide | Anti-diabetics |
| Soliris | Eculizumab | Other haematologicals |
| Enbrel | Etanercept | Other anti-rheumatics |
| Enbrel | Etanercept | Other anti-rheumatics |
| Botox | botulinum toxin type A | Muscle relaxant, peripheral |
| Neulasta | Pegfilgrastim | Immunostimulants |
| Stelara | Ustekinumab | Immunosuppressants |
| Perjeta | Pertuzumab | Anti-neoplastic MAbs |
| Humalog | insulin lispro recombinant | Anti-diabetics |
| Lovenox | enoxaparin sodium | Anti-coagulants |
| Xgeva | Denosumab | Bone calcium regulators |
| Privigen | immune globulin (human) | Sera & gammaglobulins |
| Gammagard Liquid | immune globulin (human) | Sera & gammaglobulins |
| Orencia | Abatacept | Other anti-rheumatics |
| Eylea | Aflibercept | Eye preparations |
| Human insulin & devices | insulin (human) | Anti-diabetics |
| PENTAct-HIB | DTPw, Hib & polio vaccine | Vaccines |
| Advate | factor VIII (procoagulant) | Anti-fibrinolytics |
| Actemra | Tocilizumab | Other anti-rheumatics |
| NovoMix 30 | insulin; insulin aspart | Anti-diabetics |
| Yervoy | Ipilimumab | Anti-neoplastic MAbs |
| Avonex | interferon beta-1a | MS Therapies |
| Bydureon | exenatide synthetic | Anti-diabetics |
| Aranesp | darbepoetin alfa | Anti-anaemics |
| Fluzone/Vaxigrip | influenza vaccine | Vaccines |
| Kogenate | octocog alfa | Anti-fibrinolytics |
| Tysabri | Natalizumab | MS Therapies |

TABLE 1-continued

Approved Pharmaceutical Products

| PRODUCT | GENERIC NAME | THERAPEUTIC SUBCATEGORY |
|---|---|---|
| Rebif | interferon beta-1a | MS Therapies |
| NovoSeven | eptacog alfa | Anti-fibrinolytics |
| Levemir | insulin detemir | Anti-diabetics |
| Cimzia | certolizumab pegol | Other anti-rheumatics |
| Kyprolis | Carfilzomib | Other cytostatics |
| Humulin R | insulin (human) | Anti-diabetics |
| Lucentis | Ranibizumab | Eye preparations |
| Gamunex IGIV | immune globulin (human) | Sera & gammaglobulins |
| Remicade | Infliximab | Other anti-rheumatics |
| Gardasil | human papillomavirus (HPV) vaccine | Vaccines |
| Pediarix | DTP, hepatitis B & polio vaccine | Vaccines |
| Velcade | Bortezomib | Other cytostatics |
| Pegasys | peginterferon alfa-2a | Interferons |
| Simponi | Golimumab | Other anti-rheumatics |
| Hepatitis Vaccine Franchise | hepatitis A & B vaccine | Vaccines |
| Forteo | teriparatide recombinant human | Bone calcium regulators |
| Copaxone | glatiramer acetate | MS Therapies |

In a particular embodiment, the pharmaceutical composition comprises Adalimumab. Adalimumab (HUMIRA®) is a recombinant fully human IgG1 monoclonal antibody that is indicated for the treatment of rheumatoid arthritis, juvenile idiopathic arthritis, psoriatic arthritis, ankylosing spondylitis, Crohn's disease, ulcerative colitis, and plaque psoriasis.

Adalimumab, comprised of human derived heavy and light chain variable regions and human IgG1:k constant regions composed of 1330 amino acids, binds to human tumor necrosis factor alpha (TNFα) and prevents activation of the p55 and p75 TNF receptors. Adalimumab has a molecular weight of approximately 148 kilodaltons and is supplied as a clear and colorless liquid in a prefilled glass syringe. The drug is packaged in doses of either a 40 mg or 20 mg in buffered water and to a pH of about 5.2.

The 40 mg dose comprises water, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, and 0.8 mg polysorbate 80 in a total volume of 0.8 mL. The 20 mg dose comprises water, 2.47 mg sodium chloride, 0.34 mg monobasic sodium phosphate dihydrate, 0.61 mg dibasic sodium phosphate dihydrate, 0.12 mg sodium citrate, 0.52 mg citric acid monohydrate, 4.8 mg mannitol, and 0.4 mg polysorbate 80 in a total volume of 0.4 ml. Both the 40 mg and 20 mg dose formulations may also include sodium hydroxide to adjust pH.

In a particular embodiment, the pharmaceutical composition comprises Bevacizumab. Bevacizumab (AVASTIN®) is a recombinant humanized monoclonal IgG1 antibody that is indicated as a first- or second-line treatment of patients with metastatic carcinoma of the colon or rectum in combination with intravenous 5-fluorouracil-based chemotherapy; as a first-line treatment of unresectable, locally advanced, recurrent or metastatic non-squamous non-small cell lung cancer in combination with carboplatin and paclitaxel; as a treatment for glioblastoma with progressive disease in adult patients following prior therapy as a single agent; and as a treatment for metastatic renal cell carcinoma in combination with interferon alfa.

Bevacizumab, comprised of human framework regions and the complementarity-determining regions of a murine antibody that binds to endothelial growth factor (VEGF), binds to human vascular endothelial growth factor (VEGF) and inhibits angiogenesis. The antibody-VEGF protein complex is unable to bind to the Flt-1 or KDR receptors on endothelial cells thereby inhibiting microvascular growth. Bevacizumab has a molecular weight of approximately 149 kD and is supplied as a clear to slightly opalescent, colorless to pale brown liquid in a vial. The drug product is supplied in either a 100 mg or 400 mg dose in buffered water to a pH of about 6.2.

The 100 mg dose comprises water, 240 mg α,α-trehalose dihydrate, 23.2 mg sodium phosphate (monobasic, monohydrate), 4.8 mg sodium phosphate (dibasic, anhydrous), and 1.6 mg polysorbate 20 in a total volume of 4.0 mL. The 400 mg dose comprises water, 960 mg α,α-trehalose dihydrate, 92.8 mg sodium phosphate (monobasic, monohydrate), 19.2 mg sodium phosphate (dibasic, anhydrous), and 6.4 mg polysorbate 20 in a total volume of 16.0 mL.

In a particular embodiment, the pharmaceutical composition comprises Pneumococcal 13-valent conjugate (Diphtheria $CRM_{197}$ Protein). Pneumococcal 13-valent conjugate (Diphtheria $CRM_{197}$ Protein) (PREVNAR 13®) is a vaccine indicated for use in children age 6 weeks through 5 years for active immunization for the prevention of invasive disease caused by *Streptococcus pneumoniae* serotypes 1, 3, 4, 5, 6A, 6B, 7F, 9V, 14, 18C, 19A, 19F and 23F and for active immunization for the prevention of otitis media caused by *Streptococcus pneumoniae* serotypes 4, 6B, 9V, 14, 18C, 19F, and 23F. This vaccine is also indicated for use in adults 50 years of age and older for active immunization for the prevention of pneumonia and invasive disease caused by *Streptococcus pneumoniae* serotypes 1, 3, 4, 5, 6A, 6B, 7F, 9V, 14, 18C, 19A, 19F and 23F.

Pneumococcal 13-valent conjugate (Diphtheria $CRM_{197}$ Protein) is comprised of polysaccharides of the capsular antigens of *Streptococcus pneumonia* serotypes 1, 3, 4, 5, 6A, 6B, 7F, 9V, 14, 18C, 19A, 19F, and 23F, conjugated to a nontoxic recombinant variant of the diphtheria toxin protein ($CRM_{197}$). Pneumococcal 13-valent conjugate (Diphtheria $CRM_{197}$ Protein) is supplied in pre-filled syringes containing approximately 2.2 μg of each of the serotype saccharides 1, 3, 4, 5, 6A, 7F, 9V, 14, 18C, 19A, 19F, and 23F and 4.4 ug of 6B. The vaccine also includes 34 μg $CRM_{197}$ carrier protein, 100 μg polysorbate 80, 295 μg succinate buffer and 125 μg aluminum as aluminum phosphate adjuvant.

In a particular embodiment, the pharmaceutical composition comprises insulin glargine [rDNA]. Insulin glargine [rDNA] injection (LANTUS®) is a long-acting recombinant human insulin analogue indicated for the treatment of adults and children with type 1 diabetes mellitus and in adults with type 2 diabetes mellitus in order to improve glycemic control.

Figure 8:
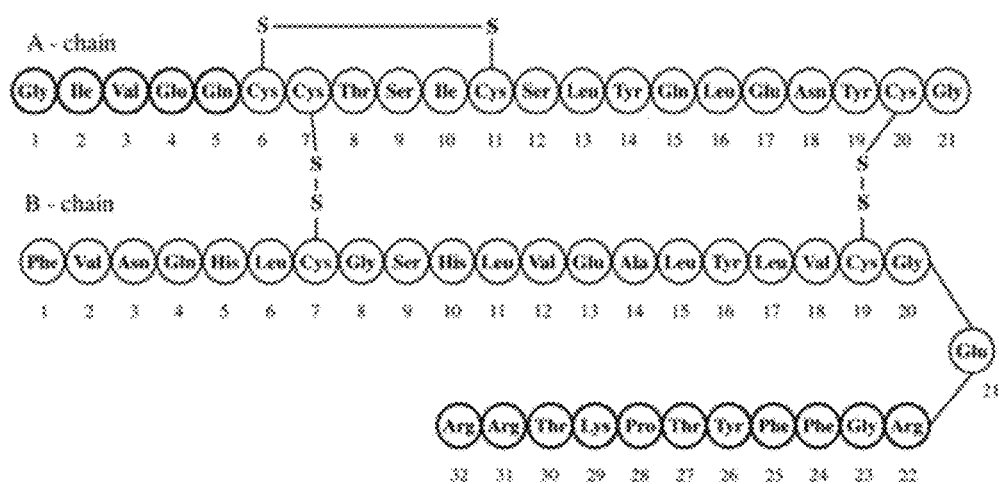
FIG. 8 depicts the structure of insulin glargine, in which the core peptide of the A-chain is disclosed as SEQ ID NO:1 and the core peptide of the B-chain is disclosed as SEQ ID NO:2.

Insulin glargine [rDNA] injection, having the chemical formula $21^A$-Gly-$30^a$a-L-Arg-$30^B$b-L-Arg-human insulin ($C_{267}H_{404}N_{72}O_{78}S_6$) and a molecular weight of 6063 daltons, lowers blood glucose levels by stimulating peripheral glucose uptake by tissues (e.g. skeletal muscle and fat) and by inhibiting hepatic glucose production. Insulin glargine also inhibits lipolysis and proteolysis and enhances protein synthesis. Insulin glargine differs from human insulin in that the A21 amino acid is replaced by glycine and two arginines are added to the C-terminus of the B-chain. The structure of insulin glargine is depicted in FIG. 8.

Insulin glargine (structure shown above) is supplied in a vial as a clear aqueous fluid containing 100 Units (3.6378 mg) insulin glargine with a pH of approximately 4.0. The drug product is supplied in either a 10 mL or 3 mL size and, in addition to insulin glargine, contains 30 mcg zinc, 2.7 mg m-cresol, 20 mg glycerol 85%, and 20 mcg polysorbate 20 per mL in water. The formulation may also include sodium hydroxide and/or hydrochloric acid added to adjust pH.

In a particular embodiment, the pharmaceutical composition comprises Rituximab. Rituximab (RITUXAN®) is a recombinant chimeric murine/human monoclonal IgG1 kappa antibody that is indicated for the treatment Non-Hodgkin's lymphoma, chronic lymphocytic leukemia, rheumatoid arthritis in adults with moderately- to severely-active disease who have inadequate response to one or more TNF antagonist therapies, granulomatosis with polyangiitis (Wegener's Granulomatosis), and microscopic polyangiitis in adult patients.

Rituximab, having a molecular weight of approximately 145 kD, binds to the CD20 antigen via the Fab domain. The Fc domain of the antibody recruits immune effector functions to mediate B-cell lysis in vitro. The CD20 antigen is also known as the human B-lymphocyte-restricted differentiation antigen, Bp35 and is a hydrophobic transmembrane protein found on pre-B and mature B lymphocytes. The antigen is expressed on >90% of B-cell non-Hodgkin's lymphomas, but it is not found on hematopoietic stem cells, pro-B-cells, normal plasma cells or other normal tissues. In the pathogenesis of rheumatoid arthritis B cells may be acting at multiple sites in the autoimmune/inflammatory process.

Rituximab is supplied in as a clear, colorless, preservative-free liquid at a concentration of 10 mg/mL in either 100 mg/10 mL or 500 mg/50 mL single-use vials at a pH of 6.5. In addition to rituximab, the drug product is formulated in polysorbate 80 (0.7 mg/mL), sodium citrate dihydrate (7.35 mg/mL), sodium chloride (9 mg/mL), and water.

In a particular embodiment, the pharmaceutical composition comprises Trastuzumab. Trastuzumab (HERCEPTIN®) is a humanized IgG1 kappa monoclonal antibody that is indicated for the treatment of HER2 overexpressing breast cancer and HER2-overexpressing metastatic gastric or gastroesophageal junction adenocarcinoma. HERCEPTIN® selectively binds to the extracellular domain of the human epidermal growth factor receptor 2 protein, HER2, and inhibits the growth of human tumor cells that overexpress the antigen.

Trastuzumab is supplied as a sterile, white to pale yellow, preservative-free lyophilized powder in multi-use vials. Each vial contains 440 mg trastuzumab, 400 mg α,α-trehalose dihydrate, 9.9 mg L-histidine HCl, 6.4 mg L-histidine, and 1.8 mg polysorbate 20. The lyophilized trastuzumab is reconstituted to a 21 mg/mL solution with 20 mL water and has a pH of approximately 6.

In a particular embodiment, the pharmaceutical composition comprises Infliximab. Infliximab, the active ingredient in REMICADE®, is a chimeric IgG1κ monoclonal antibody (composed of human constant and murine variable regions) specific for human tumor necrosis factor-alpha (TNFα). It has a molecular weight of approximately 149.1 kilodaltons. Infliximab is produced by a recombinant cell line cultured by continuous perfusion and is purified by a series of steps that includes measures to inactivate and remove viruses.

Infliximab neutralizes the biological activity of TNFα by binding with high affinity to the soluble and transmembrane forms of TNFα and inhibits binding of TNFα with its receptors. Infliximab does not neutralize TNFβ (lymphotoxin-α), a related cytokine that utilizes the same receptors as TNFα. Biological activities attributed to TNFα include: induction of pro-inflammatory cytokines such as interleukins (IL) 1 and 6, enhancement of leukocyte migration by increasing endothelial layer permeability and expression of adhesion molecules by endothelial cells and leukocytes, activation of neutrophil and eosinophil functional activity, induction of acute phase reactants and other liver proteins, as well as tissue degrading enzymes produced by synoviocytes and/or chondrocytes. Cells expressing transmembrane TNFα bound by infliximab can be lysed in vitro or in vivo.

Infliximab inhibits the functional activity of TNFα in a wide variety of in vitro bioassays utilizing human fibroblasts, endothelial cells, neutrophils, B and T-lymphocytes and epithelial cells. The relationship of these biological response markers to the mechanism(s) by which infliximab exerts its clinical effects is unknown. Anti-TNFα antibodies reduce disease activity in the cotton-top tamarin colitis model, and decrease synovitis and joint erosions in a murine model of collagen-induced arthritis. Infliximab prevents disease in transgenic mice that develop polyarthritis as a result of constitutive expression of human TNFα, and when administered after disease onset, allows eroded joints to heal.

Infliximab injection is used to relieve the symptoms of certain autoimmune disorders (conditions in which the immune system attacks healthy parts of the body and causes pain, swelling, and damage) including: rheumatoid arthritis (a condition in which the body attacks its own joints, causing pain, swelling, and loss of function) that is also being treated with methotrexate; Crohn's disease (a condition in which the body attacks the lining of the digestive tract, causing pain, diarrhea, weight loss, and fever) in adults and children 6 years of age or older that has not improved when treated with other medications; ulcerative colitis (condition that causes swelling and sores in the lining of the large intestine) in adults and children 6 years of age or older that has not improved when treated with other medications; ankylosing spondylitis (a condition in which the body attacks the joints of the spine and other areas causing pain and joint damage); psoriasis (a skin disease in which red, scaly patches form on some areas of the body); and psoriatic arthritis (a condition that causes joint pain and swelling and scales on the skin).

Infliximab is supplied in a vial as a sterile, white, lyophilized powder for intravenous infusion. Following reconstitution with 10 mL of Sterile Water for Injection, USP, the resulting pH is approximately 7.2. Each single-use 20 mL vial contains 100 mg infliximab, 500 mg sucrose, 0.5 mg polysorbate 80, 2.2 mg monobasic sodium phosphate, monohydrate, and 6.1 mg dibasic sodium phosphate, dihydrate. No preservatives are present.

In a particular embodiment, the pharmaceutical composition comprises insulin aspart [rDNA origin]. Insulin aspart [rDNA origin] injection (NOVOLOG®) is a rapid-acting human insulin analog that is indicated for use in adults and children with diabetes mellitus for improvement of glycemic control.

Figure 9:
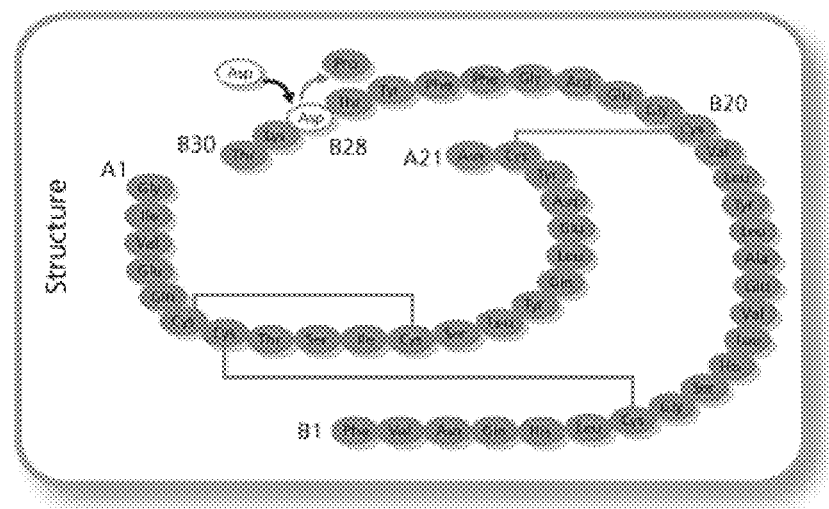
FIG. 9 depicts the structure of insulin aspart, in which the core peptide of the A chain is disclosed as SEQ ID NO:3 and the core peptide of the B-chain is disclosed as SEQ ID NO:4.

Insulin aspart, having the empirical formula $C_{256}H_{381}N_{65}O_{79}S_6$ and a molecular weight of 5825.8 daltons, lowers blood glucose by binding to insulin receptors and stimulating peripheral glucose uptake by tissues (e.g. skeletal muscle and fat) and by inhibiting hepatic glucose production. The compound is homologous to human insulin with the exception of a single substitution of the amino acid proline by aspartic acid in position B28. The structure of insulin aspart is depicted in FIG. 9.

Insulin aspart (structure shown above) is a sterile, aqueous, clear, and colorless solution, that contains insulin aspart 100 Units/mL, glycerin 16 mg/mL, phenol 1.50 mg/mL, metacresol 1.72 mg/mL, zinc 19.6 mcg/mL, disodium hydrogen phosphate dihydrate 1.25 mg/mL, sodium chloride 0.58 mg/mL and water with a pH of 7.2-7.6. The formulation may also include sodium hydroxide and/or hydrochloric acid added to adjust pH.

In a particular embodiment, the pharmaceutical composition comprises Liraglutide. Liraglutide (VICTOZA®) is an analogue of human glucagon-like-peptide (GLP-1) and is indicated for use as an adjunct to diet and exercise to improve glycemic control in adults with type 2 diabetes mellitus.

Figure 10:
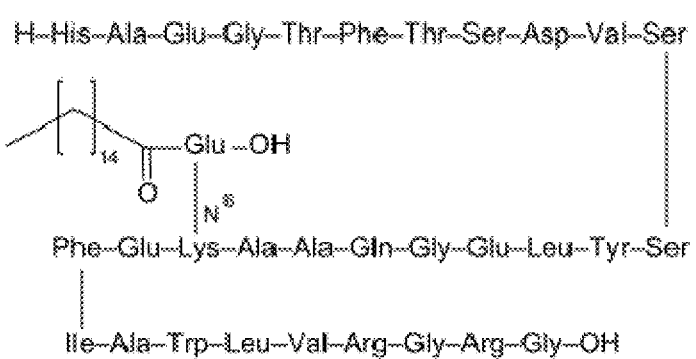
FIG. 10 depicts the structure of liragultide, the core peptide of which is disclosed as SEQ ID NO:5.

Liraglutide, having the chemical formula of $C_{172}H_{265}N_{43}O_{51}$ and a molecular weight of 3751.2 daltons, acts as a GLP-1 receptor agonist. Liraglutide activates the GLP-1 receptor which is coupled to adenylyl cyclase by the stimulatory G-protein, Gs, in pancreatic beta cells. Activation of the GLP-1 receptor results in an increase in intracellular cyclic AMP which leads to insulin release in the presence of elevated glucose concentrations. Liraglutide also decreases glucagon secretion in a glucose-dependent manner. Liragultide is 97% homologous to native human GLP-1 by substitution of arginine for lysine at position 34. The structure of liraglutide is depicted in FIG. 10.

Liraglutide (structure shown above) is supplied as a clear, colorless solution with each 1 mL of solution containing 6 mg of liraglutide. Each pre-filled pen contains a 3 mL solution equivalent to 18 mg liraglutide (free-base, anhydrous) and the following inactive ingredients: 1.42 mg of disodium phosphate dihydrate, 14 mg propylene glycol, 5.5 mg phenol, and water.

In a particular embodiment, the pharmaceutical composition comprises Exulizumab. Exulizumab (SOLIRIS®) is a recombinant humanized monoclonal IgG2/4κ antibody that is indicated for the treatment of patients with paroxysmal nocturnal hemoglobinuria to reduce hemolysis and for the treatment of patients with atypical hemolytic uremic syndrome to inhibit complement-mediated thrombotic microangiopathy.

Exulizumab, having a molecular weight of approximately 148 kDa, binds the complement protein C5 and inhibits its cleavage to C5a and C5b and thus prevents the generation of the terminal complement complex C5b-9 Inhibition of terminal complement complex generation inhibits intravascular hemolysis and complement mediated thrombotic microangiopathy. The antibody is comprised of human constant regions from human IgG2 sequences and human IgG4 sequences and murine complementarity-determining regions grafted onto the human framework light- and heavy-chain variable regions.

Exulizumab is supplied in 30 mL single use vials as a clear, colorless, solution. Each vial contains 300 mg of eculizumab, 13.8 mg sodium phosphate monobasic, 53.4 mg sodium phosphate dibasic, 263.1 mg sodium chloride, 6.6 mg polysorbate 80 (vegetable origin) and water. The formulation has a pH of 7.

In a particular embodiment, the pharmaceutical composition comprises Etanercept. Etanercept (ENBREL®) is a dimeric fusion protein indicated for the treatment of Rheumatoid Arthritis (RA), Polyarticular Juvenile Idiopathic Arthritis (JIA) in patients aged 2 years or older, Psoriatic Arthritis (PsA), Ankylosing Spondylitis (AS), and Plaque Psoriasis (PsO).

Etanercept, consisting of 934 amino acids and having an apparent molecular weight of approximately 150 kD, inhibits its binding of TNF-alpha and TNF-beta (lymphotoxin alpha [LT-alpha]) to cell surface tumor necrosis factor receptors (TNFRs), rendering TNF biologically inactive. Etanercept consists of the extracellular ligand-binding portion of the human 75 kD (p75) tumor necrosis factor receptor (TNFR) linked to the Fc portion of human IgG1.

Etanercept can modulate biological responses that are induced or regulated by TNF, including expression of adhesion molecules responsible for leukocyte migration (eg, E-selectin, and to a lesser extent, intercellular adhesion molecule-1 [ICAM-1]), serum levels of cytokines (eg, IL-6), and serum levels of matrix metalloproteinase-3 (MMP-3 or stromelysin). The Fc component of etanercept contains the CH2 domain, the CH3 domain and hinge region, but not the CH1 domain of IgG1. Etanercept is produced by recombinant DNA technology in a Chinese hamster ovary (CHO) mammalian cell expression system.

Etanercept is supplied in a single-use prefilled syringe or autoinjector for subcutaneous injection and is formulated with sucrose, sodium chloride, L-arginine hydrochloride, and sodium phosphate to pH 6.3±0.2. Etanercept is also supplied in a multiple-use vial as a lyophilized powder with mannitol, sucrose, and tromethamine, which can be reconstituted using Sterile Bacteriostatic Water for Injection, USP (0.9% benzyl alcohol) to pH 7.4±0.3.

In a particular embodiment, the pharmaceutical composition comprises OnabotulinumtoxinA. OnabotulinumtoxinA (botulinum toxin type A or BOTOX®) is an acetylcholine release inhibitor and a neuromuscular blocking agent that is indicated for the treatment of urinary incontinence due to detrusor overactivity associated with a neurologic condition [e.g., spinal cord injury (SCI), multiple sclerosis (MS)] in adults who have an inadequate response to or are intolerant of an anticholinergic medication; prophylaxis of headaches in adult patients with chronic migraine (≥15 days per month with headache lasting 4 hours a day or longer); treatment of upper limb spasticity in adult patients; treatment of cervical dystonia in adult patients, to reduce the severity of abnormal head position and neck pain; treatment of severe axillary hyperhidrosis that is inadequately managed by topical agents in adult patients; treatment of blepharospasm associated with dystonia in patients ≥12 years of age; and treatment of strabismus in patients ≥12 years of age.

OnabotulinumtoxinA is a neurotoxin that blocks neuromuscular transmission by binding to acceptor sites on motor or sympathetic nerve terminals, entering the nerve terminals, and inhibiting the release of acetylcholine. This inhibition occurs as the neurotoxin cleaves SNAP-25, a protein integral to the successful docking and release of acetylcholine from vesicles situated within nerve endings. When injected intramuscularly at therapeutic doses, onabotulinumtoxinA produces partial chemical denervation of the muscle resulting in a localized reduction in muscle activity. In addition, the muscle may atrophy, axonal sprouting may occur, and extrajunctional acetylcholine receptors may develop. There is evidence that reinnervation of the muscle may occur, thus slowly reversing muscle denervation produced by onabotulinumtoxinA. When injected intradermally, onabotulinumtoxinA produces temporary chemical denervation of the sweat gland resulting in local reduction in sweating. Following intradetrusor injection, onabotulinumtoxinA affects the efferent pathways of detrusor activity via inhibition of acetylcholine release. In addition, onabotulinumtoxinA is believed to inhibit afferent neurotransmitters and sensory pathways.

OnabotulinumtoxinA comprises *Clostridium botulinum* type A neurotoxin complex, Albumin Human, and sodium chloride. OnabotulinumtoxinA is currently supplied as a sterile, vacuum-dried purified botulinum toxin type A, produced from fermentation of Hall strain *Clostridium botulinum* type A, and intended for intramuscular, intradetrusor and intradermal use. It is purified from the culture solution by dialysis and a series of acid precipitations to a complex consisting of the neurotoxin, and several accessory proteins. The complex is dissolved in sterile sodium chloride solution containing Albumin Human and is sterile filtered (0.2 microns) prior to filling and vacuum-drying. Prior to injection into the subject, the vacuum-dried powder of OnabotulinumtoxinA is reconstituted using 0.9% Sodium Chloride Injection USP.

In a particular embodiment, the pharmaceutical composition comprises Pegfilgrastim. Pegfilgrastim (NEULASTA®; NEULASTIM®), a PEGylated form of the recombinant human granulocyte colony-stimulating factor (G-CSF) analog, filgrastim, is a leukocyte growth factor that is presently indicated to decrease the incidence of infection, as manifested by febrile neutropenia, in patients with non-myeloid malignancies receiving myelosuppressive anti-cancer drugs associated with a clinically significant incidence of febrile neutropenia.

Pegfilgrastim, having an average molecular weight of approximately 39 kD, is a colony-stimulating factor that acts on hematopoietic cells by binding to specific cell surface receptors, thereby stimulating proliferation, differentiation, commitment, and end cell functional activation. Pegfilgrastime is a covalent conjugate of recombinant methionyl human G-CSF (filgrastim) and monomethoxypolyethylene glycol. Filgrastim is a water-soluble 175 amino acid protein with a molecular weight of approximately 19 kD. Filgrastim is obtained from the bacterial fermentation of a strain of *E. coli* transformed with a genetically engineered plasmid containing the human G-CSF gene. To produce pegfilgrastim, a 20 kD monomethoxypolyethylene glycol molecule is covalently bound to the N-terminal methionyl residue of filgrastim.

Pegfilgrastim is currently supplied as a single use prefilled syringe for subcutaneous injection and is formulated in a sterile, clear, colorless, preservative-free solution (pH 4.0) containing acetate, polysorbate 20, sodium, and sorbitol in Water for Injection, USP.

In a particular embodiment, the pharmaceutical composition comprises Ustekinumab. Ustekinumab (STELARA®) is a human interleukin-12 and -23 antagonist presently indicated for the treatment of adult patients (18 years or older) with moderate to severe plaque psoriasis who are candidates for phototherapy or systemic therapy.

Ustekinumab, comprised of 1326 amino acids and having an estimated molecular mass that ranges from 148,079 to 149,690 Daltons, is a human IgG1κ monoclonal antibody that binds with high affinity and specificity the p40 subunit of the IL-12 and IL-23 cytokines. IL-12 and IL-23 are naturally occurring cytokines that are involved in inflammatory and immune responses, such as natural killer cell activation and CD4+ T-cell differentiation and activation. In in vitro models, ustekinumab was shown to disrupt IL-12 and IL-23 mediated signaling and cytokine cascades by disrupting the interaction of these cytokines with a shared cell-surface receptor chain, IL-12 β1. Using DNA recombinant technology, ustekinumab is produced in a well characterized recombinant cell line and is purified using standard bio-processing technology.

Ustekinumab is currently supplied as a single use prefilled syringe for subcutaneous injection and is formulated with L-histidine and L-histidine monohydrochloride monohydrate, Polysorbate 80, and sucrose to a final pH of 5.7-6.3.

In a particular embodiment, the pharmaceutical composition comprises Pertuzumab. Pertuzumab (PERJECTA®) is a HER2/neu receptor antagonist presently indicated in combination with trastuzumab and docetaxel for the treatment of patients with HER2-positive metastatic breast cancer who have not received prior anti-HER2 therapy or chemotherapy for metastatic disease.

Pertuzumab, having a approximate molecular weight of 148 kD, is a recombinant humanized monoclonal antibody that targets the extracellular dimerization domain (Subdomain II) of the human epidermal growth factor receptor 2 protein (HER2) and, thereby, blocks ligand-dependent heterodimerization of HER2 with other HER family members, including EGFR, HER3 and HER4. As a result, pertuzumab inhibits ligand-initiated intracellular signaling through two major signal pathways, mitogen-activated protein (MAP) kinase and phosphoinositide 3-kinase (PI3K) Inhibition of these signaling pathways can result in cell growth arrest and apoptosis, respectively. In addition, pertuzumab mediates antibody-dependent cell-mediated cytotoxicity (ADCC). While pertuzumab alone inhibited the proliferation of human tumor cells, the combination of pertuzumab and trastuzumab significantly augmented anti-tumor activity in HER2-overexpressing xenograft models. Pertuzumab is produced by recombinant DNA technology in a mammalian cell (Chinese Hamster Ovary) culture containing the antibiotic, gentamicin.

Pertuzumab is currently supplied in a single-use vial for intravenous infusion and is formulated with L-histidine acetate at pH 6.0, sucrose, and polysorbate 20.

Figure 11:
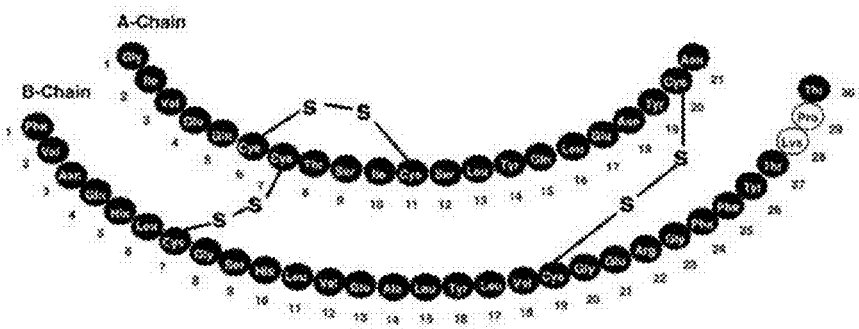
FIG. 11 depicts the structure of insulin lispro, in which the core peptide of the A-chain is disclosed as SEQ ID NO:3 and the core peptide of the B-chain is disclosed as SEQ ID NO:6.

In a particular embodiment, the pharmaceutical composition comprises Insulin lispro. Insulin lispro (insulin lispro recombinant; HUMALOG®) is a rapid acting human insulin analog used to lower blood glucose and is presently indicated to improve glycemic control in adults and children with diabetes mellitus. The structure of insulin lispro is depicted in FIG. 11.

Chemically, insulin lispro (shown above) is a Lys(B28), Pro(B29) human insulin analog having the empirical formula $C_{257}H_{383}N_{65}O_{77}S_6$ and a molecular weight of 5808, both identical to that of human insulin. Regulation of glucose metabolism is the primary activity of insulins and insulin analogs, including insulin lispro. Insulins lower blood glucose by stimulating peripheral glucose uptake by skeletal muscle and fat, and by inhibiting hepatic glucose production. Insulins inhibit lipolysis and proteolysis, and enhance protein synthesis. Insulin lispro is produced by recombinant DNA technology utilizing a non-pathogenic laboratory strain of *E. coli*. Insulin lispro differs from human insulin in that the amino acid proline at position B28 is replaced by lysine and the lysine in position B29 is replaced by proline.

Insulin lispro is currently supplied in vials, prefilled pens, and cartridges and is formulated as a solution with glycerin, dibasic sodium phosphate, Metacresol, zinc oxide, trace amounts of phenol, and Water for Injection. The insulin lispro solution has a pH of 7.0 to 7.8. The pH is adjusted by addition of aqueous solutions of hydrochloric acid 10% and/or sodium hydroxide 10%.

In a particular embodiment, the pharmaceutical composition comprises Enoxaparin or Exoxaparin sodium. Enoxaparin or enoxaparin sodium (LOVENOX®; XAPARIN; CLEXANE®) is a low molecular weight heparin which has antithrombotic properties and is presently indicated for prophylaxis of deep vein thrombosis (DVT) in abdominal surgery, hip replacement surgery, knee replacement surgery, or medical patients with severely restricted mobility during acute illness; inpatient treatment of acute DVT with or without pulmonary embolism; outpatient treatment of acute DVT without pulmonary embolism; prophylaxis of ischemic complications of unstable angina and non-Q-wave myocardial infarction (MI); and treatment of acute ST-segment elevation myocardial infarction (STEMI) managed medically or with subsequent percutaneous coronary intervention (PCI).

RANKL from activating its receptor, RANK, on the surface of osteoclasts and their precursors. Increased osteoclast activity, stimulated by RANKL, is a mediator of bone pathology in solid tumors with osseous metastases.

Denosumab is currently supplied in single-use vial for subcutaneous injection and is formulated as a solution with denosumab, sorbitol, acetate, Water for Injection (USP), and sodium hydroxide to a pH of 5.2.

In a particular embodiment, the pharmaceutical composition comprises Immune Globulin Intravenous (Human), 10% Liquid (PRIVIGEN®) Immune Globulin Intravenous (Human), 10% Liquid (PRIVIGEN®) is a sterile, 10%

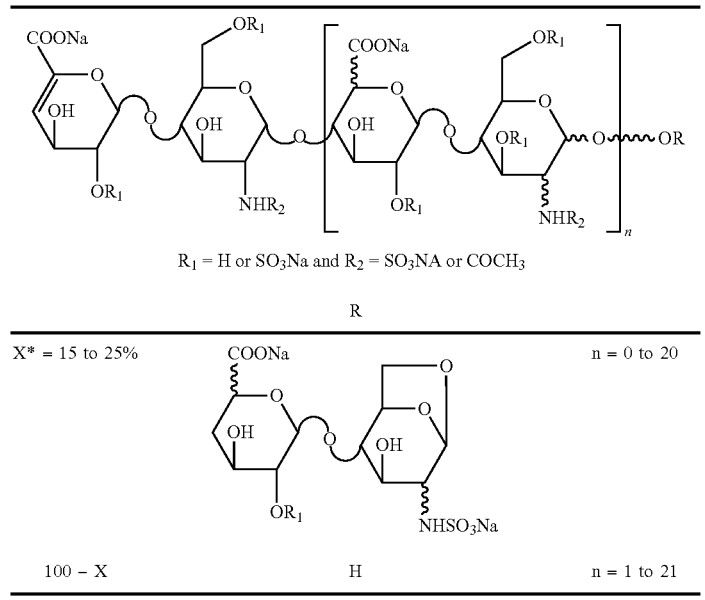

Enoxaparin sodium (shown above) is obtained by alkaline depolymerization of heparin benzyl ester derived from porcine intestinal mucosa. Its structure is characterized by a 2-O-sulfo-4-enepyranosuronic acid group at the non-reducing end and a 2-N,6-O-disulfo-D-glucosamine at the reducing end of the chain. About 20% (ranging between 15% and 25%) of the enoxaparin structure contains an 1,6 anhydro derivative on the reducing end of the polysaccharide chain. Enoxaparin sodium is the sodium salt. The average molecular weight is about 4500 daltons. The molecular weight distribution is <2000 daltons at ≤20%; 2000 to 8000 daltons at ≥68%; and >8000 daltons at ≤18%.

Enoxaparin sodium is currently supplied for subcutaneous and intravenous use as a solution in Water for Injection in a single-dose prefilled syringes as well as in multiple-dose vials with benzyl alcohol as a preservative. The pH of the injection is 5.5 to 7.5.

In a particular embodiment, the pharmaceutical composition comprises Denosumab. Denosumab (XGEVA®) is a human IgG2 monoclonal antibody that is presently indicated for prevention of skeletal-related events in patients with bone metastases from solid tumors.

Denosumab, having an approximate molecular weight of 147 kD and produced in genetically engineered mammalian (Chinese hamster ovary) cells, binds to and inhibits human receptor activator of nuclear factor kappa-B ligand (RANKL), a transmembrane or soluble protein essential for the formation, function, and survival of osteoclasts, the cells responsible for bone resorption. Denosumab prevents protein liquid preparation of polyvalent human immunoglobulin G (IgG) that is indicated for replacement therapy for primary humoral immunodeficiency (PI). This includes, but is not limited to, the humoral immune defect in congenital agammaglobulinemia, common variable immunodeficiency (CVID), X-linked agammaglobulinemia, Wiskott-Aldrich syndrome, and severe combined immunodeficiencies and supplies a broad spectrum of opsonic and neutralizing IgG antibodies against bacterial, viral, parasitic and *mycoplasma* agents and their toxins.

Immune Globulin Intravenous (Human), 10% Liquid is also indicated for the treatment of patients with chronic immune thrombocytopenic purpura (ITP) to raise platelet counts Immune Globulin Intravenous (Human), 10% Liquid has a purity of at least 98% IgG, consisting primarily of monomers. The balance consists of IgG dimers (≤12%), small amounts of fragments and polymers, and albumin Immune Globulin Intravenous (Human), 10% Liquid contains ≤25 mcg/mL IgA and has an osmolality of approximately 320 mOsmol/kg (range: 240 to 440).

Immune Globulin Intravenous (Human), 10% Liquid contains approximately 250 mmol/L (range: 210 to 290) of L-proline (a nonessential amino acid) as the sole stabilizer at a pH of 4.8 (range 4.6 to 5.0) and trace amounts of sodium Immune Globulin Intravenous (Human), 10% Liquid contains no carbohydrate stabilizers (e.g., sucrose, maltose) and no preservative.

The formulation of Immune Globulin Intravenous (Human), 10% Liquid with proline at a pH of 4.8 allows the product to remain stable when stored at room temperature (up to 25° C. [77° F.]) for 36 months for intravenous administration (10% IgG (0.1 g/mL).

In a particular embodiment, the pharmaceutical composition comprises Immune Globulin Intravenous (Human), 10% Solution (GAMMAGARD LIQUID). Immune Globulin Intravenous (Human), 10% Solution (GAMMAGARD LIQUID) is used to treat patients with primary immunodeficiency (PI) diseases and contains antibodies collected from healthy people that replace the missing antibodies in PI patients. It has been indicated as a replacement therapy for primary humoral immunodeficiency (PI) in adult and pediatric patients two years of age or older; and as a maintenance therapy to improve muscle strength and disability in adult patients with Multifocal Motor Neuropathy (MMN).

The most common types of PI result in an inability to make antibodies, which help the body fight off infections from bacteria or viruses. More specifically, Immune Globulin Intravenous (Human), 10% Solution is a sterile, liquid preparation of highly purified and concentrated immunoglobulin G (IgG) antibodies, which protect the body against infection. Immune Globulin Intravenous (Human), 10% Solution contains 100 mg/mL protein of which at least 98% of the protein is immune globulin, with the average immunoglobulin A (IgA) concentration is 37 µg/mL, and immunoglobulin M is present in trace amounts.

Immune Globulin Intravenous (Human), 10% Solution supplies a broad spectrum of opsonizing and neutralizing IgG antibodies against a wide variety of bacterial and viral agents Immune Globulin Intravenous (Human), 10% Solution also contains a spectrum of antibodies capable of interacting with and altering the activity of cells of the immune system as well as antibodies capable of reacting with cells such as erythrocytes. The role of these antibodies and the mechanisms of action of IgG in Immune Globulin Intravenous (Human), 10% Solution have not been fully elucidated.

Immune Globulin Intravenous (Human), 10% Solution contains a broad spectrum of IgG antibodies against bacterial and viral agents. Active ingredients comprise Human Immunoglobulin G with inactive ingredients Glycine (0.25 M) with a pH range from 4.6 to 5.1, with glycine as buffering agent.

In a particular embodiment, the pharmaceutical composition comprises Abatacept. Abatacept (ORENCIA®) is a soluble fusion protein drug formulation indicated for the treatment of Adult Rheumatoid Arthritis and Juvenile Idiopathic Arthritis. The fusion protein consists of the extracellular domain of human cytotoxic T-lymphocyte-associated antigen 4 (CTLA-4) linked to the modified Fc (hinge, CH2, and CH3 domains) portion of human immunoglobulin G1 (IgG1).

Abatacept is a selective costimulation modulator that inhibits T cell (T lymphocyte) activation by binding to CD80 and CD86, thereby blocking interactions with CD28. The aforementioned interaction provides a costimulatory signal necessary for full activation of T lymphocytes, wherein these activated T lymphocytes are implicated in the pathogenesis of rheumatoid arthritis. Abatacept thus reduces the signs and symptoms in adults with moderate to severe rheumatoid arthritis. Abatacept may prevent further damage to bones and joints and may improve a patient's ability to perform daily activities. In adults, Abatacept may be used alone or with various other rheumatoid arthritis treatments. In addition, Abatacept reduces signs and symptoms in children and adolescents 6 years of age and older with moderate to severe polyarticular juvenile idiopathic arthritis.

The formulation is comprised of abatacept with inactive ingredients dibasic anhydrous sodium phosphate, monobasic, monohydrate sodium phosphate, poloxamer 188, sucrose, water, with a pH range of 6.8 to 7.4.

In a particular embodiment, the pharmaceutical composition comprises Aflibercept. Aflibercept (EYLEA®) is a recombinant dimeric fusion glycoprotein consisting of portions of the human VEGF receptors 1 and 2 extracellular domains fused to the Fc portion of human IgG1. Aflibercept is indicated for the treatment of patients with Neovascular (Wet) Age-Related Macular Degeneration, which is a leading cause of vision loss and blindness in Americans ages 60 and older, and Macular Edema following Central Retinal Vein Occlusion. In people with the "wet form" of macular degeneration, new blood vessels grow under the retina where they leak blood and fluid.

From a mechanistic perspective, vascular endothelial growth factor-A (VEGF-A) and placental growth factor (PlGF) are members of the VEGF family of angiogenic factors that can act as mitogenic, chemotactic, and vascular permeability factors for endothelial cells. VEGF acts via two receptor tyrosine kinases, VEGFR-1 and VEGFR-2, present on the surface of endothelial cells. Activation of these receptors by VEGF-A can result in neovascularization and vascular permeability. Aflibercept acts as a soluble decoy receptor that binds VEGF-A and PlGF, and thereby inhibits the binding and activation of these cognate VEGF receptors, preventing new blood vessels from forming under the retina.

The formulation is comprised of aflibercept and the inactive ingredients sodium phosphate, sodium chloride, polysorbate 20, sucrose, buffered at a pH of 6.2. EYLEA® is supplied as a preservative-free, sterile, aqueous solution in a single-use, glass vial designed to deliver 0.05 mL (50 microliters) of aflibercept (40 mg/mL in 10 mM sodium phosphate, 40 mM sodium chloride, 0.03% polysorbate 20, and 5% sucrose, pH 6.2).

In a particular embodiment, the pharmaceutical composition comprises human insulin. Human insulin is a hormone that is produced in the body that functions through binding to insulin receptors on a cell's surface. Receptor-bound insulin functions to lower blood glucose levels by facilitating the cellular uptake of glucose into muscle and adipose tissue while simultaneously inhibiting the output of glucose from the liver. Notably, when an individual's insulin production is inadequate, or when an individual's cells do not respond properly to insulin, thus characterizing a group of metabolic diseases collectively known as diabetes, the health consequences can be severe. The symptoms of this group of diseases can be managed, at least in part, by the administration (e.g. via injection or oral delivery) of insulin.

In a particular embodiment, the pharmaceutical composition comprises Insulin regular (NOVOLIN® R). Insulin regular (NOVOLIN® R) is a formulation of recombinant insulin that is structurally identical to the insulin produced by the human pancreas (empirical formula $C_{25}H_{383}N_{65}O_{77}S_6$ and a molecular weight of 5808 Da). Novolin® is indicated for the treatment of patients with diabetes mellitus to control high blood sugar.

Insulin regular substitutes for inadequate endogenous insulin secretion and partially corrects the abnormal metabolism and inappropriate hyperglycemia of diabetes mellitus, which are caused by either a deficiency or a reduction in the biologic effectiveness of insulin. When administered in appropriate doses at prescribed intervals to patients with diabetes mellitus, insulin regular temporarily restores their ability to metabolize carbohydrates, proteins and fats. Insulin regular is characterized by a short duration of action. The pharmacologic effect of insulin regular begins approximately one-half hour after subcutaneous administration. The effect is maximal between 2½ and 5 hours and terminates after approximately 8 hours.

Insulin regular is a sterile, clear, aqueous, and colorless solution, that contains recombinant human insulin (100 units/mL), and inactive ingredients comprising glycerin (16 mg/ml), metacresol (3 mg/mL) and zinc chloride (approximately 7 µg/mL). The pH is adjusted to 7.4.

In a particular embodiment, the pharmaceutical composition comprises Human Insulin Isophane Suspension (NOVOLIN® N). Human Insulin Isophane Suspension (NOVOLIN® N) is a formulation of recombinant insulin that is indicated for the treatment of diabetes mellitus. From a structural perspective, human Insulin Isophane Suspension is identical to the insulin produced by the human pancreas, but this particular formulation that includes protamine, results in a long-acting form of insulin.

Human Insulin Isophane Suspension is a recombinant insulin NPH, which is used to control high blood sugar in patients with diabetes mellitus due to its ability to lower levels of glucose in the blood. The drug formulation comprises the recombinant human insulin with inactive ingredients zinc chloride, metacresol, glycerol, phenol, protamine sulfate, disodium phosphate dihydrate, sodium chloride, water.

In a particular embodiment, the pharmaceutical composition comprises Insulin Aspart Injection (NOVOLOG®). Insulin Aspart Injection (NOVOLOG®) is an insulin analog indicated to improve glycemic control in adults and children with diabetes mellitus.

The primary activity of insulin aspart injection is the regulation of glucose metabolism. From a structural perspective, the active ingredient of insulin aspart injection (insulin aspart, empirical formula $C_{256}H_{381}N_{65}O_{79}S_6$, molecular weight of 5825.8 Da) differs from regular human insulin by a single amino acid (a substitution of the amino acid proline for aspartic acid at position B28, see structural formula below), which reduces the tendency of insulin aspart injection to form hexamers (relative to hexamer formation of regular human insulin). Insulin aspart injection, therefore, is more rapidly absorbed after subcutaneous injection when compared to that of regular human insulin. The faster absorption of insulin aspart injection, results in a faster onset of action, and a shorter duration of action than regular human insulin.

Insulin aspart injection comprises insulin aspart (B28 asp regular human insulin analog, 100 Units/mL), glycerin (16 mg/mL), phenol (1.50 mg/mL), metacresol (1.72 mg/mL), zinc (19.6 µg/mL), disodium hydrogen phosphate dihydrate (1.25 mg/mL), and sodium chloride (0.58 mg/mL) at a pH range of 7.2 to 7.6.

The structural formula of insulin aspart is depicted in FIG. 9.

In a particular embodiment, the pharmaceutical composition comprises 70% human insulin isophane and 30% regular insulin (NOVOLIN® 70/30). 70% human insulin isophane and 30% regular insulin (NOVOLIN® 70/30) is an insulin formulation administered for the treatment of diabetes mellitus.

NOVOLIN® 70/30 is a recombinant insulin formulation consisting of a mixture of two different types of insulin, a short-acting insulin (regular human insulin) and an intermediate-acting insulin (human insulin isophane), that are used to control high blood sugar in patients with diabetes mellitus. The effects of Novolin 70/30 start working approximately 30 minutes after injection. The greatest blood sugar lowering effect is between 2 and 12 hours after the injection. This blood sugar lowering may last up to 24 hours. Thus, in principle, use of this formulation effectively decreases the number injections one needs in a day.

The active ingredients of this formulation include 70% NPH, Human Insulin Isophane Suspension and 30% regular insulin. The inactive ingredients comprise zinc chloride, metacresol, glycerol, phenol, disodium phosphate dihydrate, protamine sulfate, sodium chloride, and water.

In a particular embodiment, the pharmaceutical composition comprises Insulin aspart and insulin aspart protamine (NOVOLOG® MIX 70/30, NOVOMIX® 30). Insulin aspart and insulin aspart protamine (NOVOLOG® MIX 70/30, NOVOMIX® 30) is an insulin analog formulation indicated to improve glycemic control in patients with diabetes mellitus. The primary activity of NOVOLOG® MIX 70/30 is the regulation of glucose metabolism.

NOVOLOG® Mix 70/30 (70% insulin aspart protamine suspension and 30% insulin aspart injection) is a recombinant human insulin analog suspension containing 30% soluble insulin aspart, which is a rapid-acting human insulin analog characterized by an onset of action that occurs approximately within 10 to 20 minutes, and 70% insulin aspart protamine crystals, which is an intermediate-acting human insulin analog characterized by a maximum effect that occurs approximately between 1 and 4 hours after injection. NOVOLOG® Mix 70/30 is a blood glucose lowering agent with both a rapid onset and an intermediate duration of action. Insulin aspart is a recombinant protein homologous to regular human insulin except for a single substitution of the amino acid proline for aspartic acid at position B28. The addition of protamine to the rapid-acting aspart insulin analog (NOVOLOG®) results in insulin activity that is 30% short-acting and 70% long-acting.

The formulation comprises the active ingredients 70% insulin aspart protamine crystals and 30% soluble insulin aspart and the inactive ingredients mannitol (36.4 mg/mL), phenol (1.50 mg/mL), metacresol (1.72 mg/mL), zinc (19.6 µg/mL), disodium hydrogen phosphate dihydrate (1.25 mg/mL), sodium chloride (0.58 mg/mL), and protamine sulfate (0.32 mg/mL) at a pH ranging between 7.2 and 7.4.

In a particular embodiment, the pharmaceutical composition comprises Insulin detemir (LEVEMIR®). Insulin detemir (LEVEMIR®) is a long-acting human insulin analog indicated to improve glycemic control in adults and children with diabetes mellitus, however, LEVEMIR® is not recommended for the treatment of diabetic ketoacidosis.

Figure 12:
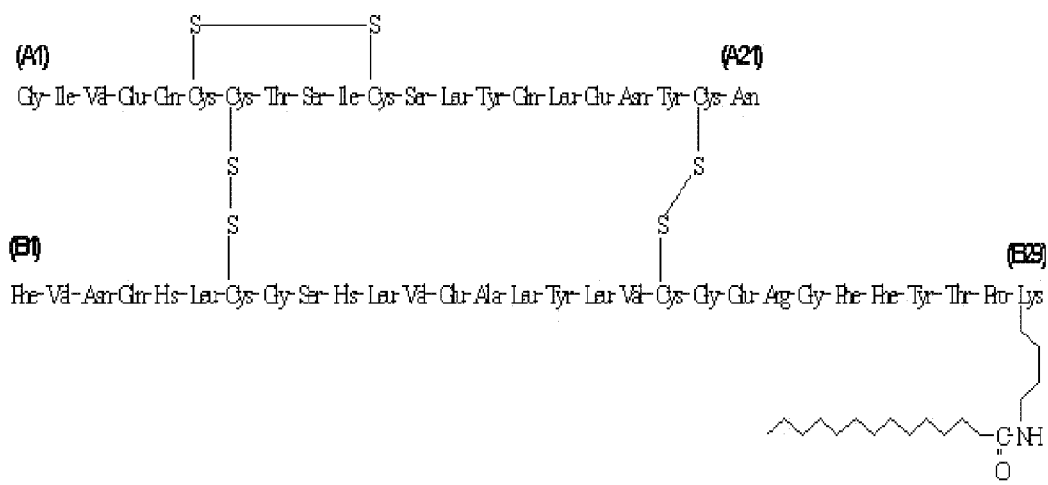
FIG. 12 depicts the structure of insulin detemir, in which the core peptide of the A-chain is disclosed as SEQ ID NO:3 and the core peptide of the B-chain is disclosed as SEQ ID NO:7.

The primary activity of insulin detemir (LEVEMIR®) is the regulation of glucose metabolism. Each milliliter of LEVEMIR® contains 100 units (14.2 mg/mL) insulin detemir, zinc (65.4 mcg), m-cresol (2.06 mg), glycerol (16.0 mg), phenol (1.80 mg), disodium phosphate dihydrate (0.89 mg), sodium chloride (1.17 mg), and water for injection. Hydrochloric acid and/or sodium hydroxide may be added to adjust pH. LEVEMIR® has a pH of approximately 7.4. Insulin detemir has a molecular formula of $C_{267}H_{402}O_{76}N_{64}S_6$ and a molecular weight of 5916.9 Da. The structural formula of insulin detemir is depicted in FIG. 12.

In a particular embodiment, the pharmaceutical composition comprises Diphtheria and tetanus toxoids and acellular pertussis adsorbed, inactivated poliovirus and *haemophilus* b conjugate (tetanus toxoid conjugate) vaccine (PENTACEL®). Diphtheria and tetanus toxoids and acellular pertussis adsorbed, inactivated poliovirus and *haemophilus* b conjugate (tetanus toxoid conjugate) vaccine (PENTACEL®) is a vaccine indicated for active immunization against diphtheria, tetanus, pertussis, poliomyelitis and invasive disease due to *Haemophilus influenzae* type b. The tetanus toxoid conjugate vaccine is approved for use as a four dose series in children 6 weeks through 4 years of age (prior to 5th birthday).

The tetanus toxoid conjugate vaccine consists of diphtheria and tetanus toxoids, acellular pertussis antigens and inactivated poliovirus components (collectively, DTaP-IPV) and the ActHIB® vaccine component (*H influenzae* Type B capsular polysaccharide (polyribosyl-ribitol-phosphate [PRP]) covalently bound to tetanus toxoid (PRP-T)) combined through reconstitution for intramuscular injection. The DTaP-IPV component is supplied as a sterile liquid used to reconstitute the lyophilized ActHIB vaccine component to form the Pentacel vaccine.

The tetanus toxoid conjugate vaccine is to be administered as a four-dose series at 2, 4, 6 and 15 to 18 months of age. The first dose may be given as early as 6 weeks of age. Four doses of the Pentacel vaccine constitute a primary immunization course against pertussis. Three doses of Pentacel vaccine constitute a primary immunization course against diphtheria, tetanus, *H influenzae* type b invasive disease, and poliomyelitis; the fourth dose is a booster for diphtheria, tetanus, *H influenzae* type b invasive disease, and poliomyelitis immunizations.

The tetanus toxoid conjugate vaccine formulation comprises the DTaP-IPV component comprising the Pertussis Toxoid (PT) (20 µg), Filamentous hemagglutinin (FHA) (20 µg), Fimbriae 2 & 3 (FIM) (5 µg), Pertactin (PRN) (3 µg), Diphtheria toxoid (15 LF), Tetanus toxoid (5 LF), poliovirus type 1 (Mahoney) (40 DAU), poliovirus type 2 (M.E.F.I.) (8 DAU), poliovirus type 3 (Saukett) (32 DAU), PRP (10 µg) conjugated to 24 µg tetanus toxoid, including the adjuvant Aluminum phosphate (1.5 mg; or 0.33 mg aluminum), the excipient 2-phenoxyethanol (0.6% (3.3 mg)),Tween 80 (~10 ppm), BSA (≤50 ng), Neomycin (<4 pg), Polymyxin B sulphate (<4 pg), Formaldehyde (≤0.001%, (≤5 µg)), Gluteraldehyde (<100 ppb (<50 ng)) and the ActHIB® vaccine component comprising polyribosyl-ribitol-phosphate capsular polysaccharide (PRP) (10 µg) conjugated to tetanus toxoid (24 µg), with no preservatives.

In a particular embodiment, the pharmaceutical composition comprises Antihemophilic factor (recombinant) (ADVATE). Antihemophilic factor (recombinant) (ADVATE) is indicated for (i) the control and prevention of bleeding episodes in adults and children (0 to 16 years) with Hemophilia A, (ii) the perioperative management in adults and children (0 to 16 years) with Hemophilia A, and (iii) routine prophylaxis to prevent or reduce the frequency of bleeding episodes in adults and children (0 to 16 years) with Hemophilia A. Antihemophilic factor is not indicated for the treatment of von Willebrand disease.

Antihemophilic factor is a genetically engineered, full-length clotting Factor VIII that is similar to the natural clotting factor found in a healthy individual. Hemophilia A is caused by a mutation in the blood clotting Factor VIII gene that results in a functional defect of the Factor VIII protein, which is an essential component of a cascade of reactions that lead to blood clotting. The administration of Antihemophilic factor helps people with hemophilia A prevent and control bleeding episodes, by temporarily raising the level of Factor VIII in the blood, thus allowing the body's blood clotting process to function properly. Antihemophilic factor is also used in the preparation for surgical operations in patients with hemophilia.

The drug formulation comprises recombinant human antihemophilic factor and the inactive ingredients mannitol (bulking agent), sodium chloride, buffering agents (Tris, histidine, at neutral pH), calcium chloride, polysorbate 80 (surfactant), and glutathione.

In a particular embodiment, the pharmaceutical composition comprises Tocilizumab (ACTEMRA®). Tocilizumab (ACTEMRA®) is an interleukin-6 (IL-6) receptor inhibitor indicated for the treatment of adult patients with moderately-to severely-active rheumatoid arthritis who have had an inadequate response to one or more TNF antagonist therapies.

Tocilizumab is a recombinant humanized monoclonal antibody directed against the interleukin 6 (IL-6) receptor. Tocilizumab binds specifically to both soluble and membrane-bound IL-6 receptors (sIL-6R and mIL-6R), and has been shown to inhibit IL-6-mediated signaling through these receptors. IL-6 is a pro-inflammatory cytokine produced by a variety of cell types including T- and B-cells, lymphocytes, monocytes and fibroblasts and has been shown to be involved in diverse physiological processes such as T-cell activation, induction of immunoglobulin secretion, initiation of hepatic acute phase protein synthesis, and stimulation of hematopoietic precursor cell proliferation and differentiation. IL-6 is also produced by synovial and endothelial cells leading to local production of IL-6 in joints affected by inflammatory processes such as rheumatoid arthritis.

The formulation comprises tocilizumab and the inactive ingredients sucrose, polysorbate 80, disodium phosphate dodecahydrate, sodium dihydrogen phosphate dehydrate, with a pH of approximately 6.5.

In a particular embodiment, the pharmaceutical composition comprises Insulin aspart mix (NOVOMIX® 30) (30% soluble insulin aspart and 70% insulin aspart protamine crystals). Insulin aspart mix (NOVOMIX® 30) (30% soluble insulin aspart and 70% insulin aspart protamine crystals) is indicated for the treatment of adult patients with diabetes mellitus who require insulin for the maintenance of normal glucose homeostasis.

Diabetes is a disease where an individual does not produce enough insulin to effectively control blood sugar levels, which can potentially lead to life-threatening health issues. Insulin aspart mix is used as a substitute for the body's insulin in people with diabetes.

Insulin aspart mix is an insulin analog formulation comprising a biphasic suspension that contains 30% soluble insulin aspart, which is a rapid-acting human insulin analog characterized by an onset of action that occurs within 10 to 20 minutes, and 70% protamine-crystallized insulin aspart, an intermediate-acting human insulin analog characterized by a maximum effect that occurs between 1 and 4 hours after injection. Both components of this biphasic suspension are produced by recombinant DNA technology.

The formulation also contains the following inactive ingredients: mannitol (36.4 mg/mL), phenol (1.50 mg/mL), metacresol (1.72 mg/mL), zinc (as chloride, 19.6 µg/mL), sodium chloride (0.58 mg/mL), disodium phosphate dehydrate (1.25 mg/mL), protamine sulphate (0.33 mg/mL), sodium hydroxide, hydrochloric acid and water for injection, with a pH range of 7.20 to 7.44.

In a particular embodiment, the pharmaceutical composition comprises Ipilimumab (YERVOY®). Ipilimumab (YERVOY®) is a human cytotoxic T-lymphocyte antigen 4 (CTLA-4)-blocking antibody indicated for the treatment of unresectable or metastatic melanoma.

Ipilimumab is a recombinant, human monoclonal antibody that binds to the cytotoxic T-lymphocyte-associated antigen 4 (CTLA-4) and is used to treat unresectable or metastatic melanoma that interferes with the growth and spread of cancer cells in the body. From a mechanistic perspective, CTLA-4 is a negative regulator of T-cell activation. Ipilimumab binds to CTLA-4 and blocks the interaction of CTLA-4 with its ligands, CD80/CD86. By disrupting the interaction of CTLA-4 with its ligands, T-cell activation and proliferation has been shown to increase. Thus, the mechanism of action in patients with melanoma is believed to involve T-cell mediated anti-tumor immune responses.

In addition to the active ingredient ipilimumab, this formulation contains inactive ingredients comprising diethylene triamine pentaacetic acid (DTPA), mannitol, polysorbate 80, sodium chloride, tris hydrochloride, with a pH of approximately 7.0.

In a particular embodiment, the pharmaceutical composition comprises Interferon beta-1a (AVONEX®). Interferon beta-1a (AVONEX®) is an interferon beta indicated for the treatment of patients with relapsing forms of multiple sclerosis to slow the accumulation of physical disability and decrease the frequency of clinical exacerbations. Patients with multiple sclerosis in whom efficacy has been demonstrated include patients who have experienced a first clinical episode and have MRI features consistent with multiple sclerosis.

Interferon beta-1a is a 166 amino acid glycoprotein with a molecular weight of approximately 22,500 daltons. It is produced by recombinant DNA technology using genetically engineered Chinese Hamster Ovary cells into which the human interferon beta gene has been introduced. The amino acid sequence of interferon beta-1a is identical to that of natural human interferon beta. Interferon beta-1a is for intramuscular use only and the recommended dose is 30 micrograms once a week. Interferon beta-1a may be titrated, starting with 7.5 micrograms for first week, to reduce flu-like symptoms, with a dose increase by 7.5 micrograms each week for next 3 weeks until recommended dose of 30 micrograms. Interferon beta-1a is available as a lyophilized powder, prefilled syringe, or pen.

A vial of interferon beta-1a is a sterile, white to off-white lyophilized powder for intramuscular injection after reconstitution with supplied diluent (Sterile Water for Injection, USP). Each vial of reconstituted interferon beta-1a contains 30 micrograms of interferon beta-1a; 15 mg Albumin (Human), USP; 5.8 mg Sodium Chloride, USP; 5.7 mg Dibasic Sodium Phosphate, USP; and 1.2 mg Monobasic Sodium Phosphate, USP, in 1.0 mL at a pH of approximately 7.3.

A prefilled syringe of interferon beta-1a is a sterile liquid for intramuscular injection. Each 0.5 mL (30 microgram dose) of interferon beta-1a in a prefilled glass syringe contains 30 micrograms of interferon beta-1a, 0.79 mg Sodium Acetate Trihydrate, USP; 0.25 mg Glacial Acetic Acid, USP; 15.8 mg Arginine Hydrochloride, USP; and 0.025 mg Polysorbate 20 in Water for Injection, USP at a pH of approximately 4.8.

AVONEX PEN® is a sterile liquid for intramuscular injection in a prefilled glass syringe surrounded by an autoinjector. Each 0.5 mL (30 microgram dose) in the AVONEX PEN® contains 30 micrograms of interferon beta-1a, 0.79 mg Sodium Acetate Trihydrate, USP; 0.25 mg Glacial Acetic Acid, USP; 15.8 mg Arginine Hydrochloride, USP; and 0.025 mg Polysorbate 20 in Water for Injection, USP at a pH of approximately 4.8.

In a particular embodiment, the pharmaceutical composition comprises Exenatide injection (BYDUREON®). Exenatide injection (BYDUREON®) is a glucagon-like peptide-1 (GLP-1) receptor agonist indicated as an adjunct to diet and exercise to improve glycemic control in adults with type 2 diabetes mellitus in multiple clinical settings. BYDUREON® is an extended-release formulation of exenatide.

Exenatide, a 39-amino acid synthetic peptide amide with an empirical formula of $C_{184}H_{282}N_{50}O_{60}S$ and a molecular weight of 4186.6 Daltons, is typically administered in a dose of 2 mg by subcutaneous injection once every seven days (weekly), at any time of day and with or without meals. Exenatide is administered immediately after the powder is suspended.

Exenatide is a white to off-white powder that is available in a dosage strength of 2 mg exenatide per vial. Exenatide is incorporated in an extended release microsphere formulation containing the 50:50 poly(D,L-lactide-co-glycolide) polymer (37.2 mg per vial) along with sucrose (0.8 mg per vial). The powder must be suspended in the diluent prior to injection. The diluent is provided in a prefilled syringe. Each prefilled syringe delivers 0.65 mL of the diluent as a clear, colorless to pale yellow solution composed of carboxymethylcellulose sodium (23 mg), polysorbate 20 (0.77 mg), sodium phosphate monobasic monohydrate (0.74 mg), sodium phosphate dibasic heptahydrate (0.62 mg), sodium chloride (5.0 mg), and water for injection.

In a particular embodiment, the pharmaceutical composition comprises Darbepoetin alfa (ARANESP®). Darbepoetin alfa (ARANESP®) is an erythropoiesis-stimulating agent (ESA) indicated for the treatment of anemia due to Chronic Kidney Disease (CKD) in patients on dialysis and patients not on dialysis. Darbepoetin alfa is produced in Chinese hamster ovary (CHO) cells by recombinant DNA technology. ARANESP® is a 165-amino acid protein that differs from recombinant human erythropoietin in containing 5 N-linked oligosaccharide chains, whereas recombinant human erythropoietin contains 3 chains. The 2 additional N-glycosylation sites result from amino acid substitutions in the erythropoietin peptide backbone. The approximate molecular weight of darbepoetin alfa is 37,000 daltons.

The recommended starting dose for CKD patients on dialysis is 0.45 mcg/kg intravenously or subcutaneously weekly, or 0.75 mcg/kg intravenously or subcutaneously every 2 weeks. Intravenous route is recommended for patients on hemodialysis. The recommended starting dose for patients with CKD not on dialysis is 0.45 mcg/kg intravenously or subcutaneously at 4 week intervals. The recommended starting dose for cancer patients on chemotherapy is 2.25 mcg/kg subcutaneously weekly, or 500 mcg subcutaneously every 3 weeks.

Darbepoetin alfa is provided as single-dose vials: 25, 40, 60, 100, 200, 300, and 500 mcg/1 mL, and 150 mcg/0.75 mL or Single-dose prefilled syringes: 25 mcg/0.42 mL, 40 mcg/,0.4 mL, 60 mcg/0.3 mL, 100 mcg/0.5 mL, 150 mcg/0.3 mL, 200 mcg/0.4 mL, 300 mcg/0.6 mL, and 500 mcg/1 mL.

Darbepoetin alfa is formulated as a sterile, colorless, preservative-free solution containing polysorbate for intravenous or subcutaneous administration. Each 1 mL contains polysorbate 80 (0.05 mg), sodium chloride (8.18 mg), sodium phosphate dibasic anhydrous (0.66 mg), and sodium phosphate monobasic monohydrate (2.12 mg) in Water for Injection, USP (pH 6.2+/−0.2).

In a particular embodiment, the pharmaceutical composition comprises Influenza virus vaccine (FLUZONE®) Intradermal. Influenza virus vaccine (FLUZONE®) Intradermal is indicated for active immunization against influenza disease caused by influenza virus subtypes A and type B contained in the vaccine. FLUZONE® Intradermal is approved for use in persons 18 through 64 years of age. FLUZONE® Intradermal (Influenza Virus Vaccine) for intradermal injection is an inactivated influenza virus vaccine, prepared from influenza viruses propagated in embryonated chicken eggs.

The virus-containing allantoic fluid is harvested and inactivated with formaldehyde. Influenza virus is concentrated and purified in a linear sucrose density gradient solution using a continuous flow centrifuge. The virus is then chemically disrupted using a non-ionic surfactant, Octylphenol Ethoxylate (Triton® X-100), producing a "split virus". The split virus is further purified and then suspended in sodium phosphate-buffered isotonic sodium chloride solution. The FLUZONE® Intradermal process uses an additional concentration factor after the ultrafiltration step in order to obtain a higher hemagglutinin (HA) antigen concentration.

FLUZONE® Intradermal is a clear, slightly opalescent suspension for injection. Neither antibiotics nor preservative are used in the manufacture of FLUZONE® Intradermal. FLUZONE® Intradermal is standardized according to United States Public Health Service requirements and is formulated to contain HA of each of the following three influenza strains recommended for the 2012-2013 influenza season: A/California/07/2009 NYMC X-179A (H1N1), A/Victoria/361/2011 IVR-165 (H3N2) and B/Texas/6/2011 (a B/Wisconsin/1/2010-like virus). The amounts of HA and other ingredients per dose of vaccine are listed in Table 2.

TABLE 2

Fluzone Intradermal Ingredients

| Ingredient | Quantity (per dose) Fluzone Intradermal 0.1 mL Dose |
|---|---|
| Active Substance: Split influenza virus, inactivated strains[a]: | 27 mcg HA total |
| A (H1N1) | 9 mcg HA |
| A (H3N2) | 9 mcg HA |
| B | 9 mcg HA |
| Other: | |
| Sodium phosphate-buffered isotonic sodium chloride solution | QS[b] to appropriate volume |
| Formaldehyde | ≤20 mcg |
| Octylphenol Ethoxylate | ≤50 mcg |
| Gelatin | None |
| Preservative | None |

[a]per United States Public Health Service (USPHS) requirement
[b]Quantity Sufficient In a particular embodiment, the pharmaceutical composition comprises Antihemophilic Factor VIII (KOGENATE® FS). Antihemophilic Factor VIII (KOGENATE® FS) is an Antihemophilic Factor (Recombinant) indicated for control and prevention of bleeding episodes in adults and children (0-16 years) with hemophilia A; peri-operative management in adults and children with hemophilia A; and routine prophylaxis to reduce the frequency of bleeding episodes and the risk of joint damage in children with hemophilia A with no preexisting joint damage.

Antihemophilic Factor VIII is a coagulation factor VIII produced by recombinant DNA technology. It is produced by Baby Hamster Kidney (BHK) cells into which the human factor VIII gene has been introduced. The cell culture medium contains Human Plasma Protein Solution (HPPS) and recombinant insulin, but does not contain any proteins derived from animal sources. KOGENATE® FS is a purified glycoprotein consisting of multiple peptides including an 80 kD and various extensions of the 90 kD subunit. It has the same biological activity as factor VIII derived from human plasma. No human or animal proteins, such as albumin, are added during the purification and formulation processes of Antihemophilic Factor VIII.

The purification process includes a solvent/detergent virus inactivation step in addition to the use of the purification methods of ion exchange chromatography, monoclonal antibody immunoaffinity chromatography, along with other chromatographic steps designed to purify recombinant factor VIII and remove contaminating substances. Additionally, the manufacturing process was investigated for its capacity to decrease the infectivity of an experimental agent of transmissible spongiform encephalopathy (TSE), considered as a model for the vCJD and CJD agents. Several of the individual production and raw material preparation steps in the Antihemophilic Factor VIII manufacturing process have been shown to decrease TSE infectivity of that experimental model agent. TSE reduction steps include the Fraction II+III separation step for HPPS (6.0 log 10) and an anion exchange chromatography step (3.6 log 10).

Antihemophilic Factor VIII is for intravenous use only. Each vial of Antihemophilic Factor VIII contains the labeled amount of recombinant factor VIII in international units (IU). For control and prevention of bleeding episodes and peri-operative management doses administered should be titrated to the patient's clinical response. The Dose (units)=body weight (kg) x desired factor VIII rise (IU/dL or % of normal)×0.5 (IU/kg per IU/dL). The frequency of intravenous injection of the reconstituted product is determined by the type of bleeding episode and the recommendation of the treating physician. For routine prophylaxis in children with no pre-existing joint damage, the recommended dose is 25 IU/kg every other day.

Antihemophilic Factor VIII is formulated with the following as stabilizers [see Table 3] in the final container and is then lyophilized. The final product is a sterile, nonpyrogenic, preservative-free, powder preparation for intravenous (IV) injection.

TABLE 3

Antihemophilic Factor VIII Formulation Stabilizers

| Stabilizer | 250 IU, 500 IU, 1000 IU | 2000 IU, 3000 IU |
|---|---|---|
| Sucrose | 0.9-1.3% | 0.9-1.2% |
| Glycine | 21-25 mg/mL | 20-24 mg/mL |
| Histidine | 18-23 mmol/L | 17-22 mmol/L |

The following inactive ingredients/excipients are also contained in the final product:

TABLE 4

Antihemophilic Factor VIII Formulation
Inactive Ingredients/Excipients

| Inactive Ingredient/ Excipient | 250 IU, 500 IU, 1000 IU | 2000 IU, 3000 IU |
|---|---|---|
| Sodium | 27-36 mEq/L | 26-34 mEq/L |
| Calcium | 2.0-3.0 mmol/L | 1.9-2.9 mmol/L |
| Chloride | 32-40 mEq/L | 31-38 mEq/L |
| Polysorbate 80 | 64-96 µg/mL | 64-96 µg/mL |
| Sucrose | 28 mg/vial | 52 mg/vial |
| Imidazole, tri-n-butyl phosphate, and copper | Trace amounts | Trace amounts |

In a particular embodiment, the pharmaceutical composition comprises Natalizumab (TYSABRI®). Natalizumab (TYSABRI®) is an integrin receptor antagonist indicated for treatment of Multiple Sclerosis (MS). Natalizumab is indicated as monotherapy for the treatment of patients with relapsing forms of multiple sclerosis to delay the accumulation of physical disability and reduce the frequency of clinical exacerbations. Natalizumab is generally recommended for patients who have had an inadequate response to, or are unable to tolerate, an alternate MS therapy.

Natalizumab is also indicated in Crohn's Disease (CD), for inducing and maintaining clinical response and remission in adult patients with moderately to severely active Crohn's disease with evidence of inflammation who have had an inadequate response to, or are unable to tolerate, conventional CD therapies and inhibitors of TNF-α. In CD, Natalizumab should not be used in combination with immunosuppressants or inhibitors of TNF-α.

Natalizumab, having a molecular weight of 149 kilodaltons, is a recombinant humanized IgG4K monoclonal antibody produced in murine myeloma cells. Natalizumab contains human framework regions and the complementarity-determining regions of a murine antibody that binds to α4-integrin. Natalizumab is supplied as a sterile, colorless, and clear to slightly opalescent concentrate for intravenous infusion.

Natalizumab is administered as a 300 mg infused intravenously over approximately one hour, every four weeks. Natalizumab is not to be administered as an intravenous push or bolus. Natalizumab solution must be administered within 8 hours of preparation. In CD, discontinue in patients that have not experienced therapeutic benefit by 12 weeks of induction therapy, and in patients that cannot discontinue chronic concomitant steroids within six months of starting therapy.

Each 15 mL dose contains 300 mg natalizumab; 123 mg sodium chloride, USP; 17.0 mg sodium phosphate, monobasic, monohydrate, USP; 7.24 mg sodium phosphate, dibasic, heptahydrate, USP; 3.0 mg polysorbate 80, USP/NF, in water for injection, USP at pH 6.1.

In a particular embodiment, the pharmaceutical composition comprises Interferon beta-1a (REBIF®). Interferon beta-1a (REBIF®) has been approved for the treatment of relapsing forms of multiple sclerosis (MS). Interferon beta-1a has been shown to decrease the frequency of clinical exacerbations and delay the accumulation of physical disability in patients with MS, although the specific interferon-induced proteins and mechanisms by which interferon beta-1a exerts its effects in multiple sclerosis patients have not been fully defined.

Interferon beta-1a is a 166 amino acid glycoprotein with a molecular weight of approximately 22,500 daltons. It is produced by recombinant DNA technology using genetically engineered Chinese Hamster Ovary cells into which the human interferon beta gene has been introduced. The amino acid sequence of Interferon beta-1a is identical to that of natural fibroblast derived human interferon beta. Natural interferon beta and interferon beta-1a are both glycosylated with each containing a single N-linked complex carbohydrate moiety.

Using a reference standard calibrated against the World Health Organization natural interferon beta standard (Second International Standard for Interferon, Human Fibroblast GB 23 902 531), Interferon beta-1a has a specific activity of approximately 270 million international units (MIU) of antiviral activity per mg of interferon beta-1a determined specifically by an in vitro cytopathic effect bioassay using WISH cells and Vesicular Stomatitis virus. interferon beta-1a 8.8 mcg, 22 mcg and 44 mcg contain approximately 2.4 MIU, 6 MIU or 12 MIU, respectively, of antiviral activity using this method.

Interferon beta-1a is supplied as a sterile, preservative-free solution packaged in graduated, ready to use in 0.2 mL or 0.5 mL prefilled syringes with 29-gauge, 0.5 inch needle for subcutaneous injection. The following package presentations are available: interferon beta-1a Titration Pack consisting of six interferon beta-1a 8.8 mcg prefilled syringes and six interferon beta-1a 22 mcg prefilled syringes; Interferon beta-1a) 22 mcg Prefilled Syringe and interferon beta-1a 44 mcg Prefilled Syringe.

Interferon beta-1a is formulated as a sterile solution in a prefilled syringe intended for subcutaneous (sc) injection. Each 0.5 mL (0.5 cc) of interferon beta-1a contains either 22 mcg or 44 mcg of interferon beta-1a, 2 or 4 mg albumin (human) USP, 27.3 mg mannitol USP, 0.4 mg sodium acetate, Water for Injection USP. Each 0.2 mL (0.2 cc) of interferon beta-1a contains 8.8 mcg of interferon beta-1a, 0.8 mg albumin (human) USP, 10.9 mg mannitol USP, 0.16 mg sodium acetate, and Water for Injection USP.

In a particular embodiment, the pharmaceutical composition comprises Coagulation Factor VIIa Recombinant (NOVOSEVEN®). Coagulation Factor VIIa Recombinant (NOVOSEVEN®) is indicated for the treatment of bleeding episodes in hemophilia A or B with inhibitors and in acquired hemophilia, the prevention of bleeding in surgical interventions or invasive procedures in hemophilia A or B with inhibitors and in acquired hemophilia, in treatment of bleeding episodes in congenital FVII deficiency, and in prevention of bleeding in surgical interventions or invasive procedures in congenital FVII deficiency.

Coagulation Factor VIIa Recombinant, having a molecular weight of 50 K Daltons, is recombinant human coagulation Factor VIIa (rFVIIa), intended for promoting hemostasis by activating the extrinsic pathway of the coagulation cascade. Coagulation Factor VIIa Recombinant is a vitamin K-dependent glycoprotein consisting of 406 amino acid residues. Coagulation Factor VIIa Recombinant is structurally similar to human plasma-derived Factor VIIa. The gene for human Factor VII is cloned and expressed in baby hamster kidney cells (BHK cells). Recombinant FVII is secreted into the culture media (containing newborn calf serum) in its single-chain form and then proteolytically converted by autocatalysis to the active two-chain form, rFVIIa, during a chromatographic purification process. The purification process has been demonstrated to remove exogenous viruses (MuLV, SV40, Pox virus, Reovirus, BEV, IBR virus).

Coagulation Factor VIIa Recombinant is for intravenous bolus injection only. After reconstitution, administer within 3 hours; do not freeze or store in syringes. Coagulation Factor VIIa Recombinant should be administered to patients only under the supervision of a physician experienced in the treatment of bleeding disorders.

Coagulation Factor VIIa Recombinant is provided as a lyophilized powder in single-use vials: 1, 2, 5, or 8 mg rFVIIa. After reconstitution with specified volume of histidine diluent, each vial contains 1 mg/mL (1000 micrograms/mL) of recombinant FVIIa. Each vial of lyophilized drug contains the following:

TABLE 5

Formulation of Coagulation Factor VIIa Recombinant

| Contents | 1 mg Vial | 2 mg Vial | 5 mg Vial | 8 mg Vial |
|---|---|---|---|---|
| rFVIIa | 1000 micrograms | 2000 micrograms | 5000 micrograms | 8000 micrograms |
| sodium chloride* | 2.34 mg | 4.68 mg | 11.7 mg | 18.72 mg |
| calcium chloride dihydrate* | 1.47 mg | 2.94 mg | 7.35 mg | 11.76 mg |
| glycylglycine | 1.32 mg | 2.64 mg | 6.60 mg | 10.56 mg |
| polysorbate 80 | 0.07 mg | 0.14 mg | 0.35 mg | 0.56 mg |
| mannitol | 25 mg | 50 mg | 125 mg | 200 mg |
| Sucrose | 10 mg | 20 mg | 50 mg | 80 mg |
| Methionine | 0.5 mg | 1.0 mg | 2.5 mg | 4 mg |

*per mg of rFVIIa: 0.4 mEq sodium, 0.01 mEq calcium

The diluent for reconstitution of Coagulation Factor VIIa Recombinant is a 10 mmol solution of histidine in water for injection and is supplied as a clear colorless solution. After reconstitution with the appropriate volume of histidine diluent, each vial contains approximately 1 mg/mL NOVOSEVEN® RT (corresponding to 1000 micrograms/mL). The reconstituted vials have a pH of approximately 6.0 in sodium chloride (2.3 mg/mL), calcium chloride dihydrate (1.5 mg/mL), glycylglycine (1.3 mg/mL), polysorbate 80 (0.1 mg/mL), mannitol (25 mg/mL), sucrose (10 mg/mL), methionine (0.5 mg/mL), and histidine (1.6 mg/mL). The reconstituted product is a clear colorless solution which contains no preservatives. Coagulation Factor VIIa Recombinant contains trace amounts of proteins derived from the manufacturing and purification processes such as mouse IgG (maximum of 1.2 ng/mg), bovine IgG (maximum of 30 ng/mg), and protein from BHK-cells and media (maximum of 19 ng/mg).

In a particular embodiment, the pharmaceutical composition comprises Insulin detemir [rDNA origin] injection (LEVEMIR®). Insulin detemir [rDNA origin] injection (LEVEMIR®) is a long-acting human insulin analog indicated to improve glycemic control in adults and children with diabetes mellitus.

The starting dose should be individualized based on the type of diabetes and whether the patient is insulin-naïve. Insulin detemir [rDNA origin] injection is administered subcutaneously once daily or in divided doses twice daily. Once daily administration should be given with the evening meal or at bedtime.

Insulin detemir [rDNA origin] injection, having the molecular formula of $C_{267}H_{402}O_{76}N_{64}S_6$ and a molecular weight of 5916.9 is a sterile solution of insulin detemir for use as a subcutaneous injection. Insulin detemir is a long-acting (up to 24-hour duration of action) recombinant human insulin analog. Insulin detemir [rDNA origin] injection is produced by a process that includes expression of recombinant DNA in Saccharomyces cerevisiae followed by chemical modification. Insulin detemir differs from human insulin in that the amino acid threonine in position B30 has been omitted, and a C14 fatty acid chain has been attached to the amino acid B29.

Insulin detemir [rDNA origin] injection is available as a clear, colorless, aqueous, neutral sterile solution. Each milliliter of insulin detemir [rDNA origin] injection contains 100 units (14.2 mg/mL) insulin detemir, 65.4 mcg zinc, 2.06 mg m-cresol, 16.0 mg glycerol, 1.80 mg phenol, 0.89 mg disodium phosphate dihydrate, 1.17 mg sodium chloride, and water for injection. Hydrochloric acid and/or sodium hydroxide may be added to adjust pH. Insulin detemir [rDNA origin] injection has a pH of approximately 7.4.

In a particular embodiment, the pharmaceutical composition comprises Certolizumab pegol (CIMZIA®). Certolizumab pegol (CIMZIA®) is a tumor necrosis factor (TNF) blocker indicated for reducing signs and symptoms of Crohn's disease and maintaining clinical response in adult patients with moderately to severely active disease who have had an inadequate response to conventional therapy, and for the treatment of adults with moderately to severely active rheumatoid arthritis.

Certolizumab pegol, having a molecular weight of approximately 91 kiloDaltons, is a TNF blocker. CIMZIA® is a recombinant, humanized antibody Fab' fragment, with specificity for human tumor necrosis factor alpha (TNFα), conjugated to an approximately 40 kDa polyethylene glycol (PEG2MAL40K). The Fab' fragment is manufactured in E. coli and is subsequently subjected to purification and conjugation to PEG2MAL40K, to generate certolizumab pegol. The Fab' fragment is composed of a light chain with 214 amino acids and a heavy chain with 229 amino acids.

Certolizumab pegol is administered by subcutaneous injection. The initial dose of Certolizumab pegol is 400 mg (given as two subcutaneous injections of 200 mg). For Crohn's Disease, certolizumab pegol is administered as 400 mg initially and at Weeks 2 and 4. If response occurs, follow with 400 mg every four weeks. For Rheumatoid Arthritis, certolizumab pegol is administered as 400 mg initially and at Weeks 2 and 4, followed by 200 mg every other week; for maintenance dosing, 400 mg every 4 weeks can be considered.

Certolizumab pegol is supplied as either a sterile, white, lyophilized powder for solution or as a sterile, solution in a single-use prefilled 1 mL glass syringe for subcutaneous injection. After reconstitution of the lyophilized powder with 1 mL sterile Water for Injection, USP, the resulting pH is approximately 5.2. Each single-use vial provides approximately 200 mg certolizumab pegol, 0.9 mg lactic acid, 0.1 mg polysorbate, and 100 mg sucrose. Each single-use prefilled syringe of certolizumab pegol delivers 200 mg in 1 mL of solution with a pH of approximately 4.7 for subcutaneous use. Each 1 mL syringe of certolizumab pegol contains certolizumab pegol (200 mg), sodium acetate (1.36 mg), sodium chloride (7.31 mg), and Water for Injection, USP.

In a particular embodiment, the pharmaceutical composition comprises Carfilzomib (KYPROLIS®). Carfilzomib (KYPROLIS®), the tetrapeptide epoxyketone shown below, is a proteasome inhibitor available for intravenous use and indicated for the treatment of patients with multiple myeloma who have received at least two prior therapies including bortezomib and an immunomodulatory agent and have demonstrated disease progression on or within 60 days of completion of the last therapy.

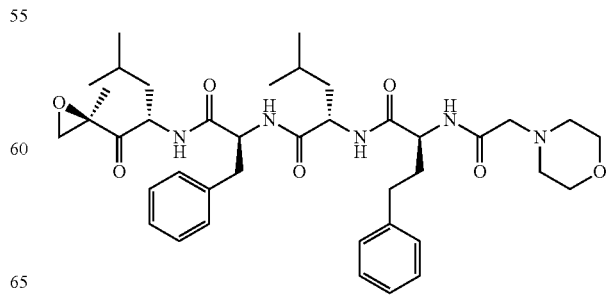

Carfilzomib is a crystalline substance with a molecular weight of 719.9. The molecular formula is $C_{40}H_{57}N_5O_7$. Carfilzomib is practically insoluble in water, and very slightly soluble in acidic conditions. Carfilzomib is manufactured as a sterile, white to off-white lyophilized powder and is available as a single-use vial.

Each vial of carfilzomib contains 60 mg of carfilzomib, 3000 mg sulfobutylether beta-cyclodextrin, 57.7 mg citric acid, and sodium hydroxide for pH adjustment (target pH 3.5). Carfilzomib is typically administered intravenously over 2 to 10 minutes, on two consecutive days, each week for three weeks (Days 1, 2, 8, 9, 15, and 16), followed by a 12-day rest period (Days 17 to 28). Each 28-day period is considered one treatment cycle.

In a particular embodiment, the pharmaceutical composition comprises insulin human recombinant (HUMULIN® R U-100) or concentrated insulin human recombinant (HUMULIN® R U-500). Insulin human recombinant (HUMULIN® R U-100) or concentrated insulin human recombinant (HUMULIN® R U-500) are both polypeptide hormones structurally identical to human insulin synthesized through rDNA technology in a special non-disease-producing laboratory strain of Escherichia coli bacteria. These insulin human recombinants have the empirical formula $C_{257}H_{383}N_{65}O_{77}S_6$ and a molecular weight of 5808.

Both of these man-made insulin products are used to treat diabetes, and, like other insulin products, each of them function by helping sugar (glucose) get into cells. Because both insulin human recombinant U-100 and U-500 are short-acting insulins, they are usually used in combination with a medium- or long-acting insulin products injected under the skin (subcutaneously) to control high blood sugar.

Insulin human recombinant U-100 is typically manufactured as a sterile, clear, aqueous, and colorless solution that contains human insulin (rDNA origin) 100 units/mL, glycerin 16 mg/mL and metacresol 2.5 mg/mL, endogenous zinc (approximately 0.015 mg/100 units) and water for injection. The pH is 7.0 to 7.8. Sodium hydroxide and/or hydrochloric acid may be added during manufacture to adjust the pH. Insulin human recombinant U-100 is available in both 3 mL and 10 mL vials. Unlike insulin human recombinant U-500, intravenous administration of insulin human recombinant U-100 is possible under close medical supervision with close monitoring of blood glucose and potassium levels to avoid hypoglycemia and hypokalemia.

Insulin human recombinant U-500 is typically manufactured as a sterile, clear, aqueous and colorless solution that contains human insulin (rDNA origin) 500 units/mL, glycerin 16 mg/mL, metacresol 2.5 mg/mL and zinc oxide to supplement the endogenous zinc to obtain a total zinc content of 0.017 mg/100 units, and water for injection. The pH is 7.0 to 7.8. Sodium hydroxide and/or hydrochloric acid may be added during manufacture to adjust the pH. Insulin human recombinant U-500 is available in 20 mL vials.

In a particular embodiment, the pharmaceutical composition comprises Ranibizumab injection (LUCENTIS®). Ranibizumab injection (LUCENTIS®) is a recombinant humanized IgG1 kappa isotype monoclonal antibody fragment designed for intraocular use. Ranibizumab is currently used to treat age-related macular degeneration (a serious eye condition) and is also used to help prevent decreased vision and blindness. Ranibizumab, which lacks an Fc region, has a molecular weight of approximately 48 kilodaltons and is produced by an E. coli expression system in a nutrient medium containing the antibiotic tetracycline. Tetracycline is not detectable in the final product.

Ranibizumab binds to and inhibits the biologic activity of human vascular endothelial growth factor A (VEGF-A). VEGF-A has been shown to cause neovascularization and leakage in models of ocular angiogenesis and vascular occlusion and is thought to contribute to pathophysiology of neovascular AMD, macular edema following RVO, and DME. The binding of ranibizumab to VEGF-A prevents the interaction of VEGF-A with its receptors (VEGFR1 and VEGFR2) on the surface of endothelial cells, reducing endothelial cell proliferation, vascular leakage, and new blood vessel formation.

Ranibizumab is typically manufactured in a sterile, colorless to pale yellow solution in a single-use glass vial. Ranibizumab is typically supplied as a preservative-free, sterile solution in a single-use glass vial designed to deliver 0.05 mL of 10 mg/mL Ranibizumab (0.5 mg dose vial) or 6 mg/mL Ranibizumab (0.3 mg dose vial) aqueous solution with 10 mM histidine HCl, 10% α,α-trehalose dihydrate, and 0.01% polysorbate 20, with a pH of 5.5. Ranibizumab is available in both single-use glass vials for the 10 mg/mL and 6 mg/mL solutions.

In a particular embodiment, the pharmaceutical composition comprises Immune Globulin Intravenous (Human), 10% Caprylate/Chromatography Purified (GAMUNEX®). Immune Globulin Intravenous (Human), 10% Caprylate/Chromatography Purified (GAMUNEX®) exists as a ready-to-use sterile solution of human immune globulin protein for intravenous administration. GAMUNEX® is used primarily to treat primary immune deficiency conditions and includes treating people with chronic inflammatory demyelinating polyneuropathy (CIDP), primary immunodeficiency (PI), or idiopathic thrombocytopenic purpura (ITP).

Immune globulin intravenous human 10% consists of 9%-11% protein in 0.16-0.24 M glycine. Not less than 98% of the protein has the electrophoretic mobility of gamma globulin. The buffering capacity of immune globulin intravenous (human) 10% is 35.0 mEq/L (0.35 mEq/g protein) Immune globulin intravenous human 10% contains trace levels of fragments, IgA (average 0.046 mg/mL), and IgM. The distribution of IgG subclasses is similar to that found in normal serum Immune globulin intravenous human 10% doses of 1 g/kg correspond to a glycine dose of 0.15 g/kg.

Immune globulin intravenous human 10% is made from large pools of human plasma by a combination of cold ethanol fractionation, caprylate precipitation and filtration, and anion-exchange chromatography. Isotonicity is achieved by the addition of glycine. Immune globulin intravenous human 10% is incubated in the final container (at the low pH of 4.0-4.3), for a minimum of 21 days at 23° to 27° C. The product is intended for intravenous administration.

In a particular embodiment, the pharmaceutical composition comprises GARDASIL®, a Human Papillomavirus Quadrivalent (Types 6, 11, 16, and 18) Vaccine, Recombinant. GARDASIL®, a Human Papillomavirus Quadrivalent (Types 6, 11, 16, and 18) Vaccine, Recombinant is a non-infectious recombinant quadrivalent vaccine prepared from the purified virus-like particles (VLPs) of the major capsid (L1) protein of HPV Types 6, 11, 16, and 18. In girls and women, quadrivalent human papillomavirus (types 6, 11, 16, 18) recombinant vaccine is a vaccine indicated for girls and women 9 through 26 years of age for the prevention of the following diseases caused by Human Papillomavirus (HPV) types included in the vaccine: Cervical, vulvar, and vaginal cancer caused by HPV types 16 and 18; Genital warts (condyloma acuminata) caused by HPV types 6 and 11; Cervical intraepithelial neoplasia (CIN) grade 2/3 and Cervical adenocarcinoma in situ (AIS); Cervical intraepithelial neoplasia (CIN) grade 1; Vulvar intraepithelial neoplasia (VIN) grade 2 and grade 3; and Vaginal intraepithelial neoplasia (VaIN) grade 2 and grade 3. Quadrivalent human papillomavirus (types 6, 11, 16, 18) recombinant vaccine is also indicated in boys and men 9 through 26 years of age for the prevention of genital warts (condyloma acuminata) caused by HPV types 6 and 11.

The L1 proteins are produced by separate fermentations in recombinant *Saccharomyces cerevisiae* and self-assembled into VLPs. The fermentation process involves growth of *S. cerevisiae* on chemically-defined fermentation media which include vitamins, amino acids, mineral salts, and carbohydrates. The VLPs are released from the yeast cells by cell disruption and purified by a series of chemical and physical methods. The purified VLPs are adsorbed on preformed aluminum-containing adjuvant (Amorphous Aluminum Hydroxyphosphate Sulfate). The quadrivalent HPV VLP vaccine is a sterile liquid suspension that is prepared by combining the adsorbed VLPs of each HPV type and additional amounts of the aluminum-containing adjuvant and the final purification buffer.

Quadrivalent human papillomavirus types 6, 11, 16, 18 recombinant vaccine is a sterile suspension for intramuscular administration. Each 0.5-mL dose contains approximately 20 mcg of HPV 6 L1 protein, 40 mcg of HPV 11 L1 protein, 40 mcg of HPV 16 L1 protein, and 20 mcg of HPV 18 L1 protein. Each 0.5-mL dose of the vaccine contains approximately 225 mcg of aluminum (as Amorphous Aluminum Hydroxyphosphate Sulfate adjuvant), 9.56 mg of sodium chloride, 0.78 mg of L-histidine, 50 mcg of polysorbate 80, 35 mcg of sodium borate, <7 mcg yeast protein/dose, and water for injection. The product does not contain a preservative or antibiotics. Quadrivalent human papillomavirus types 6, 11, 16, 18 recombinant vaccine is a available in 0.5 mL single-dose vials.

In a particular embodiment, the pharmaceutical composition comprises PEDIARIX® [Diphtheria and Tetanus Toxoids and Acellular Pertussis Adsorbed, Hepatitis B (Recombinant) and Inactivated Poliovirus Vaccine Combined]. PEDIARIX® is a noninfectious, sterile, multivalent vaccine for intramuscular administration. Diphtheria and Tetanus Toxoids and Acellular Pertussis Adsorbed, Hepatitis B (Recombinant) and Inactivated Poliovirus Vaccine Combined is indicated for active immunization against diphtheria, tetanus, pertussis (whooping cough), all known subtypes of hepatitis B virus, and poliomyelitis caused by poliovirus Types 1, 2, and 3 as a three-dose primary series in infants born of HBsAg-negative mothers, beginning as early as 6 weeks of age.

Diphtheria and Tetanus Toxoids and Acellular Pertussis Adsorbed, Hepatitis B (Recombinant) and Inactivated Poliovirus Vaccine Combined contains diphtheria and tetanus toxoids, 3 pertussis antigens (inactivated pertussis toxin [PT] and formaldehyde-treated filamentous hemagglutinin [FHA] and pertactin [69 kiloDalton outer membrane protein]), hepatitis B surface antigen, plus poliovirus Type 1 (Mahoney), Type 2 (MEF-1), and Type 3 (Saukett). The diphtheria toxoid, tetanus toxoid, and pertussis antigens are the same as those in INFANRIX® (Diphtheria and Tetanus Toxoids and Acellular Pertussis Vaccine Adsorbed). The hepatitis B surface antigen is the same as that in ENGERIX-B® [Hepatitis B Vaccine (Recombinant)].

Diphtheria and Tetanus Toxoids and Acellular Pertussis Adsorbed, Hepatitis B (Recombinant) and Inactivated Poliovirus Vaccine Combined is supplied as a turbid white suspension in single-dose (0.5 mL) vials and disposable prefilled syringes. A 0.5-mL dose also contains 4.5 mg of NaCl and aluminum adjuvant (not more than 0.85 mg aluminum by assay). Each dose also contains ≤100 mcg of residual formaldehyde and ≤100 mcg of polysorbate 80 (Tween 80). Neomycin sulfate and polymyxin B are used in the polio vaccine manufacturing process and may be present in the final vaccine at ≤0.05 ng neomycin and 0.01 ng polymyxin B per dose. The procedures used to manufacture the HBsAg antigen result in a product that contains ≤5% yeast protein.

In a particular embodiment, the pharmaceutical composition comprises Bortezomib for Injection (VELCADE®). Bortezomib for Injection (VELCADE®), shown below, is a modified dipeptidyl boronic acid antineoplastic agent available for the treatment of patients with multiple myeloma and for the treatment of patients with mantle cell lymphoma who have received at least 1 prior therapy.

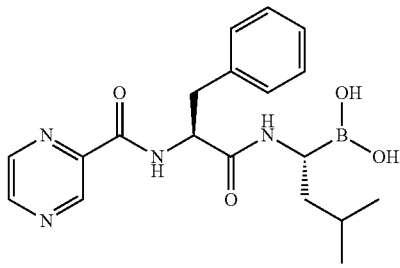 [SMILES: CC(C)C[C@H](NC(=O)[C@H](Cc1ccccc1)NC(=O)c1cnccn1)B(O)O]

Bortezomib is produced for intravenous injection or subcutaneous use. The product is provided as a mannitol boronic ester which, in reconstituted form, consists of the mannitol ester in equilibrium with its hydrolysis product, the monomeric boronic acid. The drug substance exists in its cyclic anhydride form as a trimeric boroxine.

The chemical name for bortezomib, the monomeric boronic acid, is [(1R)-3-methyl-1-[[(2 S)-1-oxo-3-phenyl-2-[(pyrazinylcarbonyl)amino]propyl]amino]butyl] boronic acid and has a molecular weight of 384.24. The molecular formula is $C_{19}H_{25}BN_4O_4$. The solubility of bortezomib, as the monomeric boronic acid, in water is 3.3 to 3.8 mg/mL in a pH range of 2 to 6.5.

Bortezomib for Injection is indicated Bortezomib is supplied as individually cartoned 10 mL vials containing 3.5 mg of bortezomib as a sterile white to off-white cake or lyophilized powder. Inactive ingredient: 35 mg mannitol, USP.

In a particular embodiment, the pharmaceutical composition comprises Peginterferon alfa-2a (PEGASYS®). Peginterferon alfa-2a (PEGASYS®), is a covalent conjugate of recombinant alfa-2a interferon (approximate molecular weight [MW] 20,000 daltons) with a single branched bis-monomethoxy polyethylene glycol (PEG) chain (approximate MW 40,000 daltons). The PEG moiety is linked at a single site to the interferon alfa moiety via a stable amide bond to lysine. Peginterferon alfa-2a, alone or in combination with Ribavirin, is indicated for the treatment of adults with chronic hepatitis C (CHC) virus infection who have compensated liver disease and have not been previously treated with interferon alpha.

Peginterferon alfa-2a has an approximate molecular weight of 60,000 daltons. Interferon alfa-2a is produced using recombinant DNA technology in which a cloned human leukocyte interferon gene is inserted into and expressed in *Escherichia coli*.

Efficacy has been demonstrated in subjects with compensated liver disease and histological evidence of cirrhosis (Child-Pugh class A) and in subjects with clinically stable HIV disease and CD4 count greater than 100 cells/mm$^3$ Peginterferon alfa-2a is also indicated for the treatment of adult patients with HBeAg positive and HBeAg negative chronic hepatitis B who have compensated liver disease and evidence of viral replication and liver inflammation.

Peginterferon alfa-2a is a sterile, preservative-free, colorless to light yellow injectable solution administered subcutaneously and available in two forms: a 180 mcg/1.0 mL vial and a 180 mcg/0.5 mL prefilled syringe.

Each vial contains approximately 1.2 mL of solution to deliver 1.0 mL of drug product. Subcutaneous (sc) administration of 1.0 mL of 180 meg of drug product (expressed as the amount of interferon alfa-2a) also contains acetic acid (0.05 mg), benzyl alcohol (10.0 mg), polysorbate 80 (0.05 mg), sodium acetate trihydrate (2.62 mg), and sodium chloride (8.0 mg) at pH 6.0±0.5.

Each syringe contains 0.6 mL of solution to deliver 0.5 mL of drug product. Subcutaneous (sc) administration of 0.5 mL delivers 180 meg of drug product (expressed as the amount of interferon alfa-2a) also contains acetic acid (0.0231 mg), benzyl alcohol (5.0 mg), polysorbate 80 (0.025 mg), sodium acetate trihydrate (1.3085 mg), and sodium chloride (4.0 mg) at pH 6.0±0.5.

In a particular embodiment, the pharmaceutical composition comprises Hepatitis A & Hepatitis B (Recombinant) Vaccine (TWINRIX®) which is a mixture of two earlier vaccines—HAVRIX®, an inactivated-virus Hepatitis A vaccine, and ENGERIX-B®, a recombinant Hepatitis B vaccine. Hepatitis A & Hepatitis B (Recombinant) Vaccine is a vaccine indicated for active immunization against disease caused by hepatitis A virus and infection by all known subtypes of hepatitis B virus.

A 1-mL dose of vaccine contains 720 ELISA Units of inactivated hepatitis A virus and 20 mcg of recombinant HBsAg protein. One dose of vaccine also contains 0.45 mg of aluminum in the form of aluminum phosphate and aluminum hydroxide as adjuvants, amino acids, sodium chloride, phosphate buffer, polysorbate 20, and Water for Injection. From the manufacturing process each 1-mL dose of Hepatitis A & Hepatitis B (Recombinant) Vaccine also contains residual formalin (not more than 0.1 mg), MRC-5 cellular proteins (not more than 2.5 mcg), neomycin sulfate (an aminoglycoside antibiotic included in the cell growth media; not more than 20 ng) and yeast protein (no more than 5%).

In a particular embodiment, the pharmaceutical composition comprises Teriparatide [rDNA origin] injection (FORTEO®) which contains recombinant human parathyroid hormone (1-34), and is also called 222 rhPTH (1-34).

Teriparatide [rDNA origin] injection is indicated for treatment of postmenopausal women with osteoporosis at high risk for fracture; increase of bone mass in men with primary or hypogonadal osteoporosis at high risk for fracture; and treatment of men and women with osteoporosis associated with sustained systemic glucocorticoid therapy at high risk for fracture.

Each prefilled delivery device is filled with either 3.3 mL (to deliver 3 mL) or 2.7 mL (to deliver 2.4 mL). Each mL contains 250 mcg teriparatide (corrected for acetate, chloride, and water content), 0.41 mg glacial acetic acid, 0.1 mg sodium acetate (anhydrous), 45.4 mg mannitol, 3 mg Metacresol, and Water for injection. In addition, hydrochloric acid 231 solution 10% and/or sodium hydroxide solution 10% may have been added to adjust the product to pH 4. FORTEO® is available for subcutaneous administration.

In a particular embodiment, the pharmaceutical composition comprises Glatiramer acetate, Copolymer 1, or Cop-1 (COPAXONE®), which is indicated for reduction of the frequency of relapses in patients with Relapsing-Remitting Multiple Sclerosis (RRMS), including patients who have experienced a first clinical episode and have MRI features consistent with multiple sclerosis. Glatiramer acetate is designated L-glutamic acid polymer with L-alanine, L-lysine and L-tyrosine, acetate (salt) and has the structural formula: (Glu, Ala, Lys, Tyr)x.xCH$_3$COOH (C$_5$H$_9$NO$_4$.C$_3$H$_7$NO$_2$.C$_6$H$_{14}$N$_2$O$_2$.C$_9$H$_{11}$NO$_3$)x.xC$_2$H$_4$O$_2$ Glatiramer acetate Single-use prefilled syringe containing 1 mL solution with 20 mg of glatiramer acetate and 40 mg of mannitol. The pH range of the solution is approximately 5.5 to 7.0. COPAXONE® is available for subcutaneous administration.

In particular embodiments, the pharmaceutical composition may be selected from the group of pharmaceutical products or active pharmaceutical ingredients (API) set forth in Table 6.

TABLE 6

Pharmaceutical Products in Development

| PRODUCT | GENERIC NAME | THERAPEUTIC SUBCATEGORY |
| --- | --- | --- |
| Tresiba | insulin degludec | Anti-diabetics |
| CP-4126 | gemcitabine elaidate | Anti-metabolites |
| Alpharadin | radium Ra-223 chloride | Radiopharmaceuticals |
| Trastuzumab-DM1 | trastuzumab emtansine | Anti-neoplastic MAbs |
| Abilify Depot | aripiprazole | Anti-psychotics |
| Ryzodeg | insulin aspart; insulin degludec | Anti-diabetics |
| Bexsero | meningococcal B vaccine | Vaccines |
| Reolysin | — | Other cytostatics |
| IMMU-107 | yttrium Y-90 clivatuzumab tetraxetan | Anti-neoplastic MAbs |
| AEZS-108 | — | Other cytostatics |
| Dulaglutide | dulaglutide | Anti-diabetics |
| Lyxumia | lixisenatide | Anti-diabetics |
| Bavituximab | bavituximab | Anti-neoplastic MAbs |
| Heplisav | hepatitis B vaccine | Vaccines |
| RG3638 | onartuzumab | Anti-neoplastic MAbs |
| V503 | human papillomavirus (HPV) vaccine | Vaccines |
| GRN163L | imetelstat sodium | Other cytostatics |
| Seasonal Flu VLP Vaccine | influenza vaccine | Vaccines |
| HyperAcute Pancreas | algenpantucel-L | Other cytostatics |
| GALNS | elosulfase alfa | Other therapeutic products |
| SBC-102 | sebelipase alfa | Other therapeutic products |
| Allovectin-7 | velimogene aliplasmid | Other cytostatics |
| New insulin glargine product | insulin glargine recombinant | Anti-diabetics |
| RG7159/GA101 | obinutuzumab | Anti-neoplastic MAbs |
| TR-701 IV | tedizolid phosphate | Anti-bacterials |
| Blisibimod | blisibimod | Immunosuppressants |
| Baxter/Asklepios Haemophilia Gene Therapy | — | Anti-fibrinolytics |
| Ganetespib | ganetespib | Other cytostatics |
| Lemtrada | alemtuzumab | MS Therapies |
| CUDC-101 | — | Other cytostatics |

TABLE 6-continued

Pharmaceutical Products in Development

| PRODUCT | GENERIC NAME | THERAPEUTIC SUBCATEGORY |
|---|---|---|
| ThermoDox | doxorubicin hydrochloride | Cytotoxic antibiotics |
| Ganetespib | ganetespib | Other cytostatics |
| Ramucirumab | ramucirumab | Anti-neoplastic MAbs |
| Jetrea | ocriplasmin | Eye preparations |
| Zinforo | ceftaroline fosamil | Anti-bacterials |
| E5564 | eritoran tetrasodium | Immunosuppressants |
| Vascular Repair Cells | — | Cerebral & peripheral vasotherapeutics |
| ENB-0040 | asfotase alfa | Other musculoskeletal agents |
| Vosaroxin | vosaroxin | Other cytostatics |
| PEGylated-IFN β-1a | peginterferon beta-1a | MS Therapies |
| IPI-504 | retaspimycin hydrochloride | Other cytostatics |
| Solanezumab | solanezumab | Nootropics |
| RG1594 | ocrelizumab | MS Therapies |
| Brilacidin (IV) | brilacidin | Anti-bacterials |
| Heplisav | hepatitis B vaccine | Vaccines |
| HuCNS-SC | neural stem cells (human) | Other CNS drugs |
| Albiglutide | albiglutide | Anti-diabetics |
| AIN457 | secukinumab | Other dermatologicals |
| Defibrotide | defibrotide | Cerebral & peripheral vasotherapeutics |
| Daclizumab | daclizumab | MS Therapies |
| Relaxin | serelaxin | Angiotensin II antagonists |
| Protectan CBLB502 | — | Other therapeutic products |
| Gattex | teduglutide | Anti-spasmodics & anti-cholinergics |
| Brilacidin (IV) | brilacidin | Anti-bacterials |
| PEG-IFN-lambda | peginterferon lambda-1a | Interferons |
| MAGE-A3 | astuprotimut-R | Other cytostatics |
| Soluble Ferric Pyrophosphate | ferric pyrophosphate | Anti-anaemics |
| Turoctocog alfa | turoctocog alfa | Anti-fibrinolytics |
| Ixekizumab | ixekizumab | Anti-psoriasis agents |
| Epratuzumab | epratuzumab | Immunosuppressants |
| REGN727/SAR236553 | alirocumab | Anti-hyperlipidaemics |
| CD-NP | cenderitide | Cardiac therapy |
| Siltuximab | siltuximab | Anti-neoplastic MAbs |
| SAR2405550/BSI-201 | iniparib | Other cytostatics |
| Zymafos | palifosfamide | Alkylating agents |
| RG3637/TNX-650 | lebrikizumab | Other bronchodilators |
| BAX 111 | vonicog alfa | Anti-fibrinolytics |
| AMG 785 (CDP7851) | romosozumab | Bone calcium regulators |
| BMS-901608 | elotuzumab | Anti-neoplastic MAbs |
| Otamixaban | otamixaban | Anti-coagulants |
| Vedolizumab | vedolizumab | Gastro-intestinal anti-inflammatories |
| Tabalumab | tabalumab | Other anti-rheumatics |
| BiovaxID | — | Other cytostatics |
| Sarilumab | sarilumab | Other anti-rheumatics |
| Analog Insulin-PH20 | hyaluronidase (human); insulin | Anti-diabetics |
| Lantus + Lixisenatide | insulin glargine; lixisenatide | Anti-diabetics |
| CXA-201 | ceftolozane sulfate; tazobactam sodium | Anti-bacterials |
| Allovectin-7 | velimogene aliplasmid | Other cytostatics |
| AVI-4658 | eteplirsen | Other musculoskeletal agents |
| hGH-CTP (MOD-4023) | growth hormone (human) | Growth hormones |
| ICT-107 | — | Other cytostatics |
| IDegLira | insulin degludec; liraglutide | Anti-diabetics |
| ONO-4538/BMS-936558 | nivolumab | Anti-neoplastic MAbs |
| rFVIIIFc | factor VIII | Anti-fibrinolytics |
| TH-302 | — | Alkylating agents |
| GSK2402968 | drisapersen | Other musculoskeletal agents |
| Trasruzumab-DM1 | trastuzumab emtansine | Anti-neoplastic MAbs |
| Natpara | parathyroid hormone 1-84 [rdna origin] | Other hormone preparations |
| HyperAcute Pancreas | — | Other cytostatics |
| AMG 403 | fulranumab | Non-narcotic analgesics |
| HGT 1110 | — | Other therapeutic products |
| RigScan CR | minretumomab | Diagnostic imaging |
| Necitumumab | necitumumab | Anti-neoplastic MAbs |
| Visamerin/Mulsevo | semuloparin sodium | Anti-coagulants |
| HGT-1410 | — | Other therapeutic products |
| RG1273 | pertuzumab | Anti-neoplastic MAbs |
| Adcetris | brentuximab vedotin | Anti-neoplastic MAbs |
| HZ/su | herpes zoster vaccine | Vaccines |
| IMC-A12 | cixutumumab | Anti-neoplastic MAbs |

In a particular embodiment, the pharmaceutical composition comprises insulin degludec (TRESIBA®) (NN1250), which is an ultra-long-acting basal insulin. Insulin degludec is indicated for the treatment of type 1 and 2 diabetes. The duration of action for insulin degludec is more than 24 hours is intended to offer a flexible once-daily treatment and an improved safety profile. Insulin degludec is approved in Japan and has been submitted for marketing authorization in the US, Europe and other major markets.

In a particular embodiment, the pharmaceutical composition comprises gemcitabine elaidate (also known as CO-101; CP-4126), which is a lipophilic, unsaturated fatty acid ester derivative of gemcitabine (dFdC), an antimetabolite deoxynucleoside analogue, with potential antineoplastic activity. This formulation of gemcitabine may be less susceptible to deamination and deactivation by deoxycytidine deaminase. Gemcitabine elaidate (shown below) is indicated for the treatment of various cancers.

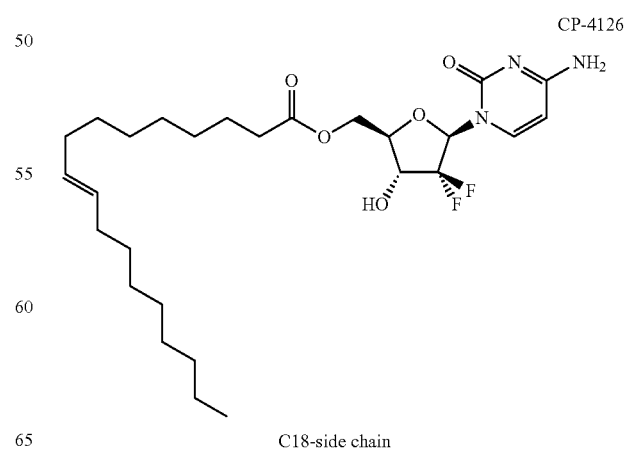

CP-4126

C18-side chain

Gemcitabine elaidate was designed to improve upon the efficacy of gemcitabine by enabling the drug to enter cancer cells without requiring uptake by a specific transporter molecule. Intravenous gemcitabine elaidate is currently being evaluated in a clinical trial in advanced pancreatic cancer. Gemcitabine elaidate is the current standard treatment for advanced pancreatic cancer, and is also used in combination with other chemotherapy agents for the treatment of other cancers, including ovarian, non-small cell lung, and breast cancer.

In a particular embodiment, the pharmaceutical composition comprises Radium-223 dichloride (ALPHARADIN). Radium-223, formulated in a sterile solution, has certain properties that make it ideal for development as an alpha-pharmaceutical: its half-life is 11.4 days, which is long enough to allow a convenient dosing regimen at four-weekly intervals, and also long enough for industrial production and global distribution. The nature of the alpha-particle emission from radium-223 also means that the shielding requirements for distribution and medical use are minimal, making it simple and easy to use as an intravenous injection in a hospital outpatient setting.

Radium-223 dichloride is indicated for use as a cancer therapy. Radium-223 dichloride selectively targets new bone growth, and thereby the bone metastases and their tumor cells. It kills the tumor cells by highly localized short-range alpha irradiation, while minimizing damage to surrounding healthy cells.

Radium-223 dichloride has been used in clinical trials, where treatment is on an outpatient basis, administered by IV injection once a month for 4 or 6 months.

In a particular embodiment, the pharmaceutical composition comprises Trastuzumab emtansine (TRASTU-ZUMAB-DM1), an antibody-drug conjugate (ADC) being studied in HER2-positive cancers. It is comprised of the antibody trastuzumab and the chemotherapy DM1 attached together using a stable linker. Trastuzumab emtansine is designed to target and inhibit HER2 signalling and deliver the chemotherapy DM1 directly inside HER2-positive cancer cells. Trastuzumab emtansine is administered by intravenous infusion.

In a particular embodiment, the pharmaceutical composition comprises Aripiprazole IM depot formulation (ABILIFY® Depot), a sterile lyophilized cake that, when reconstituted with sterile water for injection, forms an injectable suspension.

While the use of aripiprazole IM depot formulation is investigational, aripiprazole is currently approved and marketed as ABILIFY® (aripiprazole). Aripiprazole is a psychotropic drug that is available as ABILIFY® (aripiprazole) Tablets, ABILIFY DISCMELT® (aripiprazole) Orally Disintegrating Tablets, ABILIFY® (aripiprazole) Oral Solution, and ABILIFY® (aripiprazole) Injection, a solution for intramuscular injection. ABILIFY® Injection is available in single-dose vials as a ready-to-use, 9.75 mg/1.3 mL (7.5 mg/mL) clear, colorless, sterile, aqueous solution for intramuscular use only. Inactive ingredients for this solution include 150 mg/mL of sulfobutylether β-cyclodextrin (SBECD), tartaric acid, sodium hydroxide, and water for injection.

Aripiprazole IM depot has been studied in a Phase 3 clinical trial evaluating the efficacy, safety and tolerability of once-monthly aripiprazole intramuscular (IM) depot formulation for the maintenance treatment of adults with schizophrenia.

In a particular embodiment, the pharmaceutical composition comprises insulin aspart; insulin degludec (RYZO-DEG®), a soluble fixed combination of ultra long-acting basal insulin in combination with a boost of bolus insulin aspart. Insulin aspart is intended to offer basal insulin coverage with a distinct meal peak of insulin. Insulin aspart is indicated for the treatment of type 1 and 2 diabetes.

In a particular embodiment, the pharmaceutical composition comprises meningococcal serogroup B vaccine (BEXSERO®), a multicomponent meningococcal serogroup B vaccine (4CMenB). BEXSERO® is indicated for use as a vaccine to provide broad coverage against meningococcal B disease.

In a phase 2b, open-label, parallel-group, randomized controlled trial, the 4CMenB vaccine consisted of 50 μg each of fHbp1, NadA, and NHBA fusion proteins, 25 μg of detoxified OMV from *N meningitidis* strain NZ98/254, 1.5 of mg aluminum hydroxide, and histidine 10 mM in 0.5 mL of water for injection. Participants also received a combined diphtheria, tetanus, acellular pertussis, inactivated polio, hepatitis B, and *Haemophilus influenzae* type b vaccine (DTaP-HBV-IPV/Hib) (Infanrix Hexa; GlaxoSmithKline) and 7-valent pneumococcal glycoconjugate vaccine (PCV7) (PREVNAR 13®; Wyeth Pharmaceuticals). The study design allowed assessment of 3 primary 4CMenB schedules: ages 2, 4, and 6 months, together with routine infant vaccines (concomitant); 2, 4, and 6 months, with routine vaccines given separately at 3, 5, and 7 months (intercalated); and 2, 3, and 4 months, concomitantly with routine infant vaccines (accelerated). A control group received DTaP-HBV-IPV/Hib and PCV7 only at 2, 3, and 4 months. All vaccines were administered by intramuscular injection in the anterolateral thigh.

In a particular embodiment, the pharmaceutical composition comprises Respiratory Enteric Orphan Virus (REOLYSIN®), a proprietary variant of the reovirus, which is widely found in the environment. Pre clinical testing has identified cancer cell lines as being susceptible to reovirus infection. Respiratory Enteric Orphan Virus is an intravenous formulation of reovirus serotype 3-Dearing strain which is a double stranded RNA non-enveloped icosahedral virus capable of inducing cytopathic effects in cancer cells that have an activating mutation in the ras protooncogene.

In a particular embodiment, the pharmaceutical composition comprises Yttrium Y-90 clivatuzumab tetraxetan (IMMU-107), a Yttrium-90 radiolabeled humanized mAb against MUC1. It is a humanized monoclonal antibody highly specific for pancreatic cancer.

In a phase I clinical trial, prior to therapy, all patients received a diagnostic dose of hPAM4 labeled with the radioisotope, indium-111, to ensure an acceptable distribution within the body and radiation dose to the pancreas for intended therapy. Patients then received a single infusion of 90Y-hPAM4 with the Y-90 dose escalating in increments of 5 mCi/m2.

In a particular embodiment, the pharmaceutical composition comprises Zoptarelin doxorubicin (AEZS-108), a targeted cytotoxic peptide conjugate which is a hybrid molecule composed of a synthetic peptide carrier and a well-known cytotoxic agent, doxorubicin. Zoptarelin doxorubicin appears to be a suitable drug for targeted chemotherapy of cancers expressing receptors for LHRH. Zoptarelin doxorubicin is formulated as a powder for solution for infusion.

The chemical name of Zoptarelin doxorubicin is (3S,6S,9S,12R,15R)-2-((2S,4S)-4-(((2R,4S,5S,6S)-4-amino-5-hydroxy-6-methyltetrahydro-2H-pyran-2-yl)oxy)-2,5,12-trihydroxy-7-methoxy-6,11-dioxo-1,2,3,4,6,11-hexahydrotetracen-2-yl)-2-oxoethyl 3-((1H-imidazol-2-yl)methyl)-6-(((1H-indol-3-yl)methyl)-15-(((S)-1-(((S)-1-((S)-

2-((2-amino-2-oxoethyl)carbamoyl)pyrrolidin-1-yl)-5-guanidino-1-oxopentan-2-yl)amino)-4-methyl-1-oxopentan-2-yl)carbamoyl)-12-(4-hydroxybenzyl)-9-(hydroxymethyl)-1,4,7,10,13,21-hexaoxo-1-((R)-5-oxopyrrolidin-2-yl)-2,5,8,11,14,20-hexaazapentacosan-25-oate. The formula of zoptarelin doxorubicin is $C_{91}H_{117}N_{19}O_{26}$.

In a phase 2 study, patients received a recommended dose of 267 mg/m2 by intravenous infusion over 2 hours, with retreatment every 3 weeks, for up to 6 courses. Response rate per Response Evaluation Criteria in Solid Tumors (RECIST) was defined as primary endpoint. Secondary endpoints were safety, time-to-progression (TTP) and overall survival (OS). Zoptarelin doxorubicin at a dosage of 267 mg/m2 every 3 weeks was active and well tolerated in patients with endometrial cancer.

In a particular embodiment, the pharmaceutical composition comprises dulaglutide, a fusion of GLP-1 to a larger carrier moiety. This carrier moiety is a modified IgG4 Fc fragment, which is connected by a small peptide linker. Dulaglutide is indicated for treatment of type II diabetes. Its molecular formula is $C_{2646}H_{4044}N_{704}O_{836}S_{18}$.

In a particular embodiment, the pharmaceutical composition comprises lixisenatide (LYXUMIA®), a once-daily GLP-1 receptor agonist. Lixisenatide is indicated for the treatment of diabetes. In a clinical trial (Get Goal) lixisenatide once-daily, with a one-step dose increase regimen and a single maintenance dose, has also been shown to be well-tolerated and to lead to significantly improved glycemic control with low risk of hypoglycemia.

In a particular embodiment, the pharmaceutical composition comprises BAVITUXIMAB, a phosphatidylserine (PS)-targeting monoclonal antibody. Phosphatidylserine exposure is increased on endothelial cells and apoptotic cancer cells in solid tumors, allowing tumor-specific targeting of bavituximab.

In a Phase 1 safety and pharmacokinetic study, patients with refractory advanced solid tumors were enrolled into four sequential dose-escalation cohorts (0.1, 0.3, 1, or 3 mg/kg bavituximab weekly) with two dosing schedules. Patients in the 0.1 and 0.3 mg/kg cohorts received bavituximab on days 0, 28, 35, and 42. Patients in the 1 and 3 mg/kg cohorts were administered bavituximab on days 0, 7, 14, and 21. Safety, pharmacokinetics, and tumor response were assessed. Bavituximab, which was supplied as a sterile solution in 5 mL single-use borosilicate type I glass vials containing 20 3 mg/mL bavituximab, acetate, and water for injection, was administered intravenously over approximately 90 minutes. Premedication was not administered.

In a particular embodiment, the pharmaceutical composition comprises Hepatitis B vaccine (HEPLISAV™), an investigational adult hepatitis B vaccine comprised of Dynavox's first generation 1018 immunostimulatory sequence (1018 ISS) and hepatitis B surface antigen (HBsAg). ISS are short, CpG-containing oligonucleotides.

The anticipated product profile is 20 μg HBsAg mixed with 3000 μg 1018 ISS, given as 2 doses on 0,1 month schedule indicated for Adults. Dosing is anticipated to be 3 doses on 0,1,6 month schedule for chronic kidney disease (CKD)/dialysis patients. Hepatitis B vaccine is administered as an intramuscular injection.

In a particular embodiment, the pharmaceutical composition comprises onartuzumab, MetMAb (RG3638), a first-in-class monoclonal monovalent (one-armed) antibody designed to inhibit Met signalling in cancer cells by binding to the extracellular domain of Met, thereby blocking HGF-mediated activation. HGF/Met signalling is activated through over expression of either HGF and/or Met in tumours as well as through activating mutations in Met. Activation of Met signalling drives tumour growth and has also been linked to tumour angiogenesis and metastatic potential. Onartuzumab is indicated in the treatment of cancers, including 1st line squamous non-small cell lung cancer, non-squamous non small cell lung cancer, metastatic breast cancer and metastatic colorectal cancer.

In a particular embodiment, the pharmaceutical composition comprises Human Papillomavirus Vaccine (V503), a multivalent (nine valent) Human Papillomavirus [HPV] L1 Virus-Like Particle [VLP] Vaccine. Human Papillomavirus Vaccine is indicated for the treatment of Cervical Cancer, Vulvar Cancer, Vaginal Cancer, Genital Warts, Human Papillomavirus Infection. Human Papillomavirus Vaccine is given by intramuscular injection. A phase III clinical trial is underway.

In a particular embodiment, the pharmaceutical composition comprises Imetelstat (GRN163L), a potent and specific telomerase inhibitor. Imetelstat is a novel lipid-based conjugate of the first-generation oligonucleotide Imetelstat, and consists of a 13-mer oligonucleotide N3'-P5' thio-phosphoramidate (NPS oligonucleotide) that is covalently attached to a C16 (palmitoyl) lipid moiety. Imelstat is indicated for the treatment of various cancers.

Based on in vitro and in vivo efficacy in a series of animal studies, imetelstat has entered six phase I and I/II clinical trials for various cancers including hematologic and solid tumors. For all the phase I and I/II trials, the primary outcomes are safety, tolerability, and determination of the maximum tolerated dose (MTD). Dosing is based on 3- or 4-week cycles of once-weekly 2- or 6-h intravenous infusions.

In a particular embodiment, the pharmaceutical composition comprises Seasonal Flu VLP Vaccine, a trivalent seasonal influenza virus-like-particle (VLP)-based vaccine. Virus-like particles (VLPs) mimic the external structure of viruses but lack the live genetic material that causes viral replication and infection. VLPs can be designed quickly to match individual viral strains and be produced efficiently using portable cell-culture technology. Novavax's VLP-based vaccine candidates are produced more rapidly than egg-based vaccines by using proprietary, portable, recombinant cell-culture technology.

A phase II study has been carried out. The study's primary objectives of demonstrating safety and immunogenicity of three ascending dose levels of the quadrivalent influenza vaccine were achieved. The VLP vaccine candidate demonstrated immunogenicity against all four viral strains based on hemagglutination inhibition assay (HAI) responses at day 21, was also well-tolerated with no vaccine-related serious adverse events observed and reactogenicity was considered acceptable. The Phase II trial, conducted in Australia, enrolled 500 eligible subjects who were randomized into five treatment groups of approximately 100 subjects stratified by age and receipt of influenza immunization in the 2011 season. At day zero, study participants received a single intramuscular vaccine injection of the quadrivalent vaccine containing one of three ascending doses or one of two trivalent comparators: Novavax VLP vaccine or a standard dose of a licensed trivalent activated vaccine.

In a particular embodiment, the pharmaceutical composition comprises Algenpantucel-L (HyperAcute Pancreas), an immunotherapy indicated for the treatment of pancreatic cancer. Algenpantucel-L consists of equal doses of two separate allogeneic pancreatic cancer cell lines engineered to express a-Gal. Algenpantucel-L is currently being evaluated in a multi-institution, randomized, Phase 3 clinical trial under a Special Protocol Assessment with the FDA.

In a particular embodiment, the pharmaceutical composition comprises Elosulfase alfa (GALNS), a proposed treatment for Morqio A syndrome. Morquio A syndrome is an inherited, autosomal recessive disease caused by a deficiency of a particular lysosomal enzyme, N-acetylgalactosamine-6 sulfatase. BioMarin's experimental drug for Morquio A syndrome is an enzyme replacement of elosulfase alfa (called BMN 110), which is designed to clear keratan sulfate from the lysosome. BMN 110 is being studied to determine if it is safe, if it will slow the progression of the disease and if it will improve some of the symptoms.

BioMarin started BMN 110 clinical studies in humans in 2009 to evaluate safety and efficacy. In a phase III Multi-center, Multinational, Extension Studythe Long-Term Efficacy and Safety of BMN 110 in Patients With Mucopolysaccharidosis IVA (Morquio A Syndrome) MOR-005 was evaluated. Participants will receive 2 mg/kg weekly or every other weekly dosing of study drug via infusion until the MOR-004 study is unblinded and the optimal dose is selected. All subjects will then be treated with the optimal dose for up to approximately 5 years or until the drug is approved.

In a particular embodiment, the pharmaceutical composition comprises Sebelipase alfa (SBC-102), an enzyme replacement therapy for Lysosomal Acid Lipase (LAL) Deficiency, a lysosomal storage disorder (LSD). The product is a recombinant form of the human LAL enzyme. Sebelipase alfa contains glycan structures that are specifically recognized and internalized by specific receptors into key target cells.

Synageva BioPharma Corp. has released a preliminary analysis of data from an ongoing Phase 1/2 extension study of sebelipase alfa in adults with late-onset LAL Deficiency. After completing four weeks of treatment in the initial Phase 1/2 trial, patients were allowed to continue treatment with sebelipase alfa as part of a long-term, open-label, extension study. In the extension study, patients received four once-weekly infusions of sebelipase alfa (0.35 mg/kg, 1 mg/kg, or 3 mg/kg) and then transitioned to every other week infusions of sebelipase alfa (1 mg/kg or 3 mg/kg). Data demonstrate sustained impact of SBC-102 on reducing liver transaminase levels. In addition, total cholesterol, HDL cholesterol, and triglycerides significantly improved ($p<0.05$) from patients' original baseline, and a reduction in LDL was also observed during the same time period.

In a particular embodiment, the pharmaceutical composition comprises Velimogene aliplasmid. Velimogene aliplasmid (ALLOVECTIN-7®) therapy is a form of active immunotherapy that aims at immunization of the host with substances designed to elicit an immune reaction that will eliminate or slow down the growth and spread of cancer. It is indicated for the treatment of metastatic melanoma, and has potential applications in solid tumors (head & neck; breast; lung; prostate). Velimogene aliplasmid comprises a bicistronic plasmid: HLA-B7 and β2 microglobulin. It is formulated with DMRIE:DOPE in a single vial formulation, to be given as an intralesional injection.

In a particular embodiment, the pharmaceutical composition comprises insulin glargine injection (rDNA origin) (LANTUS®), a recombinant human insulin analogue that is a long-acting, parenteral blood-glucose-lowering agent. Insulin glargine is produced by recombinant DNA technology utilizing a non-pathogenic laboratory strain of *Escherichia coli* (K12) as the production organism. Insulin glargine differs from natural human insulin in that the amino acid asparagine at position 21 of the A-chain is replaced by glycine and two arginines are added to the C-terminus of the B-chain.

Insulin glargine is administered subcutaneously once a day. It may be administered at any time during the day as long as it is administered at the same time every day. The desired blood glucose levels as well as the doses and timing of antidiabetic medications must be determined and adjusted individually. LANTUS® is a clear solution, not a suspension. Insulin glargine must not be mixed with any other insulin. Mixing can change the time/action profile of insulin glargine and cause precipitation In a particular embodiment, the pharmaceutical composition comprises obinutuzumab (GA101/RG7159), a glyco-engineered humanized anti-CD20 monoclonal antibody for chronic lymphocytic leukemia and non-Hodgkin's lymphoma. Obinutuzumab is given as an injection.

In a particular embodiment, the pharmaceutical composition comprises Tedizolid phosphate (TR-701), a second-generation oxazolidinone antibiotic being developed for the treatment of serious Gram-positive infections, including those caused by Methicillin-resistant *Staphylococcus aureus* (MRSA). Tedizolid phosphate is a prodrug antibiotic that is cleaved in the blood stream to the active compound, Tedizolid (TR-700). Tedizolid phosphate is being developed for both intravenous and oral administration.

In a particular embodiment, the pharmaceutical composition comprises Blisibimod, a selective peptibody antagonist of the B cell activating factor (BAFF) cytokine that is initially being developed as a treatment for lupus. Blisibimod is a fusion polypeptide protein (or peptibody) consisting of a novel BAFF binding domain fused to the N-terminus of the Fc region of human antibody. Blisibimod binds to BAFF and inhibits the interaction of BAFF with its receptors. BAFF is a tumor necrosis family member and is critical to the development, maintenance and survival of B-cells. BAFF has been associated with a wide range of B-cell mediated autoimmune diseases, including SLE, lupus, lupus nephritis, rheumatoid arthritis, multiple sclerosis, Sjögren's Syndrome, Graves' Disease and others. Blisibimod is administered intravenously and subcutaneously.

In a particular embodiment, the pharmaceutical composition comprises recombinant adeno-associated virus (rAAV) Biological Nano Particles (BNPs) associated with Baxter/Asklepios Hemophilia Gene Therapy. Baxter/Asklepios Hemophilia Gene Therapy involves the use of proprietary BNPs, which are based on recombinant adeno-associated virus (rAAV) synthetically designed from components of different associated adeno viruses as well as other parvoviruses, for the treatment of hemophilia B. Biostrophin, containing miniaturized, functional replacement genes for the muscle protein dystrophin, has been combined with BNPs, to target genes directly to muscle cells. As a result, this therapy may also have applications in gene therapy and tissue engineering for congestive heart failure, bone allografting, treatment of Hemophilia, neurodegenerative disorders, and epilepsy.

In a particular embodiment, the pharmaceutical composition comprises Ganetespib (shown below), a synthetic small molecule designed to inhibit Hsp90, which is a chaperone protein required for the proper folding and activation of certain proteins that promote the growth, proliferation, and survival of many different types of cancer. Ganetespib-inhibition of Hsp90 causes the degradation of numerous growth factors that rely on Hsp90 for proper folding/activation and the subsequent death of cancer cells dependent on these growth factors. Ganetespib administration can be administered intravenously.

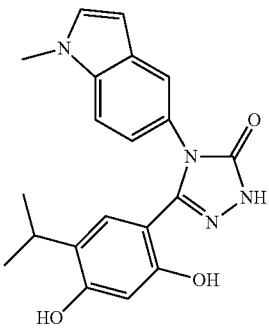 [SMILES: CC(C)c1cc(-c2n[nH]c(=O)n2-c2ccc3c(ccn3C)c2)c(O)cc1O]

In a particular embodiment, the pharmaceutical composition comprises Alemtuzumab (Lemtrada), a monoclonal antibody designed for the treatment of relapsing multiple sclerosis. The antibody selectively targets CD52, which is an abundant protein on T- and B-cells. Treatment with alemtuzumab is designed to decrease levels of circulating T- and B-cells thought to be responsible for the damaging inflammatory process in individuals with multiple sclerosis, while having minimal impact on other immune cells. The acute anti-inflammatory effect of alemtuzumab is immediately followed by the onset of a distinctive pattern of T- and B-cell repopulation that continues over time, rebalancing the immune system in a way that potentially reduces multiple sclerosis disease activity. Alemtuzumab can be administered either intravenously or orally.

In a particular embodiment, the pharmaceutical composition comprises CUDC-101 (shown below), a multi-targeted inhibitor designed to inhibit epidermal growth factor receptor (EGFR), epidermal growth factor 2 (Her2) and histone deacetylase (HDAC) to promote tumor regression or tumor growth inhibition that targets cancer cells at multiple points of intervention. CUDC-101 can be administered intravenously (oral delivery formulation also being developed).

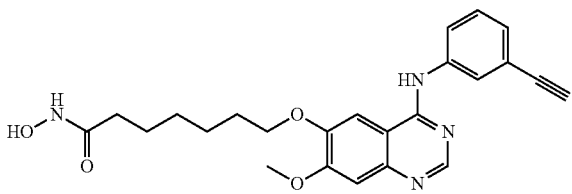 [SMILES: C#Cc1cccc(Nc2ncnc3cc(OC)c(OCCCCCCC(=O)NO)cc23)c1]

In a particular embodiment, the pharmaceutical composition comprises Doxorubicin hydrochloride (ThermoDox), a proprietary heat-activated liposomal encapsulation containing the oncology drug doxorubicin, which is an approved and frequently used drug for the treatment of a wide range of cancers. Doxorubicin hydrochloride is administered intravenously in combination with Radio Frequency Ablation (RFA). The localized mild hyperthermic conditions (39.5-42° C.) brought about by the RFA applied directly to the cancerous lesion, promotes the release of the entrapped doxorubicin from the liposome. This delivery technology enables high concentrations of doxorubicin to be preferentially delivered to a targeted tumor. The coupling of the administration of doxorubicin with RFA treatment may help decrease the serious side effects associated with doxorubicin.

In a particular embodiment, the pharmaceutical composition comprises Ramucirumab, a recombinant, fully human monoclonal antibody directed against human vascular endothelial growth factor receptor 2 (VEGFR-2) and designed for the treatment of solid tumors. By binding to VEGFR-2, which is the critical receptor involved in promoting malignant angiogenesis resulting in tumor growth and metastases, ramucirumab functions as a receptor antagonist, blocking the binding of vascular growth factor (VEGF), thus inhibiting the downstream angiogenic effects. Ramucirumab is administered intravenously.

In a particular embodiment, the pharmaceutical composition comprises Ocriplasmin (JETREA®), a recombinant form of human plasmin that dissolves the protein links that form between the vitreous and the macula, separating them enzymatically. The drug, designed to treat Vitreomacular adhesion (VMA), is administered via a single injection into the eyeball and is capable resolving the condition without the need for surgery. VMA is a progressive, age-related debilitating eye disease that can lead to visual distortion, loss in visual acuity, and central blindness. In individuals with VMA, the vitreous adheres too strongly to the retina at the rear of the eye, causing a 'pulling' effect that distorts vision. In time, this pulling can lead to the formation of holes in the macula, leading to vision loss or other complications in the effected area. Currently, the only treatment for advanced VMA is the surgical removal of the vitreous.

In a particular embodiment, the pharmaceutical composition comprises Ceftaroline fosamil (ZINFORO™), an intravenous antibiotic formulation designed for the treatment of adult patients with complicated skin and soft tissue infections (cSSTI) or Community acquired pneumonia (CAP). Ceftaroline fosamil is a type of antibiotic known as cephalosporin that belongs to the broad class of antibiotics known as 'beta-lactams'. The antibiotic functions by interfering with the production of peptidoglycans, which are essential components of bacterial cell walls. The administration of ceftaroline fosamil results in bactericidal activity with broad coverage against common causative pathogens, such as *Staphylococcus aureus*, including MRSA, and Streptococci in cSSTI and *Streptococcus pneumonia* and methicillin-susceptible *Staphylococcus aureus* (MSSA) in CAP.

Chemically, the prodrug, ceftaroline fosamil monoacetate monohydrate (shown below), has a molecular weight of 762.75. The empirical formula is $C_{22}H_{21}N_8O_8PS_4$—$C_2H_4O_2$—$H_2O$.

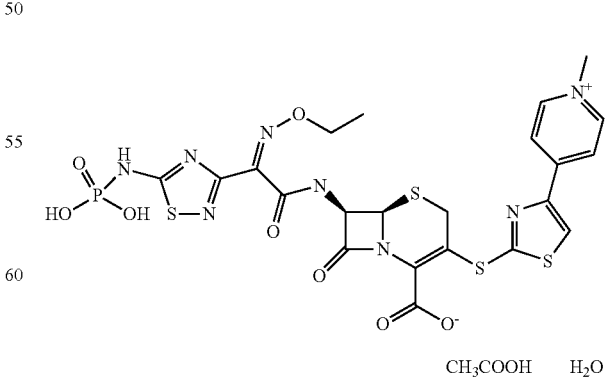

Each vial contains ceftaroline fosamil and L-arginine, which results in a constituted solution between pH 4.8 to 6.5.

In a particular embodiment, the pharmaceutical composition comprises Eritoran tetrasodium (E5564). Toll-like receptors are a class of proteins that recognize the presence of various microorganisms and subsequently initiate an immune response. Toll-like receptor 4 (TLR4), which is a member of this class of proteins, recognizes lipopolysaccharide (LPS), a component of the outer membrane of Gram-negative bacteria. The recognition of LPS by TLR4 is thought to be an important trigger of the inflammatory response in sepsis. Eritoran tetrasodium (E5564), a synthetic Toll-like receptor 4 antagonist, is a structural analog of the lipid A portion of LPS, and is designed to block activation of TLR4, preventing the initiation of the inflammatory response characterized by sepsis and septic shock.

In a particular embodiment, the pharmaceutical composition comprises Ixmyelocel-T (formally Vascular Repair Cells, i.e., VRC5), which is designed as a treatment for peripheral arterial diseases, e.g., critical limb ischemia. Ixmyelocel-T is a patient-specific, expanded multicellular therapy, which selectively expands mesenchymal cells, monocytes and alternatively activated macrophages, up to several hundred times more than the number found in the patient's bone marrow, while retaining many of the hematopoietic cells collected from only a small sample (50 ml) of the patient's bone marrow. Vascular Repair Cells is administered by intramuscular injection.

In a particular embodiment, the pharmaceutical composition comprises Asfotase alfa (ENB-0040), a human recombinant protein for the treatment of patients with hypophosphatasia (HPP). Asfotase alfa is designed to counter the genetically defective metabolic process and prevent or reverse the severe and life-threatening consequences of dysregulated calcium and phosphate metabolism in patients with HPP. Asfotase alfa is administered by intravenous infusion and/or subcutaneous injections.

Asfotase alfa is formulated at 0.15, 0.6 and 2.5 mg/mL in 25 mmol/L sodium phosphate, 150 mmol/L sodium chloride, pH 7.4.

In a particular embodiment, the pharmaceutical composition comprises Vosaroxin (shown below), a small molecule developed for the treatment of acute myeloid leukaemia (AML). It is also being evaluated in clinical trials for platinum-resistance ovarian cancer.

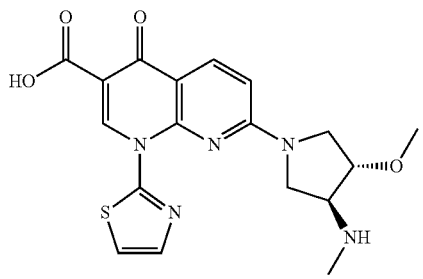 [SMILES: CN[C@H]1CN(c2ccc3c(=O)c(C(=O)O)cn(-c4nccs4)c3n2)C[C@@H]1OC]

(+)-7-[(3S,4S)-3-methoxy-4-(methylamino)pyrrolidin-1-yl]-4-oxo-1-(thiazol-2-yl)-1,4-dihydro-1,8-naphthyridine-3-carboxylic acid Vosaroxin is a replication-dependent DNA-damaging agent that induces G2 arrest and apoptosis (cell death). Vosaroxin has demonstrated tumor responses in a variety of tumor types and has been generally well tolerated.

In a particular embodiment, the pharmaceutical composition comprises PEGylated Interferon β-1a, a chemically modified version of interferon beta-1a. More specifically, it is PEGylated form of interferon beta-1a. PEGylated Interferon β-1a is being developed as a novel therapeutic agent for the treatment of relapsing multiple sclerosis. PEGylated-IFN β-1a is administered by subcutaneous injections.

In a particular embodiment, the pharmaceutical composition comprises Retaspimycin hydrochloride (see the structure below), also known as IPI-504, a small-molecule inhibitor of heat shock protein 90 (HSP90) with antiproliferative and antineoplastic activities. Its chemical name is 18,21-didehydro-17-demethoxy-18,21-dideoxo-18,21-dihydroxy-17-(2-propenylamino)geldanamycin hydrochloride. Retaspimycin binds to and inhibits the cytosolic chaperone functions of HSP90, which maintains the stability and functional shape of many oncogenic signaling proteins and may be overexpressed or overactive in tumor cells. It is administered by intravenous infusion.

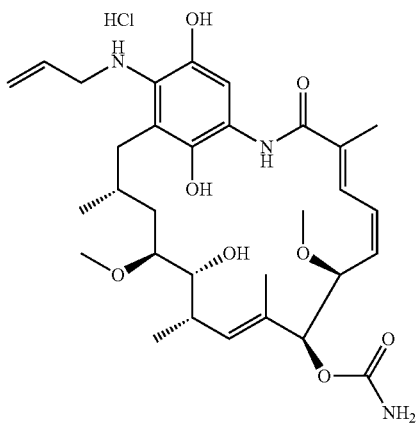 [SMILES: C=CCNc1c(O)cc2c(O)c1C[C@@H](C)C[C@H](OC)[C@H](O)[C@@H](C)/C=C(\C)[C@H](OC(N)=O)[C@@H](OC)/C=C\C=C(/C)C(=O)N2 ; Cl]

In a particular embodiment, the pharmaceutical composition comprises Solanezumab, a monoclonal antibody being developed as a neuroprotector for patients with Alzheimer's disease. It binds to the amyloid-β peptides that make up the protein plaques seen in the brains of people with the disease. Solanezumab is administered intravenously.

In a particular embodiment, the pharmaceutical composition comprises Ocrelizumab (also known as RG1594), a humanized anti-CD20 monoclonal antibody. It targets mature B lymphocytes and hence is an immunosuppressive drug candidate. Ocrelizumab is intended for the treatment of rheumatoid arthritis, lupus nephritis, and progressive joint destruction in rheumatoid arthritis. It is administered by intravenous infusion.

In a particular embodiment, the pharmaceutical composition comprises Brilacidin (also known as PMX-30063), a Defensin-mimetics antibiotics. It has shown rapid bactericidal activity against many Gram-positive and Gram-negative pathogens including methicillin-resistant *Staphylococcus aureus* (MRSA), drug resistant Enteroccus, *E. coli*, and NDM-1 drug-resistant *Klebsiella pneumonia*. Brilacidin is being evaluated in clinical trials for treatment of acute bacterial skin and skin-structure infection (ABSSSI). It is administered by intravenous infusion.

In a particular embodiment, the pharmaceutical composition comprises HEPLISAV™, hepatitis B vaccine demonstrated the potential to provide more rapid and increased protection against hepatitis B viral infection. It is comprised of 1018 immunostimulatory sequences (ISS) mixed with recombinant hepatitis B surface antigen. 1018 ISS is an unmethylated cytosine and phosphoguanosine synthetic oligodexynucleotide (ODN). HEPLISAV™ is administered by intramuscular injections.

In a particular embodiment, the pharmaceutical composition comprises HUCNS-SC®, a highly purified composition of human neural stem cells (tissue-derived or "adult" stem cells. It is being developed as a cellular therapy for the potential treatment of Batten disease, one of a group of disorders known as neural ceroid lipofuscinoses (NCL). It is also being studied for the treatment of spinal cord injury, Pelizeaus-Merzbacher Disease (PMD), and retinal degenerative diseases such as Age-related Macular Degeneration (AMD). It can be administered by transplantation (e.g., intramedullary transplantation and subretinal transplantation).

In a particular embodiment, the pharmaceutical composition comprises Albiglutide, a glucagon-like peptide-1 agonist (GLP-1 agonist) drug for the treatment of type 2 diabetes. It is a dipeptidyl peptidase-4-resistant GLP-1 dimer fused to human albumin Albiglutide is available for subcutaneous administration.

In a particular embodiment, the pharmaceutical composition comprises AIN457, a fully human monoclonal antibody that blocks action of interleukin-17A—a major trigger of inflammation involved in a variety of diseases such as uveitis, psoriasis and rheumatoid arthritis. AIN457 is available for subcutaneous administration.

In a particular embodiment, the pharmaceutical composition comprises Defibrotide, the sodium salt of a complex mixture of single-stranded oligodeoxyribonucleotides derived from porcine mucosal DNA. Its pharmacological effects include antithrombotic, anti-inflammatory and antiischemic properties. Indications include treatment of Hepatic veno-occlusive disease (VOD) and prophylaxis to prevent occurrence of VOD. Additional indications include cancer, inflammation, thrombosis, multiple myeloma, liver disease, peripheral obliterative arterial disease, thrombophlebitis, and Raynaud's phenomenon. Defibrotide is available as an oral, intravenous, and intramuscular formulation.

It can be administered intravenously in crystalloid solution (either normal saline [NS] or 5% dextrose in water [D5W]), typically as 4 divided doses, each infused over 2 hours, starting at an initial total daily dose of 10 mg/kg. Drug can be mixed with a minimum of 100 mL of NS to a maximum concentration of 400 mg/dL.

In a particular embodiment, the pharmaceutical composition comprises Daclizumab, an immunosuppressive, humanized IgG1 monoclonal antibody produced by recombinant DNA technology that binds specifically to the alpha subunit (p55 alpha, CD25, or Tac subunit) of the human high-affinity interleukin-2 (IL-2) receptor that is expressed on the surface of activated lymphocytes. Daclizumab is a composite of human (90%) and murine (10%) antibody sequences. The human sequences were derived from the constant domains of human IgG1 and the variable framework regions of the EN myeloma antibody. The murine sequences were derived from the complementarity-determining regions of a murine anti-Tac antibody. Indications include prophylaxis of acute organ rejection in adult patients receiving their first cadaveric kidney transplant, multiple sclerosis, juvenile idiopathic arthritis (JIA)-associated uveitis, leukemia, age-related macular degeneration, Hodgkin's lymphoma, graft vs host disease, uveitis, psoriasis, aplastic anemia, pure red cell aplasia, diamond blackfan anemia, cardiac transplantation, and acute allograft rejection in simultaneous kidney/pancreas transplant recipients.

Daclizumab 25 mg/5 mL can be supplied as a clear, sterile, colorless concentrate for further dilution and intravenous administration. Each milliliter of solution contains 5 mg of daclizumab and 3.6 mg sodium phosphate monobasic monohydrate, 11 mg sodium phosphate dibasic heptahydrate, 4.6 mg sodium chloride, 0.2 mg polysorbate 80, and may contain hydrochloric acid or sodium hydroxide to adjust the pH to 6.9. No preservatives are added. It can be administered subcutaneously.

In a particular embodiment, the pharmaceutical composition comprises Relaxin, a recombinant form of the human hormone relaxin-2. Mature human relaxin is an ovarian hormonal peptide of approximately 6000 daltons. Relaxlin is being developed for patients hospitalized with acute heart failure. Other indications include systemic sclerosis, pre-eclampsia, diabetes mellitus, inflammation and hypertension.

Relaxin can be formulated in a buffer that maintains the pH of said composition at about 4 to less than about 7, more preferably 4.5-5.5. Additionally, the formulation can be isotonic. Under acidic conditions the degradation rates of human relaxin as assessed by HPLC are slower at an optimal level. Preferably the relaxin is formulated at approximately pH 5 with a shelf-life (assuming an acceptable reduction of 10% in the HPLC main peak area) at 5° C. of at least 2 years. It can be administered intravenously or intramuscularly.

In a particular embodiment, the pharmaceutical composition comprises Protecan (CBLB502), a recombinant protein and an agonist of toll-like receptor 5 (TLRS), an innate immunity receptor, that acts by mobilizing antitumor immune response and reducing treatment side effects on normal tissues. Indications include suppressing growth of TLRS expressing tumors. Protecan has also been shown to have an effect on several animal models of liver metastasis, regardless of TLRS expression. Additionally, protecan evidences a supportive care benefit in preclinical models when combined with radiation treatment and cytotoxic agents with adverse gastrointestinal (GI) effects. Protecan is formulated for subcutaneous, intravenous or intramuscular infusion.

In a particular embodiment, the pharmaceutical composition comprises GATTEX®, a recombinant analog of human glucagon-like peptide 2, a protein involved in the rehabilitation of the intestinal lining. Indications include adult short bowel syndrome (SBS), Renal Impairment, and Crohn Disease. It is formulated for subcutaneous injection.

In a particular embodiment, the pharmaceutical composition comprises Brilacidin (also known as PMX-30063), a small molecule antibiotic agent designed to mimic one of the body's first lines of defense against bacteria (host defense proteins). Indications include acute bacterial skin and skin structure infections (ABSSSI) caused by *Staphylococcus aureus*, including MRSA. Currently brilacidin is formulated for intravenous (IV) application.

In a particular embodiment, the pharmaceutical composition comprises PEG-Interferon lambda, a pegylated type 3 interferon in development for the treatment of hepatitis C virus (HCV) infection. Other indications include hepatitis B. The drug is administered subcutaneously.

In a particular embodiment, the pharmaceutical composition comprises MAGE-A3, a protein encoded by the MAGEA3 gene in humans. In the medical context, it is packaged as a recombinant antigen-specific cancer immunotherapeutic (ASCI). Indications include cancers expressing the MAGE-A3 antigen, including metastatic melanoma and non-small cell lung cancer. Other indications may include bladder and liver cancers that also commonly express MAGE-A3, squamous cell Carcinoma of the head and neck, neuroblastoma, rhabdomyosarcoma, osteogenic sarcoma, multiple myeloma, ovarian cancer, acute myelogenous leukemia, and urinary bladder neoplasms. It is formulated for intramuscular (IM) or intradermal/subcutaneous administration.

In a particular embodiment, the pharmaceutical composition comprises Soluble Ferric Pyrophosphate, an inorganic chemical compound with the formula $Fe_3(OPP)_4$. Indications include end stage renal disease, chronic kidney disease, renal railure requiring hemodialysis, ESRD, iron-deficiency anemia. The drug can be administered intravenously, or via dialysate during every dialysis treatment.

In a particular embodiment, the pharmaceutical composition comprises Turoctocog alfa, a recombinant coagulation factor VIII, for the treatment of haemophilia A. It is intended to offer prevention and treatment of bleeds in people with haemophilia A. Other indications include Congenital Bleeding Disorder. The drug is administered intravenously.

In a particular embodiment, the pharmaceutical composition comprises Ixekizumab, an immunoglobulin G4 anti-interleukin-17 monoclonal antibody designed to bind proinflammatory cytokines including IL-17A, which play a role in psoriasis. Indications include chronic plaque psoriasis and rheumatoid arthritis. The drug can be administered by subcutaneous injection.

In a particular embodiment, the pharmaceutical composition comprises Epratuzumab, a humanized monoclonal antibody targeting CD22 receptors on B lymphocytes. Indications include non Hodgkin's lymphoma, systemic lupus erythematosus, waldenstrom macroglobulinemia, leukemia and lymphoma. The drug can be administered intravenously.

In a particular embodiment, the pharmaceutical composition comprises Alirocumab (REGN727/SAR236553), a human monoclonal antibody developed for the treatment of hypercholesterolemia. Alirocumab is an inhibitor of proprotein convertase subtilisin/kexin type 9 (PCSK9), an enzyme that plays a major regulatory role in cholesterol homeostasis by promoting degradation of low density lipoprotein receptor (LDLR). Alirocumab is currently in Phase III clinical trials in the United Kingdom, Europe and the United States, and is administered by subcutaneous injection.

In a particular embodiment, the pharmaceutical composition comprises Cenderitide (CD-NP), a novel chimeric 37 amino acid peptide having the following sequence: GLSKGCFGLKLDRIGSMSGLGCPSLRDPRPNAPSTSA (SEQ ID NO:8). Cenderitide was rationally designed to confer both arterial and venodilation activity and represents a fusion of two natriuretic peptides, CNP and DNP. Cenderitide is being developed for treating acutely decompensated heart failure (ADHF) patients continuously for up to 90 days after discharge from the hospital. Cenderitide is administered subcutaneously either by bolus or continuous infusion over a 24-hour period.

In a particular embodiment, the pharmaceutical composition comprises Siltuximab, a chimeric, murine-human monoclonal antibody that binds with high affinity and specificity to interleukin-6 (IL-6). The variable region of siltuximab is derived from a murine anti-IL-6 antibody, CLB8, and the constant region is derived from a human IgG1κ molecule. Siltuximab has been investigated for the treatment of metastatic renal cell cancer, prostate cancer, and Castleman's disease, among other types of cancer. It is administered by intravenous infusion.

In a particular embodiment, the pharmaceutical composition comprises Iniparib (SAR2405550/BSI-201), 4-iodo-3-nitrobenzamide represented by the following structural formula:

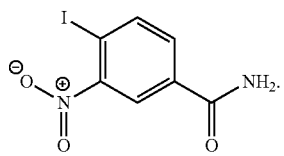 [SMILES: NC(=O)c1ccc(I)c([N+](=O)[O-])c1]

It was originally believed to be an irreversible inhibitor of Poly [ADP-ribose] polymerase 1 (PARP-1), although later studies determined that it acts by non-selectively modifying cysteine-containing proteins in tumor cells. Iniparib underwent clinical trials for the treatment of patients with non-small cell lung cancer, advanced ovarian cancer and metastatic triple negative breast cancer. Clinical trials in patients with solid tumors, inoperable brain cancer and malignant glioma are still ongoing.

Iniparib is supplied in doses of 100 mg in single-use vials of liquid at a concentration of 10 mg/mL, and is administered by intravenous infusion.

In a particular embodiment, the pharmaceutical composition comprises Palifosfamide (Zymafos), a novel formulation of isophosphoramide mustard that has the following chemical structure:

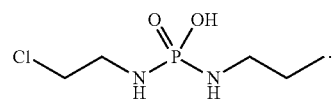

Isophosphoramide mustard is an active metabolite of ifosfamide, a chemotherapeutic agent that acts by causing irreparable DNA inter-strand cross-links in cancer cells, leading to cell death. Palifosfamide is currently indicated for treating soft tissue sarcoma and small cell lung cancer. Palifosfamide is formulated by combining the tris (hydroxymethyl) amino methane (tris) salt (palifosfamide-tris active ingredient) and a number of excipients to create the injectable (and capsule) drug product. The drug product is supplied as a lyophilized powder for reconstitution with saline prior to administration. Palifosfamide can be administered by intravenous infusion or orally.

In a particular embodiment, the pharmaceutical composition comprises Lebrikizumab (RG3637/TNX-650), a humanized monoclonal antibody against interleukin-13 (IL-13), over-expression of which can result in inflammation of airways, a feature of asthma. In a recent Phase II clinical trial, lebrikizumab was shown to significantly decrease the symptoms of asthma in patients whose disease cannot be adequately controlled with inhalable glucocorticoids. Lebrikizumab is administered by a subcutaneous injection.

In a particular embodiment, the pharmaceutical composition comprises Vonicog Alfa (BAX 111), a recombinant human Von Willebrand Factor (rVWF), consisting of 2050 amino acids and produced by Baxter International. It is currently being investigated in a Phase III clinical trial for the treatment and prevention of bleeding episodes in patients with von Willebrand disease. Baxter's preparation of rVWF does not contain blood-based additives.

In a particular embodiment, the pharmaceutical composition comprises Romosozumab (AMG 785/CDP7851), a humanized monoclonal antibody that binds to and inhibits sclerostin, a protein secreted by bone cells that inhibits bone formation. By binding to and blocking sclerostin, AMG 785/CDP7851 is designed to allow the body to add more bone to the skeleton. Romosozumab is currently being tested in a Phase III clinical trial for the treatment of osteoporosis in post-menopausal women. Romosozumab is administered by subcutaneous or intravenous injection.

In a particular embodiment, the pharmaceutical composition comprises Elotuzumab (BMS-901608), a humanized monoclonal IgG1 antibody designed to target CS1, a surface protein that is highly and uniformly expressed on multiple myeloma cells, but is not common on most normal cells. Elotuzumab (is currently being investigated in a Phase III clinical trial for treating patients with multiple myeloma. Elotuzumab (is administered by intravenous injection.

In a particular embodiment, the pharmaceutical composition comprises Otamixaban, a compound having the following structure:

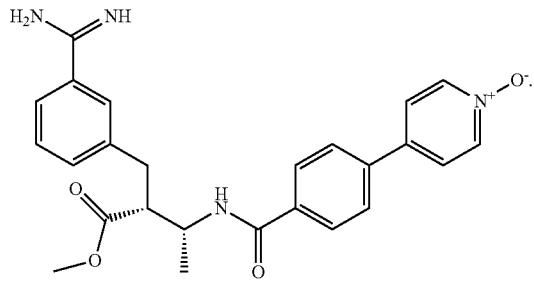

Otamixaban is an inhibitor of Factor Xa (fXa), a serine protease that catalyses the conversion of prothrombin to thrombin via the prothrombinase complex. Otamixaban is a potent ($K_i$=0.5 nM), selective, rapid acting, competitive and reversible fXa inhibitor that effectively inhibits both free and prothrombinase-bound fXa. Otamixaban has been shown in a clinical trial to reduce major coronary complications in patients with acute coronary syndrome (ACS). A clinical trial is currently under way to compare the efficacy of otamixaban to unfractionated heparin and eptifibatide in patients with unstable angina and myocardial infarction.

Otamixaban is administered by intravenous bolus injection or an intravenous infusion. It was also recently described that otamixaban formulations at pH between 3 and 5 are characterized by decreased otamixaban degradation during sterilization and storage.

In a particular embodiment, the pharmaceutical composition comprises Vedolizumab (MLN0002), a humanized monoclonal antibody being studied for the treatment of ulcerative colitis and Crohn's Disease. Vedolizumab targets α4β7 integrin (LPAM-1, lymphocyte Peyer's patch adhesion molecule 1), a member of the integrin family of cell surface receptors that is primarily expressed on mucosal lymphocytes, and is also present on NK cells and eosinophils. The α4β7 integrin heterodimer functions by directing the homing of lymphocytes into Peyer's patches and intestinal lamina propria. Vedolizumab was found in a Phase III clinical trial to be safe and effective for inducing and maintaining clinical remission in patients with moderate to severe ulcerative colitis. Vedolizumab is administered by intravenous infusion.

In a particular embodiment, the pharmaceutical composition comprises Tabalumab (LY 2127399), a fully human monoclonal antibody that was designed to have neutralizing activity against both membrane-bound and soluble forms of B-cell activating factor (BAFF). BAFF is a member of the TNF family that has been shown to be an important survival factor for peripheral B cells and has been implicated in conferring a survival advantage to B-cell malignancies, such as multiple myeloma. Clinical trials are currently under way to test tabalumab in patients with multiple myeloma, rheumatoid arthritis and lupus erythematosus. Tabalumab is administered by intravenous infusion or subcutaneous injection.

In a particular embodiment, the pharmaceutical composition comprises idiotype-KLH conjugate (Id-KLH) (BIO-VAXID®), an autologous tumor-derived immunoglobulin idiotypic vaccine being studied as a personalized therapeutic cancer vaccine for the treatment of non-Hodgkin's lymphoma, specifically targeting follicular lymphoma, mantle cell lymphoma and potentially other B-cell blood cancers. Specifically, idiotype-KLH conjugate comprises a patient's cancer/tumor-specific immunoglobulin-idiotype protein conjugated to keyhole lympethemocyanin (KLH) administered via subcutaneous injection with a protein called granulocyte-macrophage colony-stimulating factor (GM-CSF). For example, the immunoglobulin-idiotype can be derived from a patient's follicular lymphoma biopsy.

In a particular embodiment, the pharmaceutical composition comprises Velimogene aliplasmid (ALLOVECTIN® or ALLOVECTIN-7®), a plasmid-based immunotherapeutic that encodes human leukocyte antigen-B7 (HLA-B7) and β-2 microglobulin that together form an MHC class 1 complex. It is designed to induce allogeneic and tumor-antigen-specific T-cell responses against tumor cells. Velimogene aliplasmid is being studied in subjects with recurrent metastatic melanoma, particularly Stage III and IV melanoma, where it is intended to provide advantages over current first-line therapies such as improved efficacy, better safety profile, and simple outpatient administration. The plasmid Velimogene aliplasmid has a unique set of mechanisms of action: it teaches the immune system to recognize and destroy tumor cells through an allogeneic anti-tumor response, restores tumor-associated antigen presentation via MHC class 1, and boosts the immune response through a lipid/DNA-induced danger signal.

Additionally, Velimogene aliplasmid's mechanisms of action are applicable to any type of accessible, immunoreactive solid tumor, providing multiple follow-on indications, such as breast cancer, prostate cancer, and head and neck cancer. Velimogene aliplasmid is currently being administered using a conventional needle and syringe administration into a lesion from a single vial.

In a particular embodiment, the pharmaceutical composition comprises Sarilumab (REGN88/SAR153191), a fully human monoclonal antibody directed against the alpha subunit of the IL-6 receptor complex (IL-6R Alpha) being studied in patients with rheumatoid arthritis (RA) and including those who are Inadequate Responders to Methotrexate (MTX) Therapy. Sarilumab is a high affinity, specific inhibitor of IL-6 signaling. It blocks the binding of IL-6 to its receptor and interrupts the resultant cytokine-mediated inflammatory signaling cascade. Sarilumab is subcutaneously administered to patients.

In a particular embodiment, the pharmaceutical composition comprises Analog Insulin-PH20, formulations combining two ultrafast insulin analog products, lispro (HUMALOG®) and aspart, with a recombinant human hyaluronidase (rHuPH20) enzyme. Analog-PH20 formulations are subcutaneously administered to patients with Type 1 and 2 diabetes.

Insulin Lispro and aspart are presently indicated to improve glycemic control in adults and children with diabetes mellitus. Insulin Lispro is presently formulated as a solution with glycerin, dibasic sodium phosphate, Metacresol, zinc oxide, trace amounts of phenol, and Water for Injection.

The insulin lispro solution has a pH of 7.0 to 7.8. The pH is adjusted by addition of aqueous solutions of hydrochloric acid 10% and/or sodium hydroxide 10%. Insulin aspart, such as the one sold under the name NOVOLOG®, is presently formulated with glycerin, phenol, metacresol, zinc, disodium hydrogen phosphate dihydrate, sodium chloride and water for injection. NOVOLOG® has a pH of 7.2-7.6. Hydrochloric acid 10% and/or sodium hydroxide 10% may be added to adjust pH.

In a particular embodiment, the pharmaceutical composition comprises recombinant human hyaluronidase (rH-uPH20; HYLENEX®), approved by the FDA as an aid to the absorption and dispersion of other injectable drugs. Specifically, recombinant human hyaluronidase is indicated as an adjuvant in subcutaneous fluid administration for achieving hydration; as an adjuvant to increase the dispersion and absorption of other injected drugs; and as an adjunct in subcutaneous urography for improving resorption of radiopaque agents.

Recombinant human hyaluronidase is formulated with sodium chloride, dibasic sodium phosphate, albumin human, edetate disodium, calcium chloride, and sodium hydroxide added for pH adjustment to approximately pH 7.0.

In a particular embodiment, the pharmaceutical composition comprises a formulation of lixisenatide (LYXUMIA®) in combination with insulin glargine (LANTUS®), which is being studied in patients with Type 2 Diabetes. Lixisenatide is a glucagon-like peptide-1 agonist (GLP-1) in development for the treatment of patients with type 2 diabetes mellitus. Insulin glargine is a long-acting human insulin analog presently indicated to improve glycemic control in adults and children with type 1 diabetes mellitus and in adults with type 2 diabetes mellitus. Insulin glargine is currently administered via subcutaneous injection and is formulated with zinc, m-cresol, glycerol 85%, and water for injection. The pH is adjusted by addition of aqueous solutions of hydrochloric acid and sodium hydroxide. Insulin glargine has a pH of approximately 4.

In a particular embodiment, the pharmaceutical composition comprises CXA-201, a combination consisting of CXA-101 (ceftolozane), a novel, rapidly-bactericidal cephalosporin with broad Gram-negative activity and particularly potent activity against *Pseudomonas aeruginosa*, along with tazobactam, a well-known beta-lactamase inhibitor that is a component of the long-established antibiotic, ZOSYN®. CXA-201 is being used for treatment of certain serious Gram-negative bacterial infections, including those caused by multi-drug resistant *Pseudomonas aeruginosa*. For example, it is being studied in patients with complicated Urinary Tract Infections (cUTI), including pyelonephritis; complicated intra-abdominal infections (cIAI); and nosocomial pneumonia. CXA-201 is administered intravenously.

In a particular embodiment, the pharmaceutical composition comprises Eteplirsen or AVI-4658, a phosphorodiamidate morpholino oligomer (PMO) designed to keep a section of the dystrophin gene called exon 51 from being included in the final genetic instructions that cells use to make the muscle protein dystrophin Eteplirsen is being stufied for treatment of Duchenne Muscular Dystrophy (DMD). Eteplirsen is administered by intravenous infusion.

In a particular embodiment, the pharmaceutical composition comprises hGH-CTP (MOD-4023), a Human Growth Hormone (hGH) that is modified with carboxyl terminal peptide (CTP) and is being used for the long-term treatment of children and adults with growth failure due to inadequate secretion of endogenous growth hormone. The primary indications of hGH in children are growth hormone deficiency, kidney disease, Prader-Willi Syndrome, and Turner's Syndrome. hGH-CTP is administered by subcutaneous injection.

In a particular embodiment, the pharmaceutical composition comprises ICT-107, a personalized, multi-epitope pulsed dendritic cell vaccine that is being studied for the personalized treatment of Glioblastoma Multiforme (GBM). Leukapheresis was used to isolate mononuclear cells which were differentiated into dendritic cells in culture, pulsed with tumor associate antigen (TAA) peptides including epitopes to HER2, TRP-2, gp100, MAGE-1, IL13Ra2, and AIM-2, and then administered intradermally to patients. The goal is for the ICT-107 vaccine to stimulate the patient's immune response to kill the remaining GBM tumor cells after surgery and chemotherapy.

In a particular embodiment, the pharmaceutical composition comprises IDegLira (NN9068), a combination of liraglutide (VICTOZA®) and insulin degludec, ultra-long-acting basal insulin, being stufied for the treatment of type 2 diabetes. Liraglutide is a glucagon-like peptide-1 (GLP-1) receptor agonist indicated as an adjunct to diet and exercise to improve glycemic control in adults with type 2 diabetes mellitus. IdegLira is administered by subcutaneous injection.

In a particular embodiment, the pharmaceutical composition comprises Nivolumab (ONO-4538; BMS-936558; MDX-1106), a monoclonal antibody that is a programmed death 1 (PD-1) antagonist being studied for metastic melanoma, non-small cell lung cancer (NSCLC), renal clear cell cancer (RCC), hormone refractory prostate cancer (HRPC), and colorectal cancer (CRC). Nivolumab is administered intravenously.

In a particular embodiment, the pharmaceutical composition comprises Recombinant Factor VIII Fc fusion protein (rFVIIIFc). rFVIIIFc is a fully recombinant clotting factor designed to be administered to previously-treated subjects with severe hemophilia A by replacing the protein that hemophilia A patients lack. rFVIIIFc has been found to last longer in the body than commercially available Factor VIII products. rFVIIIFc has been developed using monomeric Fc-fusion technology, which leverages a natural mechanism that recycles rFVIIIFc in the circulation to extend its half-life. rFVIIIFc is being evaluated in a Phase II/III registrational, open-label, multicenter trial (A-LONG) designed to evaluate its safety, pharmacokinetics and efficacy in the prevention and treatment of bleeding in previously treated patients with severe hemophilia A.

In a particular embodiment, the pharmaceutical composition comprises TH-302 (shown below), an experimental cancer treatment that is in clinical development. TH-302 exploits the activation of a nitroazole prodrug by a process that involves a one electron reduction mediated by ubiquitous cellular reductases such as the NADPH cytochrome P450 to generate a radical anion prodrug (RP). In the presence of oxygen (normoxia) the radical anion prodrug reacts rapidly with oxygen to generate the original prodrug and superoxide (SO). Under the low oxygen conditions of the hypoxic zones in tumors, however, the radical anion prodrug undergoes further irreversible reductions to the hydroxylamine (HA) followed by elimination, releasing the active drug and an azole derivative (AZ).

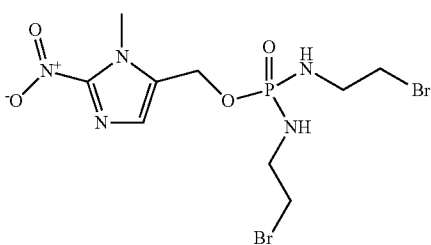

N,N'-Bis(2-bromoethyl)phosphorodiamidic acid (1-methyl-2-nitro-1H-imidazol-5-yl)methyl ester In a particular embodiment, the pharmaceutical composition comprises GSK 2402968, which consists of short pieces of DNA called "antisense oligonucleotides" or "AONs" that are being tested for their ability to convert deletions near Exon 51 in the dystrophin gene from nonfunctional "out-of-frame" deletions to more functional "in-frame" deletions, such as those typically seen in boys and men with Becker muscular dystrophy. The strategy is commonly called "exon-skipping".

Although variations on this strategy might ultimately be used to try to correct deletions in many parts of the dystrophin gene, GSK 2402968 targets the following deletions: 45-50, 47-50, 48-50, 49-50, 50, 52.

In a particular embodiment, the pharmaceutical composition comprises Trastuzumab emtansine (also called trastuzumab-DM1 or trastuzumab-MCC-DM1, abbreviated T-DM1), an antibody-drug conjugate consisting of the antibody trastuzumab (the active ingredient in HERCEPTIN®) linked to a cytotoxic agent that is a derivative of maytansine (DM1) (see below). It is in clinical trials for breast cancer, especially of the HER2 positive type.

product, also referred to as Algenpantucel-L, HyperAcute Pancreas is made up of equal doses of two separate, non-patient specific pancreatic cancer cell lines genetically engineered to express an enzyme called α-Ga. The enzyme isn't found in human pancreatic cancer cells, but genetically engineered pancreatic cancer cells do share some molecules with the natural form disease. It is believed that the body will attack the genetically engineered cells, and in the process train the immune system to recognize and destroy the naturally occurring version of pancreatic cancer.

In a particular embodiment, the pharmaceutical composition comprises AMG, a humanized IgG2 mAb, which is being investigated as a nerve growth factor (NGF) antagonist, in neuropathic pain.

In a particular embodiment, the pharmaceutical composition comprises HGT-1110, which is currently being investigated as an enzyme replacement therapy administered intrathecally, in children with Metachromatic Leukodystrophy (MLD).

In a particular embodiment, the pharmaceutical composition comprises RIGScan CR, a monoclonal antibody that targets a telltale colorectal cancer marker called TAG-72, which is also common in many epithethelial cell-derived tumors, including some breast tumors, invasive ductal tumors, non-small cell lung tumors, epithelial ovarian tumors, and the majority of gastric, pancreatic and esophageal cancers.

In a particular embodiment, the pharmaceutical composition comprises NECITUMUMAB, a monoclonal antibody, which binds to the epidermal growth factor receptor (EGFR) and is currently being investigated as antineoplactic agent for its effects on non-small cell lung carcinoma.

In a particular embodiment, the pharmaceutical composition comprises Semuloparin (VISAMERIN®/MUL-SEVO®), an ultra-low molecular weight heparin which

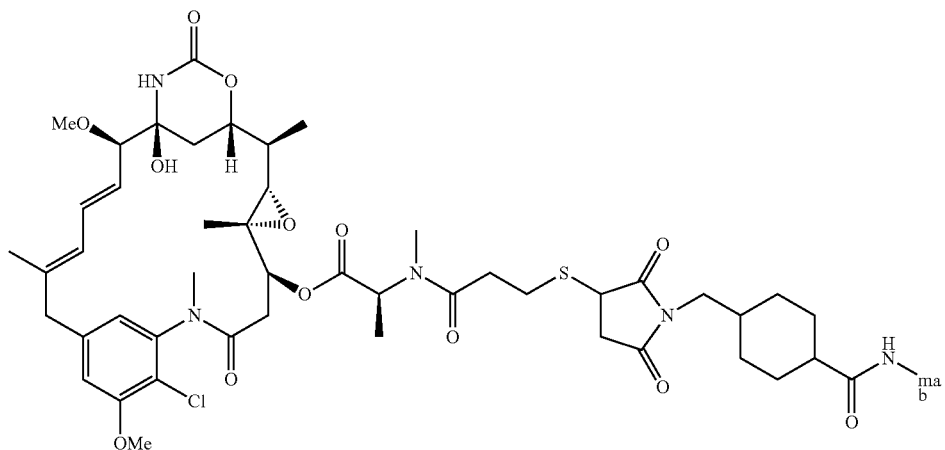

In a particular embodiment, the pharmaceutical composition comprises NATPARA®, a bioengineered replica of human parathyroid hormone. NATPARA® is identical in structure to the 84-amino acid single-chain polypeptide human parathyroid hormone and mimics the action of the natural parathyroid hormone. NATPARA® is currently being investigated to treat hypoparathyroidism, a rare disorder in which the body produces insufficient levels of parathyroid hormone.

In a particular embodiment, the pharmaceutical composition comprises HyperAcute Pancreas immunotherapy targets factor Xa and Thrombin (factor IIa). Semuloparin acts to prevent blood clots and is considered as an alternative to standard heparins for antithrombotic effects. Semuloparin is classified as an ultra-LMWH because of its low molecular mass of 2000-3000 Daltons on average. (Enoxaparin has 4500 Daltons.) These low mass heparins have lower antithrombin activity than classical LMWHs and act mainly on factor Xa, therefore reducing the risk of bleeding, that has sometimes been a problem with traditional herparins.

In a particular embodiment, the pharmaceutical composition comprises Recombinant Human Heparan N-Sulfatase (rhHNS), or HGT-1410, which is designed for intrathecal administration via an intrathecal drug delivery device to patients with Sanfilippo Syndrome Type A (MPS IIIA).

In a particular embodiment, the pharmaceutical composition comprises Pertuzumab (RG1273), a humanized monoclonal antibody designed to prevent HER2 dimerisation, a process that is believed to play an important role in the growth and formation of several different cancer types. The mechanism of action of pertuzumab is thought to be complementary to HERCEPTIN®, as both bind to the HER2 receptor but on different regions. The goal of combining pertuzumab with HERCEPTIN® and chemotherapy is to determine if the combination may provide a more comprehensive blockade of HER signalling pathways.

In a particular embodiment, the pharmaceutical composition comprises Brentuximab vedotin (ADCETRIS), an antibody-drug conjugate approved to treat anaplastic large cell lymphoma (ALCL) and Hodgkin lymphoma. Brentuximab vedotin is a CD30-directed antibody-drug conjugate (ADC) (structure shown below) consisting of three components: 1) the chimeric IgG1 antibody cAC10, specific for human CD30, 2) the microtubule disrupting agent MMAE, and 3) a protease-cleavable linker that covalently attaches MMAE to cAC10.

Brentuximab vedotin is available for injection in a single-use vial containing 50 mg of brentuximab vedotin as a sterile, white to off-white lyophilized, preservative-free cake or powder.

In a particular embodiment, the pharmaceutical composition comprises adjuvanted recombinant varicella zoster virus (VZV) subunit vaccine (HZ/su), which is being developed for the prevention of herpes zoster and its complications.

In a particular embodiment, the pharmaceutical composition comprises cixutumumab (IMC-A12), a monoclonal antibody for the treatment of solid tumors. It is a fully human IgG1 monoclonal antibody directed against the human insulin-like growth factor-1 receptor (IGF-1R) with potential antineoplastic activity. Cixutumumab selectively binds to membrane-bound IGF-1R, thereby preventing the binding of the natural ligand IGF-1 and the subsequent activation of PI3K/AKT signaling pathway. Downregulation of the PI3K/AKT survival pathway may result in the induction of cancer cell apoptosis and may decrease cancer cellular proliferation. IGF-1R, a receptor tyrosine kinase of the insulin receptor superfamily overexpressed by many cancer cell types, stimulates cell proliferation, enables oncogenic transformation, and suppresses apoptosis; IGF-1R signaling has been implicated in tumorigenesis and metastasis.

Degradation and Stability of Pharmaceutical Compositions

According to the present invention, delamination resistant pharmaceutical containers comprising a glass composition provide for improved resistance to degradation of, improved stability of, improved resistance to inactivation of, and improved maintenance of levels of a pharmaceutical composition having at least one active pharmaceutical ingredient.

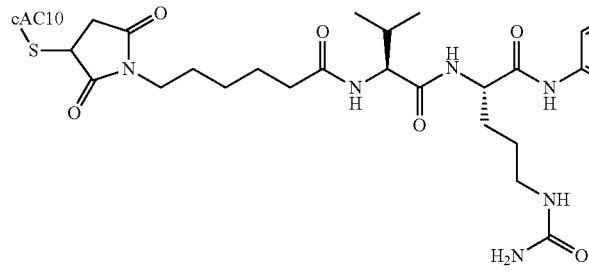
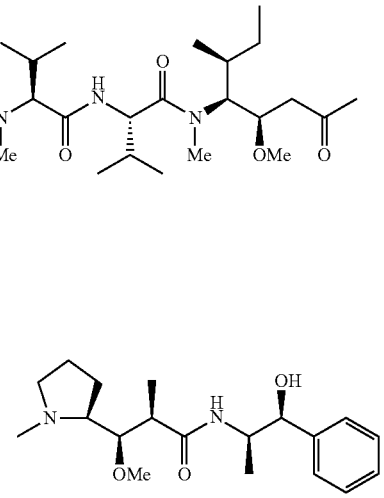

Brentuximab vedotin has an approximate molecular weight of 153 kDa. Approximately 4 molecules of MMAE are attached to each antibody molecule. Brentuximab vedotin is produced by chemical conjugation of the antibody and small molecule components. The antibody is produced by mammalian (Chinese hamster ovary) cells, and the small molecule components are produced by chemical synthesis.

Brentuximab vedotin for Injection is supplied as a sterile, white to off-white, preservative-free lyophilized cake or powder in single-use vials. Following reconstitution with 10.5 mL Sterile Water for Injection, USP, a solution containing 5 mg/mL brentuximab vedotin is produced. The reconstituted product contains 70 mg/mL trehalose dihydrate, 5.6 mg/mL sodium citrate dihydrate, 0.21 mg/mL citric acid monohydrate, and 0.20 mg/mL polysorbate 80 and water for injection. The pH is approximately 6.6.

In one embodiment of the present invention, the delamination resistant pharmaceutical containers provide improved stability to pharmaceutical compositions contained therein. As used herein, the term "stability" refers to the ability of an active pharmaceutical ingredient to essentially retain its physical, chemical and conformational identity and integrity upon storage in the pharmaceutical containers of the invention. Stability is associated with the ability of an active pharmaceutical ingredient to retain its potency and efficacy over a period of time. Instability of an active pharmaceutical ingredient may be associated with, for example, chemical or physical degradation, fragmentation, conformational change, increased toxicity, aggregation (e.g., to form higher order polymers), deglycosylation, modification of glycosylation, oxidation, hydrolysis, or any other structural, chemical or physical modification. Such physical, chemical and/or conformational changes often result in reduced activity or inactivation of the active pharmaceutical ingredient, for example, such that at least one biological activity of the active pharmaceutical ingredient is reduced or eliminated. Alternatively or in addition, such physical, chemical and/or conformational changes often result in the formation of structures toxic to the subject to whom the pharmaceutical composition is administered.

The pharmaceutical containers of the present invention maintain stability of the pharmaceutical compositions, in part, by minimizing or eliminating delamination of the glass composition which forms, at least in part, the pharmaceutical container. In addition, the pharmaceutical containers of the present invention maintain stability of the pharmaceutical compositions, in part, by reducing or preventing the interaction of the active pharmaceutical ingredient with the pharmaceutical container and/or delaminated particles resulting therefrom. By minimizing or eliminating delamination and, further, by reducing or preventing interaction, the pharmaceutical containers thereby reduce or prevent the destabilization of the active pharmaceutical ingredient.

The pharmaceutical containers of the present invention provide the additional advantage of preventing loss of active pharmaceutical ingredients. For example, by reducing or preventing the interaction of and, thus, the adherence of, the active pharmaceutical ingredient with the pharmaceutical container and/or delaminated particles resulting therefrom, the level of active pharmaceutical ingredient available for administration to a subject is maintained.

In one embodiment of the present invention, the pharmaceutical composition has a high pH. According to the present invention, it has been discovered that high pHs serve to increase delamination of glass compositions. Accordingly, the pharmaceutical containers of the present invention are particularly suitable for storing and maintaining pharmaceutical compositions having a high pH, for example, pharmaceutical compositions having a pH between about 7 and about 11, between about 7 and about 10, between about 7 and about 9, or between about 7 and about 8.

In additional embodiments, the pharmaceutical containers of the present invention are particularly suitable for storing and maintaining pharmaceutical compositions having phosphate or citrate based buffers. According to the present invention, it has been discovered that phosphate or citrate based buffers serve to increase delamination of glass compositions. According in particular embodiments, the pharmaceutical composition includes a buffer comprising a salt of citrate, e.g., sodium citrate, or SSC. In other embodiments, the pharmaceutical composition includes a buffer comprising a salt of phosphate, e.g., mono or disodium phosphate.

In additional embodiments, the pharmaceutical containers of the present invention are particularly suitable for storing and maintaining active pharmaceutical ingredient that needs to be subsequently formulated. In other embodiments, the pharmaceutical containers of the present invention are particularly suitable for storing and maintaining a lyophilized pharmaceutical composition or active pharmaceutical ingredient that requires reconstitution, for example, by addition of saline.

Assaying for Delamination of Pharmaceutical Containers

As noted above, delamination may result in the release of silica-rich glass flakes into a solution contained within the glass container after extended exposure to the solution. Accordingly, the resistance to delamination may be characterized by the number of glass particulates present in a solution contained within the glass container after exposure to the solution under specific conditions. In order to assess the long-term resistance of the glass container to delamination, an accelerated delamination test was utilized. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg/min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers. Table 7 summarizes some non-limiting examples of sample volumes and numbers of containers for testing is shown below:

TABLE 7

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 2 | 4 | 3.2 | 4 | 10 | 128 |
| 3.5 | 7 | 5.6 | 2 | 10 | 112 |
| 4 | 6 | 4.8 | 3 | 10 | 144 |

TABLE 7-continued

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 5 | 10 | 8 | 2 | 10 | 160 |
| 6 | 10 | 8 | 2 | 10 | 160 |
| 8 | 11.5 | 9.2 | 2 | 10 | 184 |
| 10 | 13.5 | 10.8 | 1 | 10 | 108 |
| 20 | 26 | 20.8 | 1 | 10 | 208 |
| 30 | 37.5 | 30 | 1 | 10 | 300 |
| 50 | 63 | 50.4 | 1 | 10 | 504 |

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles due based on the aspect ratio of the particle (i.e., the ratio of the width of the particle to the thickness of the particle). Delamination produces particulate flakes or lamellae which are irregularly shaped and are typically >50 µm in diameter but often >200 µm. The thickness of the flakes is usually greater than about 100 nm and may be as large as about 1 µm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

In the embodiments described herein, glass containers which average less than 3 glass particles with a minimum width of 50 µm and an aspect ratio of greater than 50 per trial following accelerated delamination testing are considered "delamination resistant." In the embodiments described herein, glass containers which average less than 2 glass particles with a minimum width of 50 µm and an aspect ratio of greater than 50 per trial following accelerated delamination testing are considered "delamination-stable." In the embodiments described herein, glass containers which average less than 1 glass particle with a minimum width of 50 µm and an aspect ratio of greater than 50 per trial following accelerated delamination testing are considered "delamination-proof." In the embodiments described herein, glass containers which have 0 glass particles with a minimum width of 50 µm and an aspect ratio of greater than 50 per trial following accelerated delamination testing are considered "delamination-free".

Assessing Stability of Pharmaceutical Compositions

As set forth above, any of a variety of active pharmaceutical ingredients can be incorporated within the claimed pharmaceutical container including, for example, a small molecule, a polypeptide mimetic, a biologic, an antisense RNA, a small interfering RNA (siRNA), etc. These active ingredients degrade in varying manners and, thus, assessing the stability thereof in the pharmaceutical containers of the present invention requires different techniques.

Depending on the nature of the active pharmaceutical ingredient, the stability, maintenance and/or continued efficacy of the pharmaceutical compositions contained within the delamination resistant pharmaceutical containers of the present invention can be evaluated as follows.

A. Biologics

Biologics API are often susceptible to degradation and/or inactivation arising from various factors, including pH, temperature, temperature cycling, light, humidity, etc. Biologics API are further susceptible to degradation, inactivation or loss, arising from interaction of the pharmaceutical composition with the pharmaceutical container, or delaminants leeching therefrom. For example, biologics may undergo physical degradation which may render the resulting pharmaceutical composition inactive, toxic or insufficient to achieve the desired effect. Alternatively, or in addition, biologics may undergo structural or conformational changes that can alter the activity of the API, with or without degradation. For example, proteins may undergo unfolding which can result in effective loss and inactivity of the API. Alternatively, or in addition, biologics may adhere to the surface of the container, thereby rendering the API administered to the subject insufficient to achieve the desired effect, e.g., therapeutic effect.

(i) General Methods for Investigation of Biologic Compound Degradation

Depending on the size and complexity of the biologic, methods for analysis of degradation of non-biologic, small molecule API may be applied to biologics. For example, peptides and nucleic acids can be analyzed using any of a number of chromatography and spectrometry techniques applicable to small molecules to determine the size of the molecules, either with or without protease or nuclease digestion. However, as proper secondary and tertiary structures are required for the activity of biologics, particularly protein biologics, confirmation of molecular weight is insufficient to confirm activity of biologics. Protein biologics containing complex post-translational modifications, e.g., glycosylation, are less amenable to analysis using chromatography and spectrometry. Moreover, complex biologics, e.g., vaccines which can include complex peptide mixtures, attenuated or killed viruses, or killed cells, are not amenable to analysis by most chromatography or spectrometry methods.

(ii) In Vitro Functional Assays for Investigation of Compound Stability

One or more in vitro assays, optionally in combination with one or more in vivo assays, can be used to assess the stability and activity of the API. Functional assays to determine API stability can be selected based on the structural class of the API and the function of the API. Exemplary assays are provided below to confirm the activity of the API after stability and/or stress testing. It is understood that assays should be performed with the appropriate controls (e.g., vehicle controls, control API not subject to stress or stability testing) with a sufficient number of dilutions and replicate samples to provide data with sufficient statistical significance to detect changes in activity of 10% or less, preferably 5% or less, 4% or less, more preferably 3% or less, 2% or less, or 1% or less, as desired. Such considerations in the art are well understood.

For example, antibody based therapeutics, regardless of the disease or condition to be treated, can be assayed for stability and activity using assays that require specific binding of the antibody to its cognate antigen, e.g., ELISA. The antigen used in the ELISA should have the appropriate conformational structure as would be found in vivo. Antibody based API are used, for example, for the treatment of cancer and inflammatory diseases including autoimmune diseases. Antibody based API include, but are not limited to, adalimumab, bevacizumab, rituximab, trastuzumab, infliximab, eculizumab, ustekinumab, ranibizumab, pertuzumab, denosumab, tocilizumab, ipilimumab, natlizumab, ranibizumab, infliximab, golimumab, trastuzumab emtansine, bavituximab, onartuzmab, obinutuzumab, alemtuzumab, ramucirumab, solanezumab, ocrelizumab, secukinumab, daclizumab, ixekizumab, epratuzumab, alirocumab, siltuximab, lebrikizumab, romosozumab, elotuzumab, vedolizumab, tabalumab, sarilumab, nivolumab, trastuzumab emtansine, fulranumab, minretumomab, necitumumab, pertuzumab, brentuximab vedotin, and cixutumumab.

ELISA assays to assay the concentration of a protein biologic API are commercially available from a number of sources, e.g., R&D Systems, BD Biosciences, AbCam, Pierce, Invitrogen.

API are frequently targeted to receptors, particularly cell surface receptors. Receptor binding assays can be used to assess the activity of such agents. API that bind cell surface receptors can be agonists or antagonists. API that bind cell surface receptors need not bind the same location as the native ligand to inhibit signaling through the receptor. Depending on the activity of the API, an appropriate assay can be selected, e.g., assay for stimulation of receptor signaling when the API is a receptor agonist; and inhibition assay in which binding of an agonist, e.g., inhibition of activation by a receptor agonist by the API. Such assays can be used regardless of the disease(s) or condition(s) to be treated with the API. Modulation of cellular activity, e.g., cell proliferation, apoptosis, cell migration, modulation of expression of genes or proteins, differentiation, tube formation, etc. is assayed using routine methods. In other assay methods, a reporter construct is used to indicate activation of the receptor. Such methods are routine in the art. APIs that bind to cell surface receptors are used, for example, as anti-cancer agents, anti-diabetic agents, anti-inflammatory agents for the treatment of inflammatory mediated diseases including autoimmune disorders, anti-angiogenic agents, anti-cholinergic agents, bone calcium regulators, muscle and vascular tension regulators, and psychoactive agents. Receptor binding API include, but are not limited to, insulin in its various forms, filgrastim, pegfilgrastim, trastuzumab, epoetin alfa, and denosumab.

Modulators of cell proliferation can be assayed for activity using a cell proliferation assays. For example, cell proliferation is induced using anti-anemic agents or stimulators of hematopoietic cell growth. Anti-proliferative agents, e.g., cytotoxic agents, anti-neoplastic agents, chemotherapeutic agents, cytostatic agents, antibiotic agents, are used to inhibit growth of various cell types. Some anti-inflammatory agents also act by inhibiting proliferation of immune cells, e.g., blast cells. In proliferation assays, replicate wells containing the same number of cells are cultured in the presence of the API. The effect of the API is assessed using, for example, microscopy or fluorescence activated cell sorting (FACS) to determine if the number of cells in the sample increased or decreased in response to the presence of the API. It is understood that the cell type selected for the proliferation assay is dependent on the specific API to be tested. Modulators of cell proliferation include, but are not limited to, bevacizumab, rituximab, trastuzumab, pertuzumab, ipilimumab, carfilzomib, bortezomib, gemcitabine elaidtae, trastuzumab, REOLYSIN®, yttrium Y-90 clivatuzumab tetraxetan, AEZS-108, bavituximab, onartuzumab, imetelstat sodium, algenpantucel-L, velimogene aliplasmid, obinutuzumab, ganetespib, CUDC-101, doxorubicin hydrochloride, ramucirumab, vosaroxin, retaspimycin hydrochloride, astuprotimut-R, siltuximab, iniparib, palifosamide, elotuzumab, BIOVAXID®, velimogene aliplasmid, ICT-107, nivolumab, TH-302, trastuzumab emtansine, necitumumab, pertuzumab, brentuximab vedotin, cixtumumab, darbepoetin alfa, tedizolid phosphate, ceftaroline fosamil, brilacidin, ferric pyrophosphate, ceftolozane sulfate/tazobactam sodium, filgrastim, and perfilgrastim.

Modulators of angiogenesis can be assayed using cell migration and/or tube formation assays. For cell migration assays, human vascular endothelial cells (HUVECs) are cultured in the presence of the API in transwell devices. Migration of cells through the device at the desired time intervals is assessed. Alternatively, 3-dimensional HUVECs cultures in MATRIGEL can be assessed for tube formation. Anti-angiogenic agents are used, for example, for the treatment of cancer, macular degeneration, and diabetic retinopathy. Modulators of angiogenesis include, but are not limited to, bevacizumab, ranibizumab, and afilibercept.

Anti-inflammatory API can be assayed for their effects on immune cell stimulation as determined, for example, by modulation of one or more of cytokine expression and secretion, antigen presentation, migration in response to cytokine or chemokine stimulation, and immune cell proliferation. In such assays, immune cells are cultured in the presence of the API and changes in immune cell activity are determined using routine methods in the art, e.g., ELISA and cell imaging and counting. Anti-inflammatory agents and agents for treatment of autoimmune disease include, but are not limited to, adalimumab, infliximab, etanercept, abatacept, interferon beta-1a, natalizumab, certolizumab pegol, inflixamib, peginterferon alfa-2, golimumab, ocrelizumab, daclizumab, basiliximab, ixekizumab, tabalumab, sarilumab, and vedolizumab.

Anti-diabetic API can be assayed for their effects on insulin signaling, including insulin signaling in response to modulated glucose levels, and insulin secretion. Insulin signaling can be assessed by assessing kinase activation in response to exposure to insulin and/or modulation of glucose levels. Insulin secretion can be assessed by ELISA assay. Anti-diabetic agents include, but are not limited to, degludec, insulin aspart/insulin degludec, dulaglutide, lixisenatide, hyaluronidase (human) insulin, recombinant insulin glargine, insulin lispro, exenatide, albiglutide, insulin glargine+lixisenatide, and insulin degludec+liraglutide.

Modulators of blood clotting, i.e., fibrinolytics, anti-fibrinolytics, and anti-coagulants, can be assayed for their effects using an INR assay on serum by measuring prothrombin time to determine a prothrombin ratio. Time to formation of a clot is assayed in the presence or absence of the API. Modulators of blood clotting include, but are not limited ot, enoxaparin, coagulation factor VIIa (recombinant), octocog alfa, aptacog alfa, turoctocog alfa, vonicog alfa, otamixaban, factor VIII, defibrotide, and semuloparin sodium.

Modulators of muscle or vascular tone can be assayed for their effects using vascular or muscle explants. The tissue can be placed in a caliper for detection of changes in length and/or tension. Whole coronary explants can be used to assess the activity of API on heart. The tissue is contacted with the API, and optionally agents to alter vascular tone (e.g., $K^+$, $Ca^{++}$). The effects of the API on length and/or tension of the vasculature or muscle is assessed. Modulators of muscle or vascular tone include botulinum toxin type A, serelaxin, and cenderitide.

Psychoactive agents can act by modulation of neurotransmitter release and/or recycling. Neuronal cells can be incubated in the presence of an API and stimulated to release neurotransmitters. Neurotransmitter levels can be assessed in the culture medium collected at defined time points to detect alterations in the level of neurotransmitter present in the media. Neurotransmitters can be detected, for example, using ELISA, LC/MS/MS, or by preloading the vesicles with radioactive neurotransmitters to facilitate detection.

(iii) In Vivo Assays for Investigation of Compound Stability

In addition to in vitro testing for compound stability, API can also be tested in vivo to confirm the stability of the API after storage and/or stress testing. For example, some API are not amenable to testing using in vitro assays due to the complexity of the disease state or the complexity of the response required. For example, psychoactive agents, e.g., antipsychotic agents, anti-depressant agents, nootropic agents, immunosuppressant agents, vasotherapeutic agents, muscular dystrophy agents, central nervous system modulating agents, antispasmodic agents, bone calcium regenerating agents, anti-rheumatic agents, anti-hyperlipidemic agents, hematopoietic proliferation agents, growth factors, vaccine agents, and imaging agents, may not be amenable to full functional characterization using in vitro models. Moreover, for some agents, factors that may not alter in vitro activity may alter activity in vivo, e.g., antibody variable domains may be sufficient to block signaling through a receptor, but the Fc domains may be required for efficacy in the treatment of disease. Further, changes in stability may result in changes in pharmacokinetic properties of an API (e.g., half-life, serum protein binding, tissue distribution, CNS permeability). Finally, changes in stability may result in the generation of toxic degradation or reaction products that would not be detected in vivo. Therefore, confirmation of pharmacokinetic and pharmacodynamic properties and toxicity in vivo is useful in conjunction with stability and stress testing.

(iv) Pharmacokinetic Assays

Pharmacokinetics includes the study of the mechanisms of absorption and distribution of an administered drug, the rate at which a drug action begins and the duration of the effect, the chemical changes of the substance in the body (e.g. by metabolic enzymes such as CYP or UGT enzymes) and the effects and routes of excretion of the metabolites of the drug. Pharmacokinetics is divided into several areas including the extent and rate of absorption, distribution, metabolism and excretion. This is commonly referred to as the ADME scheme:

Absorption—the process of a substance entering the blood circulation.

Distribution—the dispersion or dissemination of substances throughout the fluids and tissues of the body.

Metabolism (or Biotransformation)—the irreversible transformation of parent compounds into daughter metabolites.

Excretion—the removal of the substances from the body. In rare cases, some drugs irreversibly accumulate in body tissue.

Elimination is the result of metabolism and excretion.

Pharmacokinetics describes how the body affects a specific drug after administration. Pharmacokinetic properties of drugs may be affected by elements such as the site of administration and the dose of administered drug, which may affect the absorption rate. Such factors cannot be fully assessed using in vitro models.

The specific pharmacokinetic properties to be assessed for a specific API in stability testing will depend, for example, on the specific API to be tested. In vitro pharmacokinetic assays can include assays of drug metabolism by isolated enzymes or by cells in culture. However, pharmacokinetic analysis typically requires analysis in vivo.

As pharmacokinetics are not concerned with the activity of the drug, but instead with the absorption, distribution, metabolism, and excretion of the drug, assays can be performed in normal subjects, rather than subjects suffering from a disease or condition for which the API is typically administered, by administration of a single dose of the API to the subject. However, if the subject to be treated with the API has a condition that would alter the metabolism or excretion of the API, e.g., liver disease, kidney disease, testing of the API in an appropriate disease model may be useful. Depending on the half life of the compound, samples (e.g., serum, urine, stool) are collected at predetermined time points for at least two, preferably three half-lives of the API, and analyzed for the presence of the API and metabolic products of the API. At the end of the study, organs are harvested and analyzed for the presence of the API and metabolic products of the API. The pharmacokinetic properties of the API subjected to stability and/or stress testing are compared to API not subjected to stability or stress testing and other appropriate controls (e.g., vehicle control). Changes in pharmacokinetic properties as a result of stability and/or stress testing are determined.

(v) Pharmacodynamic Assays

Pharmacodynamics includes the study of the biochemical and physiological effects of drugs on the body or on microorganisms or parasites within or on the body and the mechanisms of drug action and the relationship between drug concentration and effect. Due to the complex nature of many disease states and the actions of many API, the API should be tested in vivo to confirm the desired activity of the agent. Mouse models for a large variety of disease states are known and commercially available (see, e.g., jaxmice.jax-.org/query/f?p=205:1:989373419139701::::P1_ADV:1). A number of induced models of disease are also known. Agents can be tested on the appropriate animal model to demonstrate stability and efficacy of the API on modulating the disease state.

(vi) Specific Immune Response Assay

Vaccines produce complex immune responses that are best assessed in vivo. The specific potency assay for a vaccine depends, at least in part, on the specific vaccine type. The most accurate predictions are based on mathematical modeling of biologically relevant stability-indicating parameters. For complex vaccines, e.g., whole cell vaccines, whole virus vaccines, complex mixtures of antigens, characterization of each component biochemically may be difficult, if not impossible. For example, when using a live, attenuated virus vaccine, the number of plaque forming units (e.g., mumps, measles, rubella, smallpox) or colony forming units (e.g., S. typhi, TY21a) are determined to confirm potency after storage. Chemical and physical characterization (e.g., polysaccharide and polysaccharide-protein conjugate vaccines) is performed to confirm the stability and activity of the vaccine. Serological response in animals to inactivated toxins and/or animal protection against challenge (e.g., rabies, anthrax, diphtheria, tetanus) is performed to confirm activity of vaccines of any type, particularly when the activity of the antigen has been inactivated. In vivo testing of vaccines subjected to stability and/or stress testing is performed by administering the vaccine to a subject using the appropriate immunization protocol for the vaccine, and determining the immune response by detection of specific immune cells that respond to stimulation with the antigen or pathogen, detection of antibodies against the antigen or pathogen, or protection in an immune challenge. Such methods are well known in the art. Vaccines include, but are not limited to, meningococcal B vaccine, hepatitis A and B vaccines, human papillomavirus vaccine, influenza vaccine, herpes zoster vaccine, and pneumococcal vaccine.

(vii) Toxicity Assays

Degradation of API can result in the formation of toxic agents. Toxicity assays include the administration of doses, typically far higher than would be used for therapeutic applications, to detect the presence of toxic products in the API. Toxicity assays can be performed in vitro and in vivo and are frequently single, high dose experiments. After administration of the compound, in addition to viability, organs are harvested and analyzed for any indication of toxicity, especially organs involved with clearance of API, e.g., liver, kidneys, and those for which damage could be catastrophic, e.g., heart, brain. The toxicologic properties of the API subjected to stability and/or stress testing are compared to API not subjected to stability or stress testing and other appropriate controls (e.g., vehicle control). Changes in toxicologic properties as a result of stability and/or stress testing are determined.

B. Small Molecules

In accordance with present invention, the degradation, alteration or depletion of small molecules contained within a delamination resistant pharmaceutical container of the present invention can be assessed by a variety of techniques. Indeed, in various aspects of the invention, the stability of a small molecule, degradation caused by the intetaction of a small molecule with the container or delaminants thereof, or changes in concentration or amount of the small molecule in a container can be assessed using techniques as follows. Such methods include, e.g., X-Ray Diffraction (XRPD), Thermal Analysis (such as Differential Scanning calorimetry (DSC), Thermogravimetry (TG) and Hot-Stage Microscopy (HSM), chromatography methods (such as High-Performance Liquid Chromatography (HPLC), Column Chromatography (CC), Gas Chromatography (GC), Thin-Layer Chromatography (TLC), and Super Critical Phase Chromatograph (SFC)), Mass Spectroscopy (MS), Capillary Electrophoresis (CE), Atomic Spectroscopy (AS), vibrational spectroscopy (such as Infrared Spectroscopy (IR)), Luminescence Spectroscopy (LS), and Nuclear Magnetic Resonance Spectroscopy (NMR).

In the case of pharmaceutical formulations where the API is not in solution or needs to be reconstituted into a different medium, XRPD may be a method for analyzing degradation. In ideal cases, every possible crystalline orientation is represented equally in a non-liquid sample.

Powder diffraction data is usually presented as a diffractogram in which the diffracted intensity I is shown as a function either of the scattering angle 20 or as a function of the scattering vector q. The latter variable has the advantage that the diffractogram no longer depends on the value of the wavelength 2. Relative to other methods of analysis, powder diffraction allows for rapid, non-destructive analysis of multi-component mixtures without the need for extensive sample preparation. Deteriorations of an API may be analyzed using this method, e.g., by comparing the diffraction pattern of the API to a known standard of the API prior to packaging.

Thermal methods of analysis may include, e.g., differential scanning calorimetry (DSC), thermogravimetry (TG), and hot-stage microscopy (HSM). All three methods provide information upon heating the sample. Depending on the information required, heating can be static or dynamic in nature.

Differential scanning calorimetry monitors the energy required to maintain the sample and a reference at the same temperature as they are heated. A plot of heat flow (W/g or J/g) versus temperature is obtained. The area under a DSC peak is directly proportional to the heat absorbed or released and integration of the peak results in the heat of transition.

Thermogravimetry (TG) measures the weight change of a sample as a function of temperature. A total volatile content of the sample is obtained, but no information on the identity of the evolved gas is provided. The evolved gas must be identified by other methods, such as gas chromatography, Karl Fisher titration (specifically to measure water), TG-mass spectroscopy, or TG-infrared spectroscopy. The temperature of the volatilization and the presence of steps in the TG curve can provide information on how tightly water or solvent is held in the lattice. If the temperature of the TG volatilization is similar to an endothermic peak in the DSC, the DSC peak is likely due or partially due to volatilization. It may be necessary to utilize multiple techniques to determine if more than one thermal event is responsible for a given DSC peak.

Hot-Stage Microscopy (HSM) is a technique that supplements DSC and TG. Events observed by DSC and/or TG can be readily characterized by HSM. Melting, gas evolution, and solid-solid transformations can be visualized, providing the most straightforward means of identifying thermal events. Thermal analysis can be used to determine the melting points, recrystallizations, solid-state transformations, decompositions, and volatile contents of pharmaceutical materials.

Other methods to analyze degradation or alteration of API and excipients are infrared (IR) and Raman spectroscopy. These techniques are sensitive to the structure, conformation, and environment of organic compounds. Infrared spectroscopy is based on the conversion of IR radiation into molecular vibrations. For a vibration to be IR-active, it must involve a changing molecular dipole (asymmetric mode). For example, vibration of a dipolar carbonyl group is detectable by IR spectroscopy. Whereas IR has been traditionally used as an aid in structure elucidation, vibrational changes also serve as probes of intermolecular interactions in solid materials.

Raman spectroscopy is based on the inelastic scattering of laser radiation with loss of vibrational energy by a sample. A vibrational mode is Raman active when there is a change in the polarizability during the vibration. Symmetric modes tend to be Raman-active. For example, vibrations about bonds between the same atom, such as in alkynes, can be observed by Raman spectroscopy.

NMR spectroscopy probes atomic environments based on the different resonance frequencies exhibited by nuclei in a strong magnetic field. Many different nuclei are observable by the NMR technique, but those of hydrogen and carbon atoms are most frequently studied. Solid-state NMR measurements are extremely useful for characterizing the crystal forms of pharmaceutical solids. Nuclei that are typically analyzed with this technique include those of 13C, 31P, 15N, 25Mg, and 23Na.

Chromatography is a general term applied to a wide variety of separation techniques based on the sample partitioning between a moving phase, which can be a gas, liquid, or supercritical fluid, and a stationary phase, which may be either a liquid or a solid. Generally, the crux of chromatography lies in the highly selective chemical interactions that occur in both the mobile and stationary phases. For example, depending on the API and the separation required, one or more of absorption, ion-exchange, size-exclusion, bonded phase, reverse, or normal phase stationary phases may be employed.

Mass spectrometry (MS) is an analytical technique that works by ionizing chemical compounds to generate charged molecules or molecule fragments and measuring their mass-to-charge ratios. Based on this analysis method, one can determine, e.g., the isotopic composition of elements in an API and determine the structure of the API by observing its fragmentation pattern.

It would be understood that the foregoing methods do not represent a comprehensive list of means by which one can analyze possible deteriorations, alterations, or concentrations of certain APIs. Therefore, it would be understood that other methods for determining the physical amounts and/or characteristics of an API may be employed. Additional methods may include, but are not limited to, e.g., Capillary Electrophoresis (CE), Atomic Spectroscopy (AS), and Luminescence Spectroscopy (LS).

EXAMPLES

The embodiments of the delamination resistant pharmaceutical containers described herein will be further clarified by the following examples.

Example 1

Six exemplary inventive glass compositions (compositions A-F) were prepared. The specific compositions of each exemplary glass composition are reported below in Table 8. Multiple samples of each exemplary glass composition were produced. One set of samples of each composition was ion exchanged in a molten salt bath of 100% $KNO_3$ at a temperature of 450° C. for at least 5 hours to induce a compressive layer in the surface of the sample. The compressive layer had a surface compressive stress of at least 500 MPa and a depth of layer of at least 45 μm.

The chemical durability of each exemplary glass composition was then determined utilizing the DIN 12116 standard, the ISO 695 standard, and the ISO 720 standard described above. Specifically, non-ion exchanged test samples of each exemplary glass composition were subjected to testing according to one of the DIN 12116 standard, the ISO 695 standard, or the ISO 720 standard to determine the acid resistance, the base resistance or the hydrolytic resistance of the test sample, respectively. The hydrolytic resistance of the ion exchanged samples of each exemplary composition was determined according to the ISO 720 standard. The average results of all samples tested are reported below in Table 8.

As shown in Table 8, exemplary glass compositions A-F all demonstrated a glass mass loss of less than 5 mg/dm² and greater than 1 mg/dm² following testing according to the DIN 12116 standard with exemplary glass composition E having the lowest glass mass loss at 1.2 mg/dm². Accordingly, each of the exemplary glass compositions were classified in at least class S3 of the DIN 12116 standard, with exemplary glass composition E classified in class S2. Based on these test results, it is believed that the acid resistance of the glass samples improves with increased $SiO_2$ content.

Further, exemplary glass compositions A-F all demonstrated a glass mass loss of less than 80 mg/dm² following testing according to the ISO 695 standard with exemplary glass composition A having the lowest glass mass loss at 60 mg/dm². Accordingly, each of the exemplary glass compositions were classified in at least class A2 of the ISO 695 standard, with exemplary glass compositions A, B, D and F classified in class A1. In general, compositions with higher silica content exhibited lower base resistance and compositions with higher alkali/alkaline earth content exhibited greater base resistance.

Table 8 also shows that the non-ion exchanged test samples of exemplary glass compositions A-F all demonstrated a hydrolytic resistance of at least Type HGA2 following testing according to the ISO 720 standard with exemplary glass compositions C-F having a hydrolytic resistance of Type HGA1. The hydrolytic resistance of exemplary glass compositions C-F is believed to be due to higher amounts of $SiO_2$ and the lower amounts of $Na_2O$ in the glass compositions relative to exemplary glass compositions A and B.

Moreover, the ion exchanged test samples of exemplary glass compositions B-F demonstrated lower amounts of extracted $Na_2O$ per gram of glass than the non-ion exchanged test samples of the same exemplary glass compositions following testing according to the ISO 720 standard.

TABLE 1

Composition and Properties of Exemplary Glass Compositions

| | Composition in mole % | | | | | |
|---|---|---|---|---|---|---|
| | A | B | C | D | E | F |
| $SiO_2$ | 70.8 | 72.8 | 74.8 | 76.8 | 76.8 | 77.4 |
| $Al_2O_3$ | 7.5 | 7 | 6.5 | 6 | 6 | 7 |
| $Na_2O$ | 13.7 | 12.7 | 11.7 | 10.7 | 11.6 | 10 |
| $K_2O$ | 1 | 1 | 1 | 1 | 0.1 | 0.1 |
| MgO | 6.3 | 5.8 | 5.3 | 4.8 | 4.8 | 4.8 |
| CaO | 0.5 | 0.5 | 0.5 | 0.5 | 0.5 | 0.5 |
| $SnO_2$ | 0.2 | 0.2 | 0.2 | 0.2 | 0.2 | 0.2 |
| DIN 12116 (mg/dm²) | 3.2 | 2.0 | 1.7 | 1.6 | 1.2 | 1.7 |
| classification | S3 | S3 | S3 | S3 | S2 | S3 |
| ISO 695 (mg/dm²) | 60.7 | 65.4 | 77.9 | 71.5 | 76.5 | 62.4 |
| classification | A1 | A1 | A2 | A1 | A2 | A1 |
| ISO 720 (ug $Na_2O$/g glass) | 100.7 | 87.0 | 54.8 | 57.5 | 50.7 | 37.7 |
| classification | HGA2 | HGA2 | HGA1 | HGA1 | HGA1 | HGA1 |
| ISO 720 (with IX) (ug $Na_2O$/g glass) | 60.3 | 51.9 | 39.0 | 30.1 | 32.9 | 23.3 |
| classification | HGA1 | HGA1 | HGA1 | HGA1 | HGA1 | HGA1 |

Example 2

Three exemplary inventive glass compositions (compositions G-I) and three comparative glass compositions (compositions 1-3) were prepared. The ratio of alkali oxides to alumina (i.e., Y:X) was varied in each of the compositions in order to assess the effect of this ratio on various properties of the resultant glass melt and glass. The specific compositions of each of the exemplary inventive glass compositions and the comparative glass compositions are reported in Table 9. The strain point, anneal point, and softening point of melts formed from each of the glass compositions were determined and are reported in Table 2. In addition, the coefficient of thermal expansion (CTE), density, and stress optic coefficient (SOC) of the resultant glasses were also determined and are reported in Table 9. The hydrolytic resistance of glass samples formed from each exemplary inventive glass composition and each comparative glass composition was determined according to the ISO 720 Standard both before ion exchange and after ion exchange in a molten salt bath of 100% $KNO_3$ at 450° C. for 5 hours. For those samples that were ion exchanged, the compressive stress was determined with a fundamental stress meter (FSM) instrument, with the compressive stress value based on the measured stress optical coefficient (SOC). The FSM instrument couples light into and out of the birefringent glass surface. The measured birefringence is then related to stress through a material constant, the stress-optic or photoelastic coefficient (SOC or PEC) and two parameters are obtained: the maximum surface compressive stress (CS) and the exchanged depth of layer (DOL). The diffusivity of the alkali ions in the glass and the change in stress per square root of time were also determined.

Figure 2:
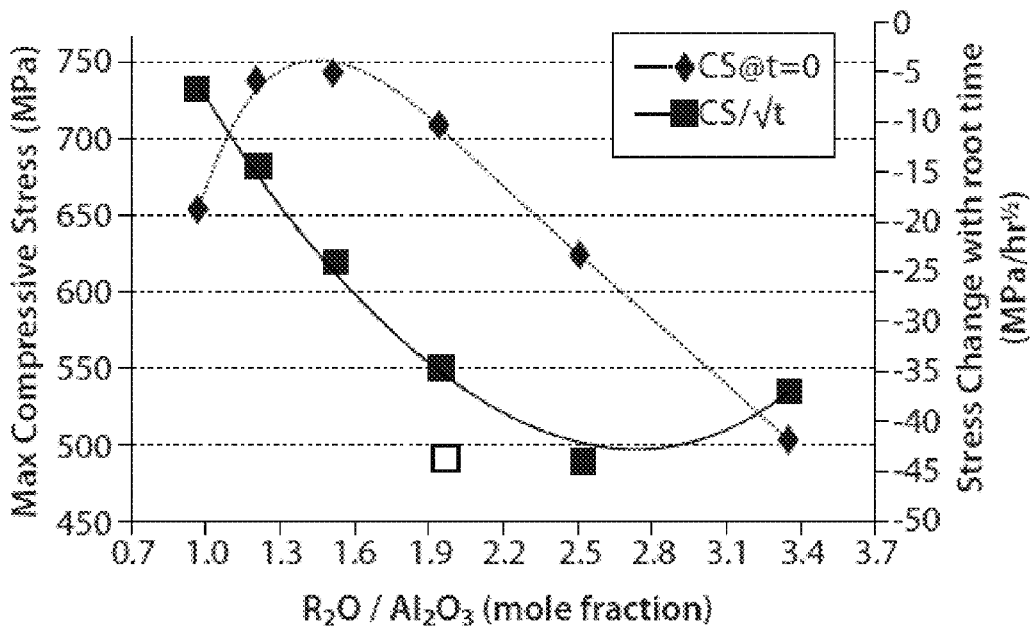
FIG. 2 graphically depicts the relationship between the ratio of alkali oxides to alumina (x-axis) and the maximum compressive stress and stress change (y-axes) of inventive and comparative glass compositions.

Moreover, FIG. 2 indicates that for a given ion exchange time and ion exchange temperature, the maximum compressive stresses are obtained when the ratio of Y:X is greater than or equal to about 0.9, or even greater than or equal to about 1, and less than or equal to about 2, specifically greater than or equal to about 1.3 and less than or equal to about 2.0. Accordingly, the maximum improvement in the load bearing strength of the glass can be obtained when the ratio of Y:X is greater than about 1 and less than or equal to about 2. It is generally understood that the maximum stress achievable by ion exchange will decay with increasing ion-exchange duration as indicated by the stress change rate (i.e., the measured compressive stress divided by the square root of the ion exchange time). FIG. 2 generally shows that the stress change rate decreases as the ratio Y:X decreases.

Figure 3:
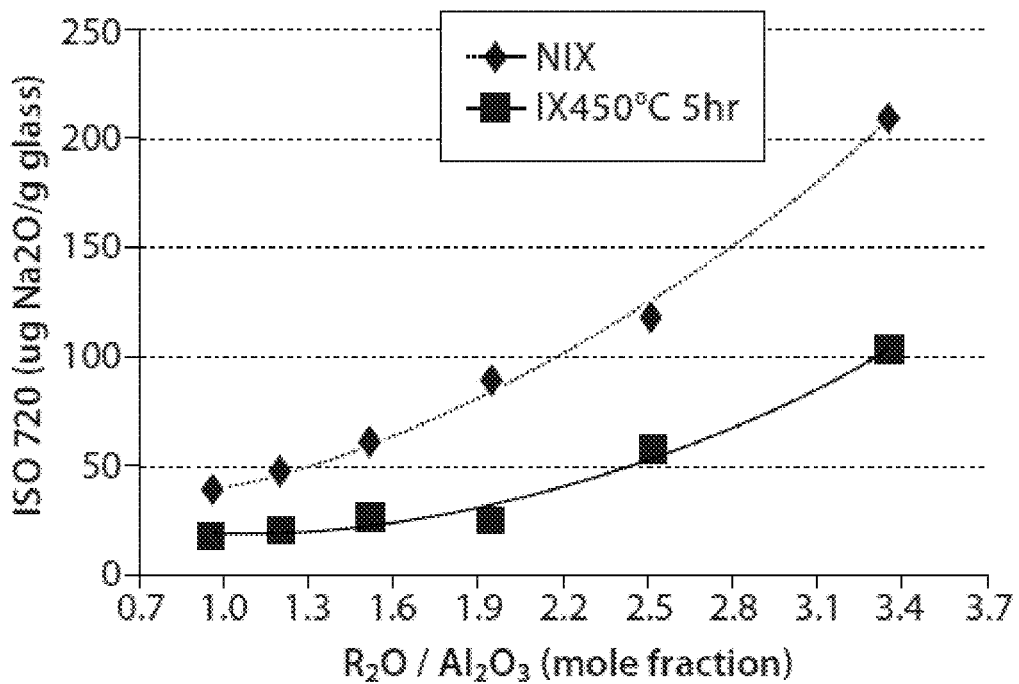
FIG. 3 graphically depicts the relationship between the ratio of alkali oxides to alumina (x-axis) and hydrolytic resistance as determined from the ISO 720 standard (y-axis) of inventive and comparative glass compositions.

FIG. 3 graphically depicts the hydrolytic resistance (y-axis) as a function of the ratio Y:X (x-axis). As shown in FIG. 3, the hydrolytic resistance of the glasses generally improves as the ratio Y:X decreases.

Based on the foregoing it should be understood that glasses with good melt behavior, superior ion exchange performance, and superior hydrolytic resistance can be achieved by maintaining the ratio Y:X in the glass from

TABLE 9

Glass properties as a function of alkali to alumina ratio
Composition Mole %

| | G | H | I | 1 | 2 | 3 |
|---|---|---|---|---|---|---|
| $SiO_2$ | 76.965 | 76.852 | 76.962 | 76.919 | 76.960 | 77.156 |
| $Al_2O_3$ | 5.943 | 6.974 | 7.958 | 8.950 | 4.977 | 3.997 |
| $Na_2O$ | 11.427 | 10.473 | 9.451 | 8.468 | 12.393 | 13.277 |
| $K_2O$ | 0.101 | 0.100 | 0.102 | 0.105 | 0.100 | 0.100 |
| MgO | 4.842 | 4.878 | 4.802 | 4.836 | 4.852 | 4.757 |
| CaO | 0.474 | 0.478 | 0.481 | 0.480 | 0.468 | 0.462 |
| $SnO_2$ | 0.198 | 0.195 | 0.197 | 0.197 | 0.196 | 0.196 |
| Strain (° C.) | 578 | 616 | 654 | 683 | 548 | 518 |
| Anneal (° C.) | 633 | 674 | 716 | 745 | 600 | 567 |
| Softening (° C.) | 892 | 946 | 1003 | 1042 | 846 | 798 |
| Expansion ($10^{-7}$ $K^{-1}$) | 67.3 | 64.3 | 59.3 | 55.1 | 71.8 | 74.6 |
| Density (g/$cm^3$) | 2.388 | 2.384 | 2.381 | 2.382 | 2.392 | 2.396 |
| SOC (nm/mm/Mpa) | 3.127 | 3.181 | 3.195 | 3.232 | 3.066 | 3.038 |
| ISO720 (non-IX) | 88.4 | 60.9 | 47.3 | 38.4 | 117.1 | 208.1 |
| ISO720 (IX450° C.-5 hr) | 25.3 | 26 | 20.5 | 17.8 | 57.5 | 102.5 |
| $R_2O/Al_2O_3$ | 1.940 | 1.516 | 1.200 | 0.958 | 2.510 | 3.347 |
| CS@t = 0 (MPa) | 708 | 743 | 738 | 655 | 623 | 502 |
| CS/√t (MPa/$hr^{1/2}$) | −35 | −24 | −14 | −7 | −44 | −37 |
| D ($\mu m^2$/hr) | 52.0 | 53.2 | 50.3 | 45.1 | 51.1 | 52.4 |

The data in Table 9 indicates that the alkali to alumina ratio Y:X influences the melting behavior, hydrolytic resistance, and the compressive stress obtainable through ion exchange strengthening. In particular, FIG. 1 graphically depicts the strain point, anneal point, and softening point as a function of Y:X ratio for the glass compositions of Table 9. FIG. 1 demonstrates that, as the ratio of Y:X decreases below 0.9, the strain point, anneal point, and softening point of the glass rapidly increase. Accordingly, to obtain a glass which is readily meltable and formable, the ratio Y:X should be greater than or equal to 0.9 or even greater than or equal to 1.

Further, the data in Table 2 indicates that the diffusivity of the glass compositions generally decreases with the ratio of Y:X. Accordingly, to achieve glasses can be rapidly ion exchanged in order to reduce process times (and costs) the ratio of Y:X should be greater than or equal to 0.9 or even greater than or equal to 1.

greater than or equal to about 0.9, or even greater than or equal to about 1, and less than or equal to about 2.

Example 3

Three exemplary inventive glass compositions (compositions J-L) and three comparative glass compositions (compositions 4-6) were prepared. The concentration of MgO and CaO in the glass compositions was varied to produce both MgO-rich compositions (i.e., compositions J-L and 4) and CaO-rich compositions (i.e., compositions 5-6). The relative amounts of MgO and CaO were also varied such that the glass compositions had different values for the ratio (CaO/(CaO+MgO)). The specific compositions of each of the exemplary inventive glass compositions and the comparative glass compositions are reported below in Table 10. The properties of each composition were determined as described above with respect to Example 2.

TABLE 10

Glass properties as function of CaO content
Composition Mole %

| | J | K | L | 4 | 5 | 6 |
|---|---|---|---|---|---|---|
| $SiO_2$ | 76.99 | 77.10 | 77.10 | 77.01 | 76.97 | 77.12 |
| $Al_2O_3$ | 5.98 | 5.97 | 5.96 | 5.96 | 5.97 | 5.98 |
| $Na_2O$ | 11.38 | 11.33 | 11.37 | 11.38 | 11.40 | 11.34 |
| $K_2O$ | 0.10 | 0.10 | 0.10 | 0.10 | 0.10 | 0.10 |
| MgO | 5.23 | 4.79 | 3.78 | 2.83 | 1.84 | 0.09 |
| CaO | 0.07 | 0.45 | 1.45 | 2.46 | 3.47 | 5.12 |
| $SnO_2$ | 0.20 | 0.19 | 0.19 | 0.19 | 0.19 | 0.19 |
| Strain (° C.) | 585 | 579 | 568 | 562 | 566 | 561 |
| Anneal (° C.) | 641 | 634 | 620 | 612 | 611 | 610 |
| Softening (° C.) | 902 | 895 | 872 | 859 | 847 | 834 |
| Expansion ($10^{-7}$ $K^{-1}$) | 67.9 | 67.1 | 68.1 | 68.8 | 69.4 | 70.1 |
| Density (g/$cm^3$) | 2.384 | 2.387 | 2.394 | 2.402 | 2.41 | 2.42 |
| SOC nm/mm/Mpa | 3.12 | 3.08 | 3.04 | 3.06 | 3.04 | 3.01 |
| ISO720 (non-IX) | 83.2 | 83.9 | 86 | 86 | 88.7 | 96.9 |
| ISO720 (IX450° C.-5 hr) | 29.1 | | 28.4 | 33.2 | 37.3 | 40.1 |
| Fraction of RO as CaO | 0.014 | 0.086 | 0.277 | 0.465 | 0.654 | 0.982 |
| CS@t = 0 (MPa) | 707 | 717 | 713 | 689 | 693 | 676 |
| CS/√t (MPa/$hr^{1/2}$) | −36 | −37 | −39 | −38 | −43 | −44 |
| D ($\mu m^2$/hr) | 57.2 | 50.8 | 40.2 | 31.4 | 26.4 | 20.7 |

Figure 4:
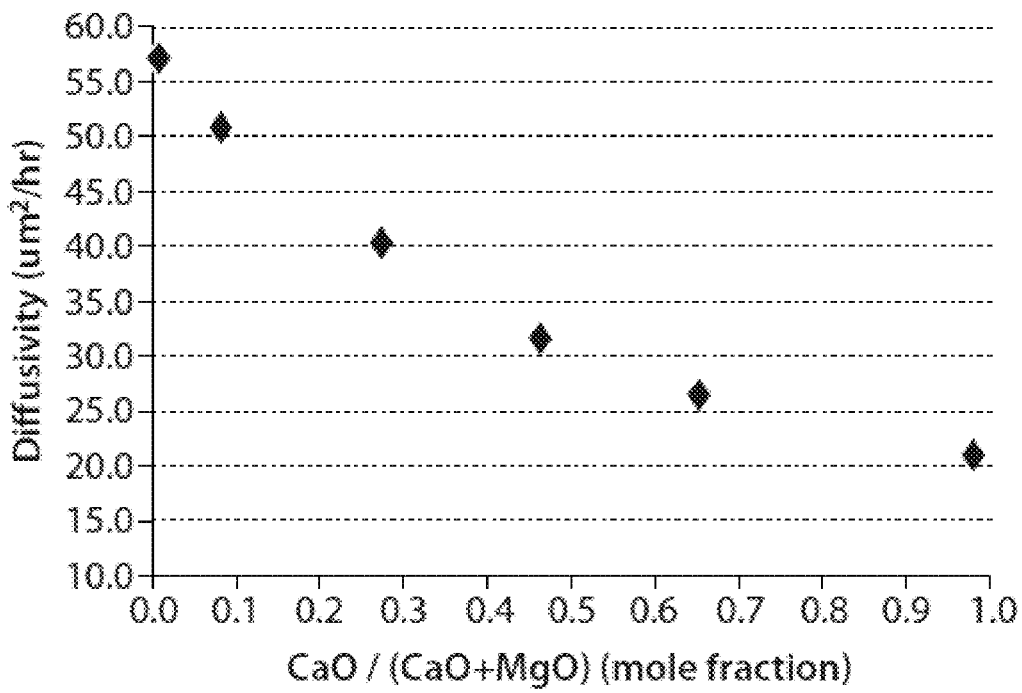
FIG. 4 graphically depicts diffusivity D (y-axis) as a function of the ratio (CaO/(CaO+MgO)) (x-axis) for inventive and comparative glass compositions.
Figure 5:
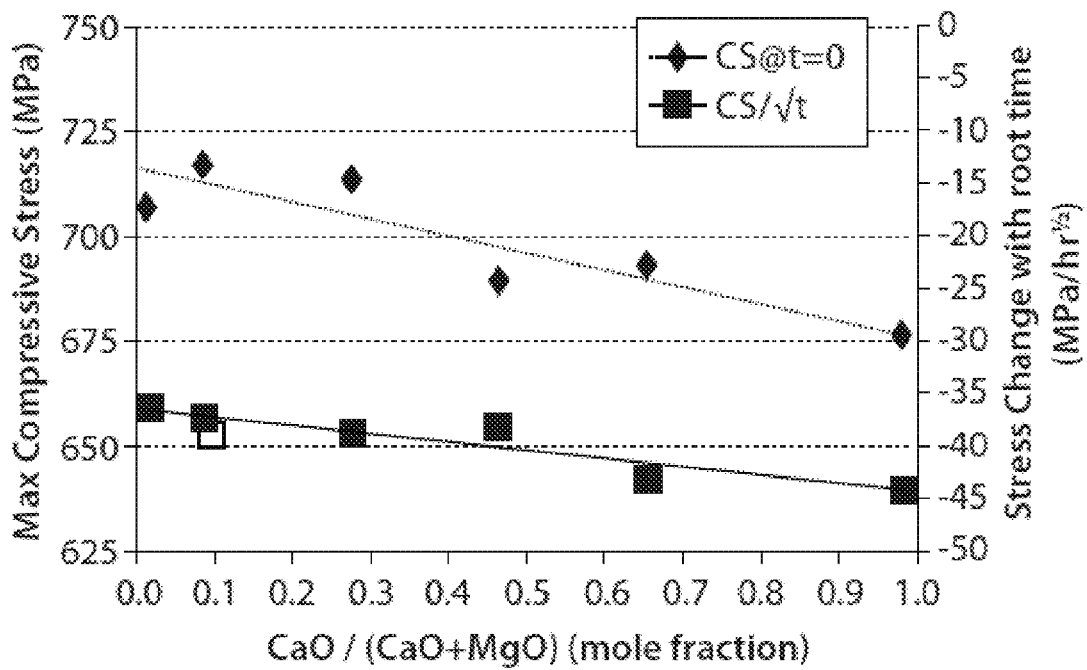
FIG. 5 graphically depicts the maximum compressive stress (y-axis) as a function of the ratio (CaO/(CaO+MgO)) (x-axis) for inventive and comparative glass compositions.

FIG. 4 graphically depicts the diffusivity D of the compositions listed in Table 10 as a function of the ratio (CaO/(CaO+MgO)). Specifically, FIG. 4 indicates that as the ratio (CaO/(CaO+MgO)) increases, the diffusivity of alkali ions in the resultant glass decreases thereby diminishing the ion exchange performance of the glass. This trend is supported by the data in Table 10 and FIG. 5. FIG. 5 graphically depicts the maximum compressive stress and stress change rate (y-axes) as a function of the ratio (CaO/(CaO+MgO)). FIG. 5 indicates that as the ratio (CaO/(CaO+MgO)) increases, the maximum obtainable compressive stress decreases for a given ion exchange temperature and ion exchange time. FIG. 5 also indicates that as the ratio (CaO/(CaO+MgO)) increases, the stress change rate increases (i.e., becomes more negative and less desirable).

Accordingly, based on the data in Table 10 and FIGS. 4 and 5, it should be understood that glasses with higher diffusivities can be produced by minimizing the ratio (CaO/(CaO+MgO)). It has been determined that glasses with suitable diffusivities can be produced when the (CaO/(CaO+MgO)) ratio is less than about 0.5. The diffusivity values of the glass when the (CaO/(CaO+MgO)) ratio is less than about 0.5 decreases the ion exchange process times needed to achieve a given compressive stress and depth of layer.

Alternatively, glasses with higher diffusivities due to the ratio (CaO/(CaO+MgO)) may be used to achieve a higher compressive stress and depth of layer for a given ion exchange temperature and ion exchange time.

Moreover, the data in Table 10 also indicates that decreasing the ratio (CaO/(CaO+MgO)) by increasing the MgO concentration generally improves the resistance of the glass to hydrolytic degradation as measured by the ISO 720 standard.

Example 4

Three exemplary inventive glass compositions (compositions M-O) and three comparative glass compositions (compositions 7-9) were prepared. The concentration of $B_2O_3$ in the glass compositions was varied from 0 mol. % to about 4.6 mol. % such that the resultant glasses had different values for the ratio $B_2O_3/(R_2O—Al_2O_3)$. The specific compositions of each of the exemplary inventive glass compositions and the comparative glass compositions are reported below in Table 11. The properties of each glass composition were determined as described above with respect to Examples 2 and 3.

TABLE 11

Glass properties as a function of $B_2O_3$ content
Composition Mole %

| | M | N | O | 7 | 8 | 9 |
|---|---|---|---|---|---|---|
| $SiO_2$ | 76.860 | 76.778 | 76.396 | 74.780 | 73.843 | 72.782 |
| $Al_2O_3$ | 5.964 | 5.948 | 5.919 | 5.793 | 5.720 | 5.867 |
| $B_2O_3$ | 0.000 | 0.214 | 0.777 | 2.840 | 4.443 | 4.636 |
| $Na_2O$ | 11.486 | 11.408 | 11.294 | 11.036 | 10.580 | 11.099 |
| $K_2O$ | 0.101 | 0.100 | 0.100 | 0.098 | 0.088 | 0.098 |
| MgO | 4.849 | 4.827 | 4.801 | 4.754 | 4.645 | 4.817 |
| CaO | 0.492 | 0.480 | 0.475 | 0.463 | 0.453 | 0.465 |
| $SnO_2$ | 0.197 | 0.192 | 0.192 | 0.188 | 0.183 | 0.189 |
| Strain (° C.) | 579 | 575 | 572 | 560 | 552 | 548 |
| Anneal (° C.) | 632 | 626 | 622 | 606 | 597 | 590 |
| Softening (° C.) | 889 | 880 | 873 | 836 | 816 | 801 |
| Expansion ($10^{-7}$ $K^{-1}$) | 68.3 | 67.4 | 67.4 | 65.8 | 64.1 | 67.3 |
| Density (g/$cm^3$) | 2.388 | 2.389 | 2.390 | 2.394 | 2.392 | 2.403 |
| SOC (nm/mm/MPa) | 3.13 | 3.12 | 3.13 | 3.17 | 3.21 | 3.18 |

TABLE 11-continued

Glass properties as a function of $B_2O_3$ content
Composition Mole %

| | M | N | O | 7 | 8 | 9 |
|---|---|---|---|---|---|---|
| ISO720 (non-IX) | 86.3 | 78.8 | 68.5 | 64.4 | 52.7 | 54.1 |
| ISO720 (IX450° C.-5 hr) | 32.2 | 30.1 | 26 | 24.7 | 22.6 | 26.7 |
| $B_2O_3/(R_2O\text{—}Al_2O_3)$ | 0.000 | 0.038 | 0.142 | 0.532 | 0.898 | 0.870 |
| CS@t = 0 (MPa) | 703 | 714 | 722 | 701 | 686 | 734 |
| CS/√t (MPa/hr$^{1/2}$) | −38 | −38 | −38 | −33 | −32 | −39 |
| D (µm$^2$/hr) | 51.7 | 43.8 | 38.6 | 22.9 | 16.6 | 15.6 |

Figure 6:
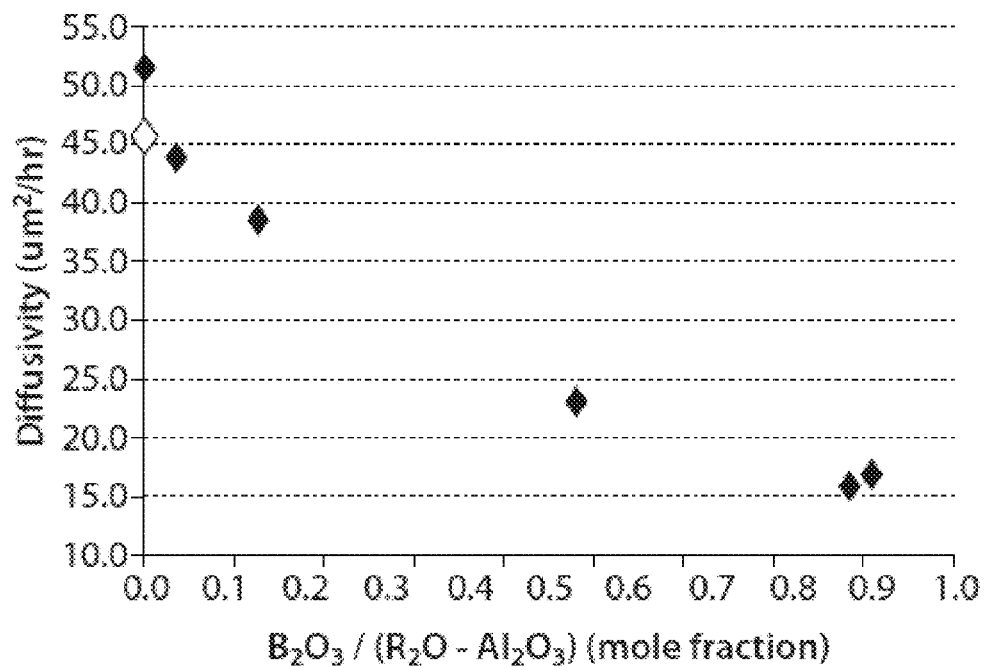
FIG. 6 graphically depicts diffusivity D (y-axis) as a function of the ratio ($B_2O_3$/($R_2O$—$Al_2O_3$)) (x-axis) for inventive and comparative glass compositions.

FIG. 6 graphically depicts the diffusivity D (y-axis) of the glass compositions in Table 11 as a function of the ratio $B_2O_3/(R_2O\text{—}Al_2O_3)$ (x-axis) for the glass compositions of Table 11. As shown in FIG. 6, the diffusivity of alkali ions in the glass generally decreases as the ratio $B_2O_3/(R_2O\text{—}Al_2O_3)$ increases.

Figure 7:
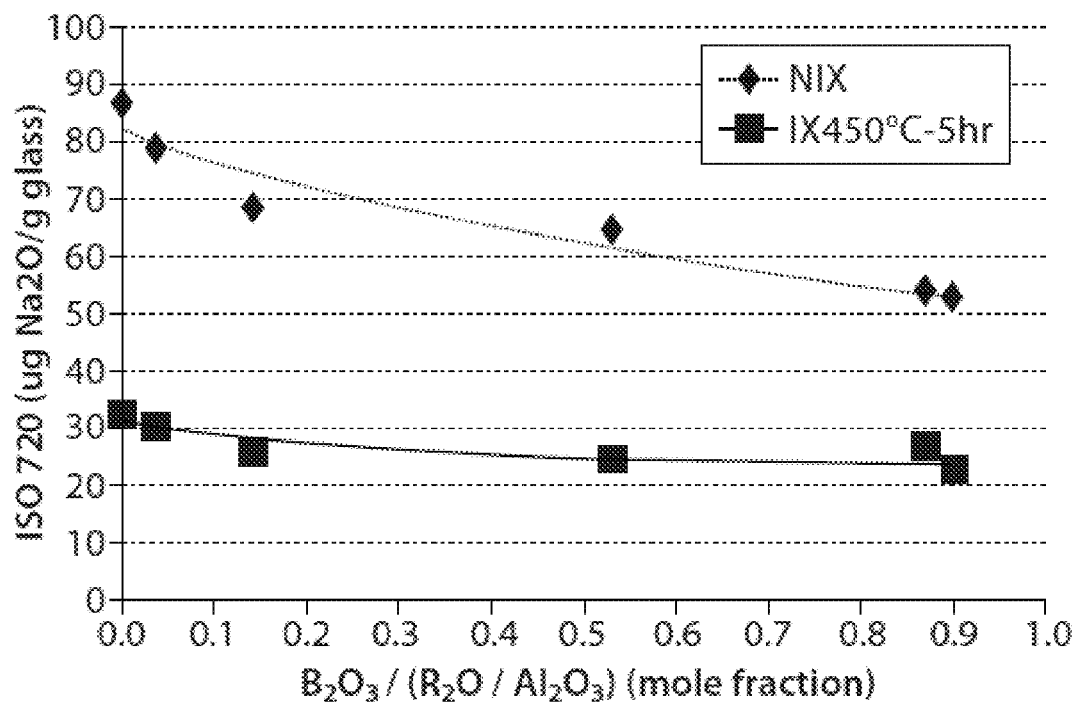
FIG. 7 graphically depicts the hydrolytic resistance as determined from the ISO 720 standard (y-axis) as a function of the ratio ($B_2O_3$/($R_2O$—$Al_2O_3$)) (x-axis) for inventive and comparative glass compositions.

FIG. 7 graphically depicts the hydrolytic resistance according to the ISO 720 standard (y-axis) as a function of the ratio $B_2O_3/(R_2O\text{—}Al_2O_3)$ (x-axis) for the glass compositions of Table 11. As shown in FIG. 6, the hydrolytic resistance of the glass compositions generally improves as the ratio $B_2O_3/(R_2O\text{—}Al_2O_3)$ increases.

Based on FIGS. 6 and 7, it should be understood that minimizing the ratio $B_2O_3/(R_2O\text{—}Al_2O_3)$ improves the diffusivity of alkali ions in the glass thereby improving the ion exchange characteristics of the glass. Further, increasing the ratio $B_2O_3/(R_2O\text{—}Al_2O_3)$ also generally improves the resistance of the glass to hydrolytic degradation. In addition, it has been found that the resistance of the glass to degradation in acidic solutions (as measured by the DIN 12116 standard) generally improves with decreasing concentrations of $B_2O_3$. Accordingly, it has been determined that maintaining the ratio $B_2O_3/(R_2O\text{—}Al_2O_3)$ to less than or equal to about 0.3 provides the glass with improved hydrolytic and acid resistances as well as providing for improved ion exchange characteristics.

It should now be understood that the glass compositions described herein exhibit chemical durability as well as mechanical durability following ion exchange. These properties make the glass compositions well suited for use in various applications including, without limitation, pharmaceutical packaging materials.

Example 5

Determining the Presence and Amount of Glass Flakes in Pharmaceutical Solutions

The resistance to delamination may be characterized by the number of glass particulates present in a pharmaceutical solution contained within a glass container described herein after. In order to assess the long-term resistance of the glass container to delamination, an accelerated delamination test is utilized. The test consists of washing the glass container at room temperature for 1 minute and depyrogenating the container at about 320° C. for 1 hour. Thereafter a pharmaceutical solution is placed in the glass container to 80-90% full, the glass container is closed, and rapidly heated to, for example, 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the pharmaceutical solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm X 1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers.

It should be understood that the aforementioned test is used to identify particles which are shed from the interior wall(s) of the glass container due to delamination and not tramp particles present in the container from forming processes. Specifically, delamination particles will be differentiated from tramp glass particles based on the aspect ratio of the particle (i.e., the ratio of the width of the particle to the thickness of the particle). Delamination produces particulate flakes or lamellae which are irregularly shaped and are typically >50 µm in diameter but often >200 µm. The thickness of the flakes is usually greater than about 100 nm and may be as large as about 1 µm. Thus, the minimum aspect ratio of the flakes is typically >50. The aspect ratio may be greater than 100 and sometimes greater than 1000.

Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

Using this method, pharmaceutical compositions can be tested for the presence of glass flakes and various compositions can be compared to each other to assess the safety of various pharmaceutical compositions.

Example 6

Stability Testing of Pharmaceutical Compositions

Stability studies are part of the testing required by the FDA and other regulatory agencies. Stability studies should include testing of those attributes of the API that are susceptible to change during storage and are likely to influence quality, safety, and/or efficacy. The testing should cover, as appropriate, the physical, chemical, biological, and microbiological attributes of the API (e.g., small molecule or biologic therapeutic agent) in the container with the closure to be used for storage of the agent. If the API is formulated as a liquid by the manufacturer, the final formulation should be assayed for stability. If the API is formulated as an agent for reconstitution by the end user using a solution provided by the manufacturer, both the API and the solution for reconstitution are preferably tested for stability as the separate packaged components (e.g., the API subjected to storage reconstituted with solution for reconstitution not subject to storage, API not subject to storage reconstituted with a solution subject to storage, and both API and solution subject to storage). This is particularly the case when the solution for reconstitution includes an active agent (e.g., an adjuvant for reconstitution of a vaccine).

In general, a substance API should be evaluated under storage conditions (with appropriate tolerances) that test its thermal stability and, if applicable, its sensitivity to moisture. The storage conditions and the lengths of studies chosen should be sufficient to cover storage, shipment, and subsequent use.

API should be stored in the container(s) in which the API will be provided to the end user (e.g., vials, ampules, syringes, injectable devices). Stability testing methods provided herein refer to samples being removed from the storage or stress conditions indicated. Removal of a sample preferably refers to removing an entire container from the storage or stress conditions. Removal of a sample should not be understood as withdrawing a portion of the API from the container as removal of a portion of the API from the container would result in changes of fill volume, gas environment, etc. At the time of testing the API subject to stability and/or stress testing, portions of the samples subject to stability and/or stress testing can be used for individual assays.

The long-term testing should cover a minimum of 12 months' duration on at least three primary batches at the time of submission and should be continued for a period of time sufficient to cover the proposed retest period. Additional data accumulated during the assessment period of the registration application should be submitted to the authorities if requested. Data from the accelerated storage condition and, if appropriate, from the intermediate storage condition can be used to evaluate the effect of short-term excursions outside the label storage conditions (such as might occur during shipping).

Long-term, accelerated, and, where appropriate, intermediate storage conditions for API are detailed in the sections below. The general case should apply if the API is not specifically covered by a subsequent section. It is understood that the time points for analysis indicated in the table are suggested end points for analysis. Interim analysis can be preformed at shorter time points (e.g., 1, 2, 3, 4, 5, 6, 7, 8, 9, 10, or 11 months). For API to be labeled as stable for storage for more than 12 months, time points beyond 12 months can be assessed (e.g., 15, 18, 21, 24 months). Alternative storage conditions can be used if justified.

TABLE 12

General Conditions for Stability Analysis

| Study | Storage condition | Time points for analysis |
|---|---|---|
| Long-term | Long-term* 25° C. ± 2° C./ 60% RH ± 5% RH or 30° C. ± 2° C./65% RH ± 5% RH | 12 months |
| Intermediate | 30° C. ± 2° C./65% RH ± 5% RH | 6 months |
| Accelerated | 40° C. ± 2° C./75% RH ± 5% RH | 6 months |

TABLE 13

Conditions for Stability Analysis for Storage in a Refrigerator

| Study | Storage condition | Minimum time period covered by data at submission |
|---|---|---|
| Long-term | 5° C. ± 3° C. | 12 months |
| Accelerated | 25° C. ± 2° C./60% RH ± 5% RH | 6 months |

TABLE 14

Conditions for Stability Analysis for Storage in a Freezer

| Study | Storage condition | Minimum time period covered by data at submission |
|---|---|---|
| Long-term | −20° C. ± 5° C. | 12 months |

Storage condition for API intended to be stored in a freezer, testing on a single batch at an elevated temperature (e.g., 5° C.±3° C. or 25° C.±2° C.) for an appropriate time period should be conducted to address the effect of short-term excursions outside the proposed label storage condition (e.g., stress during shipping or handling, e.g., increased temperature, multiple freeze-thaw cycles, storage in a non-upright orientation, shaking, etc.).

The assays performed to assess stability of an API include assays to that are used across most APIs to assess the physical properties of the API, e.g., degradation, pH, color, particulate formation, concentration, toxicity, etc. Assays to detect the general properties of the API are also selected based on the chemical class of the agent, e.g., denaturation and aggregation of protein based API. Assays to detect the potency of the API, i.e., the ability of the API to achieve its intended effect as demonstrated by the quantitative measurement of an attribute indicative of the clinical effect as compared to an appropriate control, are selected based on the activity of the particular agent. For example, the biological activity of the API, e.g., enzyme inhibitor activity, cell killing activity, anti-inflammatory activity, coagulation modulating activity, etc., is measured using in vitro and/or in vivo assays such as those provided herein. Pharmacokinetic and toxicological properties of the API are also assessed using methods known in the art, such as those provided herein.

Example 7

Analysis of Adherence to Glass Vials

Changes in the surface of glass can result in changes in the adherence of API to glass. The amount of agent in samples withdrawn from glass vials are tested at intervals to determine if the concentration of the API in solution changes over time. API are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the concentration of the API in solution. The concentration of the API is determined using methods and controls appropriate to the API. The concentration of the API is preferably determined in conjunction with at least one assay to confirm that the API, rather than degradation products of the API, is detected. In the case of biologics in which the conformational structure of the biologic agent is essential to its function of the API, the assays for concentration of the biologic are preferably preformed in conjunction with an assay to confirm the structure of the biologic (e.g., activity assay).

For example, in the cases of small molecule APIs, the amount of agent present is determined, for example, by mass spectrometry, optionally in combination with liquid chromatography, as appropriate, to separate the agent from any degradation products that may be present in the sample.

For protein based biologic APIs, the concentration of the API is determined, for example, using ELISA assay. Chromatography methods are used in conjunction with methods to determine protein concentration to confirm that protein fragments or aggregates are not being detected by the ELISA assay.

For nucleic acid biologic APIs, the concentration of the API is determined, for example, using quantitative PCR when the nucleic acids are of sufficient length to permit detection by such methods. Chromatography methods are used to determine both the concentration and size of nucleic acid based API.

For viral vaccine APIs, the concentration of the virus is determined, for example, using colony formation assays.

Example 8

Analysis of Pharmacokinetic Properties

Pharmacokinetics is concerned with the analysis of absorption, distribution, metabolism, and excretion of API. Storage and stress can potentially affect the pharmacokinetic properties of various API. To assess pharmacokinetics of API subject to stability and/or stress testing, agents are incubated in containers as described in Example 6. Preferably, the API are incubated both in standard glass vials with appropriate closures and glass vials such as those provided herein. At the desired intervals, samples are removed and assayed.

The API is delivered to subjects by the typical route of delivery for the API (e.g., injection, oral, topical). As pharmacokinetics are concerned with the absorption and elimination of the API, normal subjects are typically used to assess pharmacokinetic properties of the API. However, if the API is to be used in subjects with compromised ability to absorb or eliminate the API (e.g., subjects with liver or kidney disease), testing in an appropriate disease model may be advantageous. Depending on the half life of the compound, samples (e.g., blood, urine, stool) are collected at predetermined time points (e.g., 0 min, 30 min, 60 min, 90 min, 120 min, 4 hours, 6 hours, 12 hours, 24 hours, 36 hours, 48 hours, etc.) for at least two, preferably three half-lives of the API, and analyzed for the presence of the API and metabolic products of the API. At the end of the study, organs are harvested and analyzed for the presence of the API and metabolic products of the API.

The results are analyzed using an appropriate model selected based on, at least, the route of administration of the API. The pharmacokinetic properties of the API subjected to stability and/or stress testing are compared to API not subjected to stability or stress testing and other appropriate controls (e.g., vehicle control). Changes, if any, in pharmacokinetic properties as a result of storage of the API under each condition are determined.

Example 9

Analysis of Toxicity Profiles

Storage of API can result in alterations of toxicity of API as a result of reactivity of the API with the container, leeching of agents from the container, delamination resulting in particulates in the agent, reaction of the API molecules with each other or components of the storage buffer, or other causes.

Agents are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the toxicity the API. The toxicity of the API is determined using methods and controls appropriate to the API. In vitro and in vivo testing can be used alone or in combination to assess changes in toxicity of agents as a result of storage or stress.

In in vitro assays, cell lines are grown in culture and contacted with increasing concentrations of API subjected to stability and/or stress testing for predetermined amounts of time (e.g., 12, 24, 36, 48, and 72 hours). Cell viability is assessed using any of a number of routine or commercially available assays. Cells are observed, for example, by microscopy or using fluorescence activated cell sorting (FACS) analysis using commercially available reagents and kits. For example, membrane-permeant calcein AM is cleaved by esterases in live cells to yield cytoplasmic green fluorescence, and membrane-impermeant ethidium homodimer-1 labels nucleic acids of membrane-compromised cells with red fluorescence. Membrane-permeant SYTO 10 dye labels the nucleic acids of live cells with green fluorescence, and membrane-impermeant DEAD Red dye labels nucleic acids of membrane-compromised cells with red fluorescence. A change in the level of cell viability is detected between the cells contacted with API subjected to stress and/or stability testing in standard glass vials as compared to the glass vials provided herein and appropriate controls (e.g., API not subject to stability testing, vehicle control).

In vivo toxicity assays are performed in animals. Typically preliminary assays are performed on normal subjects. However, if the disease or condition to be treated could alter the susceptibility of the subject to toxic agents (e.g., decreased liver function, decreased kidney function), toxicity testing in an appropriate model of the disease or condition can be advantageous. One or more doses of agents subjected to stability and/or stress testing are administered to animals. Typically, doses are far higher (e.g., 5 times, 10 times) the dose that would be used therapeutically and are selected, at least in part, on the toxicity of the API not subject to stability and/or stress testing. However, for the purpose of assaying stability of API, the agent can be administered at a single dose that is close to (e.g., 70%-90%), but not at, a dose that would be toxic for the API not subject to stability or stress testing. In single dose studies, after administration of the API subject to stress and/or stability testing (e.g., 12 hours, 24 hours, 48 hours, 72 hours), during which time blood, urine, and stool samples may be collected. In long term studies, animals are administered a lower dose, closer to the dose used for therapeutic treatment, and are observed for changes indicating toxicity, e.g., weight loss, loss of appetite, physical changes, or death. In both short and long term studies, organs are harvested and analyzed to determine if the API is toxic. Organs of most interest are those involved in clearance of the API, e.g., liver and kidneys, and those for which toxicity would be most catastrophic, e.g., heart, brain. An analysis is performed to detect a change in toxicity between the API subjected to stress and/or stability testing in standard glass vials as compared to the glass vials provided herein, as compared to API not subject to stability and/or stress testing and vehicle control. Changes, if any, in toxicity properties as a result of storage of the API under each condition are determined.

Example 10

Analysis of Pharmacodynamic Profiles

Pharmacodynamics includes the study of the biochemical and physiological effects of drugs on the body or on microorganisms or parasites within or on the body and the mechanisms of drug action and the relationship between drug concentration and effect. Mouse models for a large variety of disease states are known and commercially available (see, e.g., jaxmice.jax.org/query/f?p=205:1:989373419139701::::P1_ADV:1). A number of induced models of disease are also known.

Agents are incubated in containers as described in the stability testing and/or stress testing methods provided in Example 6. Preferably, the samples are incubated both in standard glass vials with appropriate closures and glass vials such as those provided herein. At the desired intervals, samples are removed and assayed for pharmacodynamic activity using known animal models. Exemplary mouse models for testing the various classes of agents indicated are known in the art.

The mouse is treated with the API subject to stability and/or stress testing. The efficacy of the API subject to stability and/or stress testing to treat the appropriate disease or condition is assayed as compared to API not subject to stability and/or stress testing and vehicle control. Changes, if any, in pharmacodynamic properties as a result of storage of the API under each condition are determined.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A delamination resistant pharmaceutical container comprising a pharmaceutical composition stored within the container, wherein the pharmaceutical container comprises a glass composition comprising:

$SiO_2$ in a concentration greater than about 74 mol. %;

alkaline earth oxide comprising MgO and CaO, wherein CaO is present in an amount greater than or equal to about 0.1 mol. % and less than or equal to about 1.0 mol. % relative to the glass composition, and a ratio (CaO (mol. %)/(CaO (mol. %)+MgO (mol. %))) is less than or equal to 0.5; and Y mol. % alkali oxide, wherein the alkali oxide comprises $Na_2O$ in an amount greater than about 8 mol. %, wherein the glass composition is free of boron and compounds of boron, and wherein the pharmaceutical composition comprises one of: an antidiabetic, an anti-neoplastic Mab, an antirheumatic, an antibacterial, a cytostatic, a vaccine, an immunosuppressant, an anti-fibrinolytic, an eye preparation, a MS therapeutic, a bone calcium regulator, an anti-coagulant, an anti-psychotic, an anti-metabolite, a radiopharmaceutical, an immunostimulant, a cytotoxic antibiotic, a cerebral and peripheral vasotherapeutic, a muscoskeletal agent, a nootropic, a CNS drug, a dermatological, an angiotensin II antagonist, a serelaxin, an anti-spasmodic, an anti-cholinergic, an interferon, an anti-anaemic, an anti-psoriasis agent, an anti-hyperlipidaemic, a cardiac therapeutic, an alkylating agent, a bronchodilator, a gastro-intestinal anti-inflammatory, a growth hormone, a hormone preparation, a non-narcotic analgesic, a diagnostic imaging agent, a haematological, a peripheral muscle relaxant, a growth hormone (human), or an immune globulin.

2. A delamination resistant pharmaceutical container comprising a pharmaceutical composition stored within the container, wherein the pharmaceutical container comprises a glass composition comprising:

from about 74 mol. % to about 78 mol. % $SiO_2$;

from about 4 mol. % to about 8 mol. % alkaline earth oxide, wherein the alkaline earth oxide comprises both MgO and CaO and a ratio (CaO (mol. %)/(CaO (mol. %)+MgO (mol. %))) is less than or equal to 0.5;

X mol. % $Al_2O_3$, wherein X is greater than or equal to about 2 mol. % and less than or equal to about 10 mol. %.; and Y mol. % alkali oxide, wherein the alkali oxide comprises $Na_2O$ in an amount greater than or equal to about 9 mol. % and less than or equal to about 15 mol. %, a ratio of Y:X is greater than 1, and the glass composition is free of boron and compounds of boron, and wherein the pharmaceutical composition comprises one of: of an antidiabetic, an anti-neoplastic Mab, an antirheumatic, an antibacterial, a cytostatic, a vaccine, an immunosuppressant, an anti-fibrinolytic, an eye preparation, a MS therapeutic, a bone calcium regulator, an anti-coagulant, an anti-psychotic, an anti-metabolite, a radiopharmaceutical, an immunostimulant, a cytotoxic antibiotic, a cerebral and peripheral vasotherapeutic, a muscoskeletal agent, a nootropic, a CNS drug, a dermatological, an angiotensin II antagonist, a serelaxin, an anti-spasmodic, an anti-cholinergic, an interferon, an anti-anaemic, an anti-psoriasis agent, an anti-hyperlipidaemic, a cardiac therapeutic, an alkylating agent, a bronchodilator, a gastro-intestinal anti-inflammatory, a growth hormone, a hormone preparation, a non-narcotic analgesic, a diagnostic imaging agent, a haematological, a peripheral muscle relaxant, a growth hormone (human) or an immune globulin.

3. A delamination resistant pharmaceutical container comprising a pharmaceutical composition stored within the container, wherein the pharmaceutical container comprises a glass composition comprising:

from about 74 mol. % to about 78 mol. % $SiO_2$;

alkaline earth oxide comprising both CaO and MgO, wherein the alkaline earth oxide comprises CaO in an amount greater than or equal to about 0.1 mol. % and less than or equal to about 1.0 mol. % relative to the glass composition, and a ratio (CaO (mol. %)/(CaO (mol. %)+MgO (mol. %))) is less than or equal to 0.5;

X mol. % $Al_2O_3$, wherein X is greater than or equal to about 2 mol. % and less than or equal to about 10 mol. %; and Y mol. % alkali oxide, wherein the alkali oxide comprises from about 0.01 mol. % to about 1.0 mol. % $K_2O$ and a ratio of Y:X is greater than 1, and the glass composition is free of boron and compounds of boron, and wherein the pharmaceutical composition comprises one of: an antidiabetic, an anti-neoplastic Mab, an antirheumatic, an antibacterial, a cytostatic, a vaccine, an immunosuppressant, an anti-fibrinolytic, an eye preparation, a MS therapeutic, a bone calcium regulator, an anti-coagulant, an anti-psychotic, an anti-metabolite, a radiopharmaceutical, an immunostimulant, a cytotoxic antibiotic, a cerebral and peripheral vasotherapeutic, a muscoskeletal agent, a nootropic, a CNS drug, a dermatological, an angiotensin II antagonist, a serelaxin, an anti-spasmodic, an anti-cholinergic, an interferon, an anti-anaemic, an anti-psoriasis agent, an anti-hyperlipidaemic, a cardiac therapeutic, an alkylating agent, a bronchodilator, a gastro-intestinal anti-inflammatory, a growth hormone, a hormone preparation, a non-narcotic analgesic, a diagnostic imaging agent, a haematological, a peripheral muscle relaxant, a growth hormone (human) or an immune globulin.

4. The pharmaceutical container of claim 1, wherein the container comprises a vial, cartridge, syringe, ampoule, bottle, flask, or vacutainer.

5. The pharmaceutical container of claim 1, wherein the container is delamination resistant.

6. The pharmaceutical container of claim 1, wherein the container has a delamination factor of 1.

7. The pharmaceutical container of any one of 1, 2, and 3, wherein
   (i) the antidiabetic is selected from the group consisting of insulin aspart; insulin degludec; insulin glargine recombinant; dulaglutide; lixisenatide; hyaluronidase (human); insulin; liraglutide; insulin glargine; albiglutide; insulin lispro recombinant; insulin (human); insulin detemir; exenatide synthetic; insulin aspart and insulin aspart protamine; insulin aspart and insulin degludec; hyaluronidase (human) and insulin lispro/insulin aspart; insulin glargine and lixisenatide; and insulin degludec and liraglutide;
   (ii) the antineoplastic is selected from the group consisting of Bavituximab, Onartuzumab, yttrium Y-90 clivatuzumab tetraxetan, obinutuzumab, cixutumumab, necitumumab, pertuzumab, brentuximab vedotin, nivolumab, trastuzumab emtansine, siltuximab, elotuzumab, ramucirumab, Ipilimumab, Rituximab, Trastuzumab, and bevacizumab;
   (iii) the antirheumatic is selected from the group consisting of tabalumab, sarilumab, Tocilizumab, Infliximab, Etanercept, Abatacept, certolizumab pegol, Golimumab, and Adalimumab;
   (iv) the antibacterial is selected from the group consisting of ceftolozane sulfate, and tazobactam sodium, ceftaroline fosamil, brilacidin, and tedizolid phosphate;
   (v) the cytostatic is selected from the group consisting of CT-107, ganetespib, CUDC-101, Reolysin, AEZS-108, velimogene aliplasmid, imetelstat sodium, algenpantucel-L, retaspimycin hydrochloride, astuprotimut-R, vosaroxin, BiovaxID, iniparib, Bortezomib, and carfilzomib;
   (vi) the vaccine is selected from the group consisting of meningococcal B vaccine; herpes zoster vaccine; hepatitis B vaccine; human papillomavirus (HPV) vaccine; pneumococcal vaccine; DTPw; influenza vaccine; hepatitis A and B vaccine; DTP, hepatitis B, and polio vaccine; and PENTAct-H1B;
   (vii) the immunosuppressant is selected from the group consisting of epratuzumab, eritoran tetrasodium, blisibimod, and ustekinumab;
   (viii) the anti-fibrinolytic is selected from the group consisting of turoctocog alfa, vonicog alfa, factor VIII, eptacog alfa, and octocog alfa;
   (ix) the eye preparation is selected from the group consisting of Ocriplasmin, Aflibercept, and Ranibizumab;
   (x) the MS therapeutic is selected from the group consisting of Alemtuzumab, ocrelizumab, daclizumab, peginterferon beta-1a, Natalizumab, glatiramer acetate, and interferon beta-1a;
   (xi) the bone calcium regulator is selected from the group consisting of romosozumab, Denosumab, and recombinant human teriparatide;
   (xii) the anti-coagulant is selected from the group consisting of semuloparin sodium, otamixaban, and enoxaparin sodium
   (xiii) the anti-psychotic is aripiprazole;
   (xiv) the anti-metabolite is gemcitabine elaidate;
   (xv) the radiopharmaceutical is radium Ra-223 chloride;
   (xvi) the immunostimulant is Pegfilgrastim;
   (xvii) the cytotoxic antibiotic is doxorubicin hydrochloride;
   (xviii) the cerebral and peripheral vasotherapeutic is defibrotide;
   (xix) the musculoskeletal agent is selected from the group consisting of Drisapersen, eteplirsen, and asfotase alfa;
   (xx) the nootropic is solanezumab;
   (xxi) the CNS drug is neural stem cells;
   (xxii) the dermatological is secukinumab;
   (xxiii) the angiotensin II antagonist is serelaxin;
   (xxiv) the anti-spasmodic or anti-cholinergic is teduglutide;
   (xxv) the interferon is peginterferon lambda-1a or peginterferon alfa-2a;
   (xxvi) the anti-anaemic is ferric pyrophosphate or darbepoetin alfa;
   (xxvii) the anti-psoriasis agent is ixekizumab;
   (xxviii) the anti-hyperlipidaemic is alirocumab;
   (xxix) the cardiac therapeutic is cenderitide;
   (xxx) the alkylating agent is palifosfamide;
   (xxxi) the bronchodilator is lebrikizumab;
   (xxxii) the gastro-intestinal anti-inflammatory is vedolizumab;
   (xxxiii) the hormone preparation is parathyroid hormone 1-84;
   (xxxiv) the non-narcotic analgesic is fulranumab;
   (xxxv) the diagnostic imaging agent is Minretumomab;
   (xxxvi) the haematological is Eculizumab
   (xxxvii) the peripheral muscle relaxant is botulinum toxin type A; and
   (xxxviii) the pharmaceutical composition comprises an agent selected from the group consisting of elosulfase alfa, Protectan CBLB502, HGT-1410, HGT 1110, and sebelipase alfa.

8. The pharmaceutical container of claim 1, wherein the pharmaceutical composition comprises a citrate buffer or a phosphate buffer.

9. The pharmaceutical container of claim 8, wherein the buffer is selected from the group consisting of sodium citrate, saline-sodium citrate (SSC), monosodium phosphate and disodium phosphate.

10. The pharmaceutical container of claim 1, wherein the pharmaceutical composition is a solution having a pH between about 7 and about 11.

11. The pharmaceutical container of claim 1, wherein the concentration of $SiO_2$ is less than or equal to about 80 mol. %.

12. The pharmaceutical container of claim 1, wherein the glass composition is free from phosphorous and compounds of phosphorous.

13. The pharmaceutical container of claim 1, further comprising X mol. % $Al_2O_3$, wherein a ratio of Y:X is greater than 1.

14. The pharmaceutical container of claim 13, wherein the ratio of Y:X is less than or equal to 2.

15. The pharmaceutical container of claim 13, wherein X is greater than or equal to about 2 mol. % and less than or equal to about 10 mol. %.

16. The pharmaceutical container of claim 1, wherein the alkaline earth oxide is present in an amount from about 3 mol. % to about 13 mol. %.

17. The pharmaceutical container of claim 13, wherein the ratio of Y:X is greater than or equal 1.3 and less than or equal to 2.

18. The pharmaceutical container of claim 13, wherein X is greater than or equal to about 5 mol. % and less than or equal to about 7 mol. %.

19. The pharmaceutical container of claim 1, wherein the ratio (CaO (mol. %)/(CaO (mol. %)+MgO (mol. %))) is less than or equal to 0.3.

20. The pharmaceutical container of claim 1, further comprising $SnO_2$.

21. The pharmaceutical container of claim 2, wherein the ratio of Y:X is less than or equal to about 2.

22. The pharmaceutical container of claim 2, wherein the ratio of Y:X is greater than or equal to about 1.3 and less than or equal to about 2.0.

23. The pharmaceutical container of claim 2, wherein the ratio (CaO (mol. %)/(CaO (mol. %)+MgO (mol. %))) is less than or equal to 0.1.

24. The pharmaceutical container of claim 2, wherein the alkaline earth oxide comprises from about 3 mol. % to about 7 mol. % MgO.

25. The pharmaceutical container of claim 2, wherein the alkaline earth oxide comprises CaO in an amount greater than or equal to about 0.1 mol. % and less than or equal to about 1.0 mol. %.

26. The pharmaceutical container of claim 2, wherein the alkali oxide further comprises $K_2O$ in an amount greater than or equal to about 0.01 mol. % and less than or equal to about 1.0 mol. %.

27. The pharmaceutical container of claim 2, wherein X is greater than or equal to about 5 mol. % and less than or equal to about 7 mol. %.

28. The pharmaceutical container of claim 3, wherein the ratio of Y:X is less than or equal to 2.

29. The pharmaceutical container of claim 3, wherein the ratio of Y:X is greater than or equal to 1.3 and less than or equal to 2.0.

30. The pharmaceutical container of claim 3, wherein the ratio (CaO (mol. %)/(CaO (mol. %)+MgO (mol. %))) is less than or equal to 0.1.

31. The pharmaceutical container of claim 3, wherein the glass composition is free of phosphorous and compounds of phosphorous.

32. The pharmaceutical container of claim 3, wherein the alkali oxide further comprises $Na_2O$ in an amount greater than about 8 mol. %.

33. The pharmaceutical container of claim 3, wherein the alkali oxide further comprises $Na_2O$ in an amount greater than or equal to about 2 mol. % and less than or equal to about 15 mol. %.

34. The pharmaceutical container of claim 3, wherein the alkali oxide further comprises from about 9 mol. % to about 13 mol. % $Na_2O$.

35. The pharmaceutical container of claim 3, wherein X is greater than or equal to about 5 mol. % and less than or equal to about 7 mol. %.

* * * * *

UNITED STATES PATENT AND TRADEMARK OFFICE
CERTIFICATE OF CORRECTION

PATENT NO. : 9,474,688 B2
APPLICATION NO. : 13/660680
DATED : October 25, 2016
INVENTOR(S) : Wendell Porter Weeks et al.

It is certified that error appears in the above-identified patent and that said Letters Patent is hereby corrected as shown below:

In the Claims

In Column 105, Line 51, Claim 1, delete "muscoskeletal" and insert -- musculoskeletal --, therefor.

In Column 106, Line 37, Claim 2, delete "of an" and insert -- an --, therefor.

In Column 106, Line 44, Claim 2, delete "muscoskeletal" and insert -- musculoskeletal --, therefor.

In Column 106, Line 53, Claim 2, delete "or" and insert -- , or --, therefor.

In Column 107, Line 13, Claim 3, delete "muscoskeletal" and insert -- musculoskeletal --, therefor.

In Column 107, Line 22, Claim 3, delete "or" and insert -- , or --, therefor.

In Column 108, Line 51, Claim 7, delete "Eculizumab" and insert -- Eculizumab; --, therefor.

Signed and Sealed this
Nineteenth Day of January, 2021

Andrei Iancu
*Director of the United States Patent and Trademark Office*